(12) United States Patent
Bassett, Jr. et al.

(10) Patent No.: US 6,453,241 B1
(45) Date of Patent: Sep. 17, 2002

(54) METHOD AND SYSTEM FOR ANALYZING BIOLOGICAL RESPONSE SIGNAL DATA

(75) Inventors: Douglas Bassett, Jr., Kirkland; Stewart Buskirk, Brier; Andrey Bondarenko, Redmond, all of WA (US)

(73) Assignee: Rosetta Inpharmatics, Inc., Kirkland, WA (US)

( * ) Notice: Subject to any disclaimer, the term of this patent is extended or adjusted under 35 U.S.C. 154(b) by 0 days.

(21) Appl. No.: 09/220,276

(22) Filed: Dec. 23, 1998

(51) Int. Cl.[7] ............................. G06F 19/00; C12Q 1/68
(52) U.S. Cl. ............................. 702/19; 702/20; 702/21; 435/6
(58) Field of Search .............................. 702/19, 20, 21; 435/6; 706/15–23

(56) References Cited

U.S. PATENT DOCUMENTS

| | | | | |
|---|---|---|---|---|
| 5,181,162 A | * | 1/1993 | Smith et al. | 364/419 |
| 5,338,659 A | * | 8/1994 | Kauvar et al. | 435/7.1 |
| 5,510,270 A | | 4/1996 | Fodor et al. | |
| 5,556,752 A | | 9/1996 | Lockhart et al. | |
| 5,569,588 A | | 10/1996 | Ashby et al. | |
| 5,578,832 A | | 11/1996 | Trulson et al. | |
| 5,586,033 A | * | 12/1996 | Hall | 364/424.07 |
| 5,590,250 A | | 12/1996 | Lamping et al. | |
| 5,619,632 A | | 4/1997 | Lamping et al. | |
| 5,630,125 A | | 5/1997 | Zellweger | |
| 5,777,888 A | | 7/1998 | Rine et al. | |
| 5,966,712 A | | 10/1999 | Sabatini et al. | |
| 5,970,500 A | | 10/1999 | Sabatini et al. | |
| 6,165,709 A | | 12/2000 | Friend et al. | |
| 6,185,561 B1 | | 2/2001 | Balaban et al. | |
| 6,203,987 B1 | | 3/2001 | Friend et al. | |
| 6,245,517 B1 | | 6/2001 | Chen et al. | |

FOREIGN PATENT DOCUMENTS

| | | |
|---|---|---|
| WO | WO 97/27317 | 1/1996 |
| WO | WO 97/10365 | 9/1996 |

OTHER PUBLICATIONS

Eisen, et al., 1998, "Cluster Analysis and Display of Genome–Wide Expression Patterns," *Proc. Natl. Acad. Sci., USA*, 95: 14863–14868.
Duda et al., 2001, *Pattern Classification*, Second Edition, A Wiley–Interscience Publication, Chapter 10: 550–555.
Sokal et al., 1958, "A Statistical Method for Evaluating Systematic Relationships," *The University of Kansas Science Bulletin*, vol. 38: 1409–1438.
Weinstein et al. (Science 275, 343–349, 1997).*
Zhao et al. 1995, "High–density cDNA filter analysis: a novel approach for large–scale, quantitative analysis of gene expression," *Gene* 156: 207–213.
Blanchard et al., 1996, "Sequence to array: Probing the genome's secrets," *Nature Biotechnology* 14:1649.
Blanchard et al., 1996, "High–Density Oligonucleotide Arrays," *Biosensors & Bioelectronics* 11:687–90.
Chee et al., 1996, "Accessing Genetic Information with High–Density DNA Arrays," *Science* 274:610–614.
Chait, 1996, "Trawling for proteins in the post–genome era," *Nat. Biotech.* 14:1544.
DeRisi et al., 1996, "Use of a cDNA microarray to analyze gene expression patterns in human cancer," Nature Genetics 14:457–460.
DeRisi et al., 1997, "Exploring the metabolic and genetic control of gene expression on a genomic scale," *Science* 278:680–686.
Lamping and Rao, 1994, "Laying out and Visualizing Large Trees Using a Hyperbolic Space," *UIST '94* Nov. 2–4, 1994. Jul. 13, 1999Marina del Rey, California. pp. 13 and 14.
Lockhart et al., 1996, "Expression monitoring by hybridization to high–density oligonucleotide arrays," *Nature Biotechnology* 14:1675–1680.
Marton et al., 1998, "Drug target validation and identification of secondary drug target effects using DNA microarrays," *Nat. Med.* 4(11):1293–1301.
McCormack et al., 1997, "Direct analysis and identification of proteins in mixtures by LC/MS/MS and database searching at low–femtomole level", *Anal. Chem.* 69:767–776.
Schena et al., 1995, "Quantitative monitoring of gene expression patterns with a complementary DNA micro–array," *Science 270*: 467–470.
Schena et al., 1996, "Parallel human genome analysis; microarray–based expression monitoring of 1000 genes," *Proc. Natl. Acad. Sci. USA* 93:10614–10619.
Shalon et al., 1996, "A DNA microarray system for analyzing complex DNA samples using two–color fluorescent probe hybridization," *Genome Res.* 6:639–645.

* cited by examiner

*Primary Examiner*—John S. Brusca
(74) *Attorney, Agent, or Firm*—Pennie & Edmonds LLP

(57) ABSTRACT

A system, method, and computer program product for enhanced computer-aided analysis of biological response data is disclosed. In a preferred embodiment, biological datasets are graphically selected by a user from a first active biological viewer window on a user computer display and projected onto one or more other active biological viewers on the display. The selected data is highlighted in the destination biological viewers using contrast or color differentiation from other data appearing in the destination windows. In another preferred embodiment, hierarchical cluster trees from biological signal profiles are presented in a hyperbolic display fashion. In another preferred embodiment, biological menu and submenu items utilized by the user computer are not stored in the user computer, but rather are stored a central biological response database. Biological menus and submenus are generated at startup time based on queries to the central biological response database, allowing for increased flexibility, changeability, and customization of the biological menus. In another preferred embodiment, correlation data between biological signal profile data is precomputed when the experiments are added to the central biological response database, eliminating the need for real time computation of correlation coefficients by the user computer.

83 Claims, 26 Drawing Sheets

EXPRESS
FILE EDIT WINDOWS HELP
EXPERIMENTS  SCANS  BIOSETS  GENES
CRITERIA
CHIP BARCODE  ▽  CONDITION  EQUAL TO  VALUE
MORE  LESS  SHOW ALL  SEARCH
☐PLOT ☐TABLE ☐ROAST ☐BIOSET ☐INFO

| CHIP BARCODE(S) | HYB NAME | CONTROL? | SCAN DATE | ANALYSIS DATE | MEAN SIG/BKGD | SAMPLE (G) | SAMPLE (R) |
|---|---|---|---|---|---|---|---|
| CRI000000770 | WT vs. WT -AA-dUTP LINKAGE | • | 22-Sep-98 | 22-Sep-98 | 6.432222 | TH346 | TH346 |
| CRI000000771 | WT vs. WT -AA-dUTP LINKAGE | • | 22-Sep-98 | 22-Sep-98 | 2.527776 | TH346 | TH346 |
| CRI000000772,CRI000000773(-),CRI... | +/+ vs. +/cph1 | • | 26-Jan-98 | 18-Sep-98 | 5.587819 | J90 | J91 |
| CRI000000774,CRI000000775(-),CRI... | +/+ vs. +/cph1 | • | 27-Jan-98 | 18-Sep-98 | 8.44295 | J92 | J93 |
| CRI000000776,CRI000000777(-),CRI... | +/+ vs. +/cph1/cph1 | • | 27-Jan-98 | 18-Sep-98 | 10.155289 | J94 | J95 |
| CRI000000778,CRI000000779(-),CRI... | +/+ vs. +/cph1/cph1 | • | 27-Jan-98 | 18-Sep-98 | 6.770993 | J96 | J97 |
| CRI000000788,CRI000000377,CRI... | CONTROL vs. CONTROL | • | 18-Mar-98 | 08-Oct-98 | 4.538672 | CONTROL | CONTROL |
| CRI000000821(-) | wt vs. cna1 cna2 | • | 12-Jan-98 | 18-Sep-98 | 32.64178 | J1 | J10 |
| CRI000000823(-) | wt vs. cna1 cna2 | • | 12-Jan-98 | 18-Sep-98 | 32.287785 | J1 | J10 |
| CRI000001040,CRI000001122 | wt vs. wt + 3.1 ug/ul FK506 | • | 21-Jan-98 | 18-Sep-98 | 21.235388 | M453 | M454 |
| CRI000001041,CRI000001123 | wt vs. wt + 10 ug/ul FK506 | • | 22-Jan-98 | 19-Sep-98 | 23.283955 | M451 | M452 |
| CRI000001051 | wt vs. wt + 3.1 ug/ul FK506 | • | 14-Jan-98 | 18-Sep-98 | 11.326113 | M143 | M144 |
| CRI000001052 | wt vs. wt + 0.31 ug/ul FK506 | • | 15-Jan-98 | 18-Sep-98 | 22.540081 | M147 | M148 |
| CRI000001053 | wt vs. wt + 0.1 ug/ul FK506 | • | 15-Jan-98 | 18-Sep-98 | 20.395292 | M149 | M150 |
| CRI000001054 | wt vs. wt | • | 15-Jan-98 | 18-Sep-98 | 8.826204 | M151 | M152 |
| CRI000001057 | wt vs. wt + 1.0 ug/ml CsA | • | 12-Jan-98 | 18-Sep-98 | 17.70117 | M455 | M456 |
| CRI000001058,CRI000001121 | wt vs. wt + 0.31 ug/ml CsA | • | 21-Jan-98 | 19-Sep-98 | 22.275217 | M457 | M458 |
| CRI000001059 | wt vs. wt + 0.1 ug/ml CsA | • | 12-Jan-98 | 18-Sep-98 | 26.39537 | M459 | M460 |
| CRI000001061,CRI000001069(-),CRI... | wt vs. wt + 60 ug/ml CsA | • | 13-Apr-98 | 21-Apr-98 | 17.70224 | M473 | M474 |
| CRI000001062,CRI000001070(-),CRI... | wt vs. wt + 30 ug/ml CsA | • | 13-Apr-98 | 21-Apr-98 | 19.206842 | M475 | M476 |
| CRI000001063,CRI000001072(-),CRI... | wt vs. wt + 15 ug/ml CsA | • | 13-Apr-98 | 21-Apr-98 | 18.933674 | M477 | M478 |
| CRI000001064,CRI000001073(-),CRI... | wt vs. wt + 6 ug/ml CsA | • | 13-Apr-98 | 21-Apr-98 | 20.4957 | M479 | M480 |
| CRI000001065 | wt vs. 3 ug/ml CsA | • | 29-Jan-98 | 18-Sep-98 | 17.031063 | M481 | M482 |
| CRI000001066 | + vs. sin3 | • | 28-Jan-98 | 18-Sep-98 | 18.785536 | M441 | M443 |
| CRI000001067 | + vs. hda1 | • | 28-Jan-98 | 19-Sep-98 | 27.34851 | M441 | M444 |
| CRI000001068 | + vs. sin3 | • | 28-Jan-98 | 18-Sep-98 | 17.839863 | M441 | M445 |
| CRI000001074 | + vs. rpd3 | • | 28-Jan-98 | 18-Sep-98 | 20.604902 | M447 | M448 |
| CRI000001075 | + vs. hda1 | • | 28-Jan-98 | 18-Sep-98 | 21.681297 | M447 | M449 |

1046 RECORDS FOUND

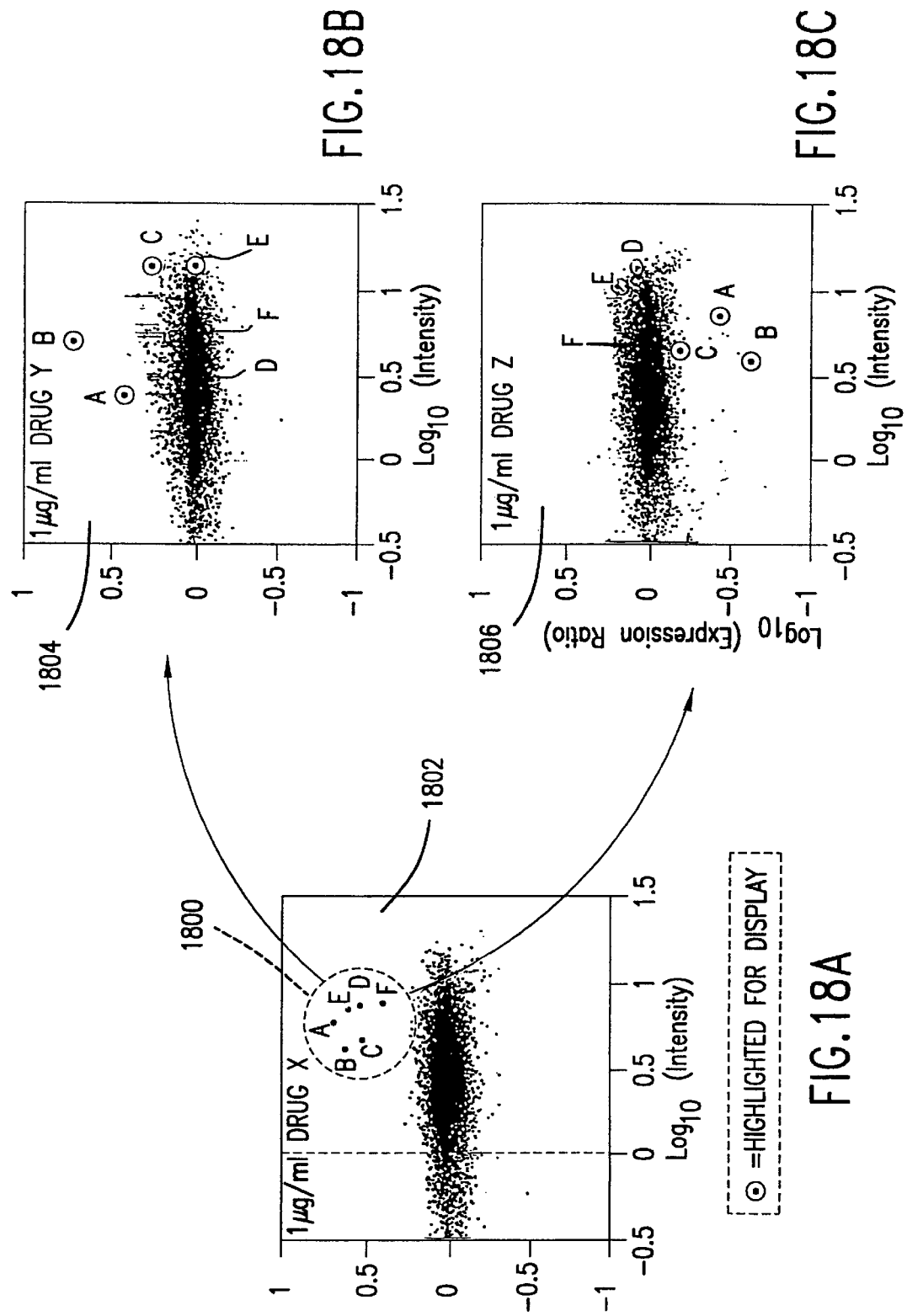

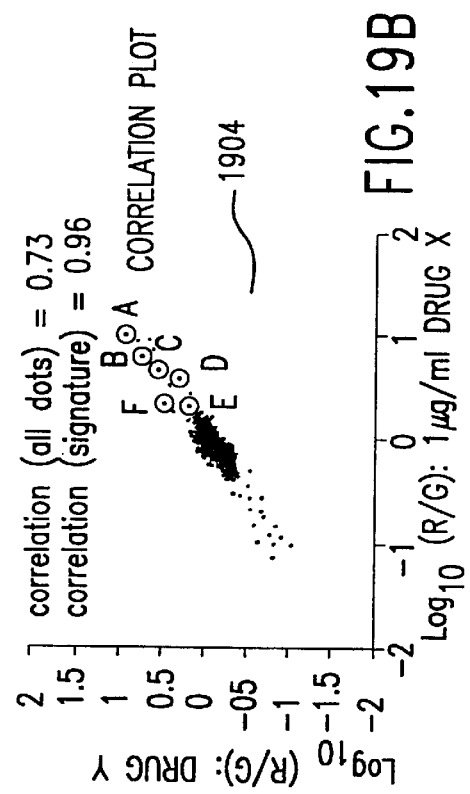
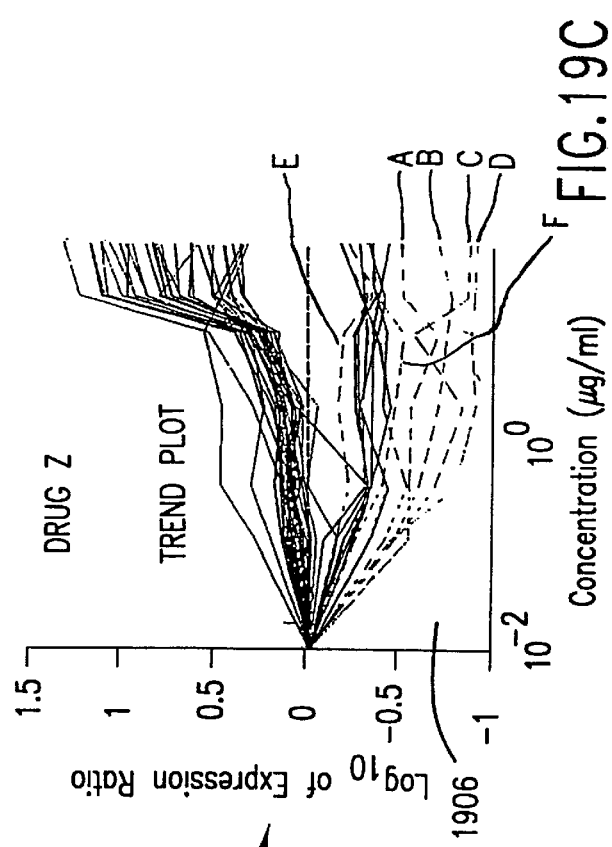
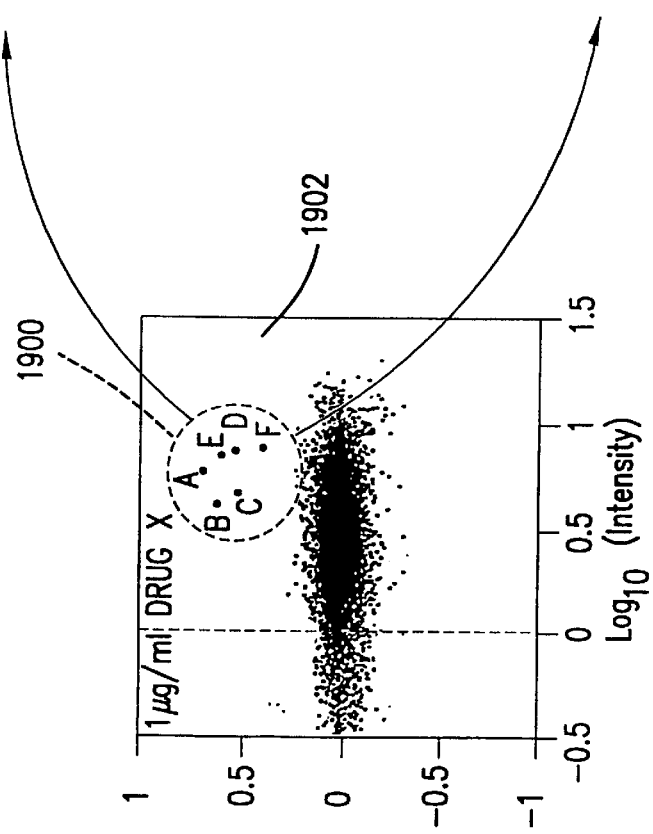
FIG. 19A
FIG. 19B
FIG. 19C

FIG. 22

METHOD AND SYSTEM FOR ANALYZING BIOLOGICAL RESPONSE SIGNAL DATA

1. FIELD OF THE INVENTION

The present invention relates to the field of computer-assisted analysis of biological information. In particular, the present invention relates to a method and system for management of a database containing biological response signal data and for presentation of useful analytical displays of information therefrom.

2. BACKGROUND OF THE INVENTION

The analysis of complex systems such as biological organisms is aided by the use of relational database systems for storing and retrieving large amounts of biological data. The advent of high-speed wide area networks and the Internet, together with the client/server based model of relational database management systems, is particularly well-suited for allowing researchers to access and meaningfully analyze large amounts of biological data given the appropriate hardware and software computing tools.

Computerized analysis tools are particularly useful in experimental environments involving biological response signals. By way of nonlimiting example, biological response signal data can be obtained and/or gathered using biological response signal matrices, that is, physical matrices of biological material that transmit machine-readable signals corresponding to biological content or activity at each site in the matrix. In these systems, responses to biological or environmental stimuli may be measured and analyzed in a large-scale fashion through computer-based scanning of the machine-readable signals, e.g. photons or electrical signals, into numerical matrices, and through the storage of the numerical data into relational databases.

As a further nonlimiting example, biological response signal data can be obtained and/or gathered using serial analysis of gene expression (SAGE) or other technologies for measuring gene/protein expression levels that may not use a matrix or microarray but otherwise produce measurable signals. Generally speaking, biological response signals may be measured after a perturbation of a biological sample including, for example, the exposure of a biological sample to a drug candidate, the introduction of an exogenous gene into a biological sample, the deletion of a gene from the biological sample, or changes in the culture conditions of the biological sample.

A useful outcome of the scientific experimentation being performed involves the understanding of the relationships between genes and perturbations, understanding that promotes other useful outcomes such as the invention of new drugs or other therapies. Often, relationships between perturbation and gene expression levels sheds light on known or unknown biological pathways. There is an ongoing need in the art to generate better and more useful ways for computers to assist in analyzing the large volume of biological response data that can exist for even the most simple biological organisms.

3. SUMMARY OF THE INVENTION

A system, method, and computer program product are provided for improved computer-aided analysis of biological data derived from machine readable outputs of experiments performed on a plurality of biological samples. Responsive to search and execution commands from the user, a plurality of biological viewer windows are spawned on a user computer display. The user may then select a source dataset from one of the biological viewers and execute a project selection command, wherein the source dataset is then projected onto the other biological viewers. The projections are characterized by a highlighted display of biological data points in the destination biological viewers corresponding to items in the source dataset. The selected data is highlighted in the destination biological viewers using contrast or color differentiation from other destination window data.

In another preferred embodiment, the user may spawn a hierarchical cluster tree biological viewer that displays genes or experiments grouped based on similarity of behavior, wherein the hierarchical cluster tree is displayed in a hyperbolic display fashion. In one form, the hierarchical cluster tree may be, for example, a gene coregulation tree. When displayed in a hyperbolic display fashion, convenient viewing of the hierarchical cluster tree is enabled, whereby the user may move around the tree and zoom in and out of various areas of the tree without losing perspective of their current location relative to the "root" of the tree.

In another preferred embodiment, biological menu and submenu items that are displayed to the user during searches, projections, and the like are not stored in the user computer, but rather are stored in a central biological response database. Biological menus and submenus are generated at startup based on queries to the central biological response database, allowing for increased flexibility, changeability, and customization of the biological menus and submenus.

In another preferred embodiment, correlation data between expression array experiments is precomputed when the experiments are added to the central biological response database. This eliminates the need for real time computation of correlation coefficients or other similarity scores by the user computer, resulting in considerable time savings when the user requests correlation data among selected sets of experiments.

4. BRIEF DESCRIPTION OF THE DRAWINGS

FIG. 4 shows a query composition and results display window in accordance with a preferred embodiment;

FIG. 13 shows a main search window in accordance with a preferred embodiment having an expanded criteria menu;

FIG. 15 shows the main search window of FIG. 13 with a pulled-down dynamic search condition menu;

FIGS. 17–19 show examples of projections of selected biological data in accordance with a preferred embodiment;

FIG. 22 shows a user menu that allows for subtraction of biological signal profiles or combinations thereof from one another;

5. DETAILED DESCRIPTION

Figure 1:
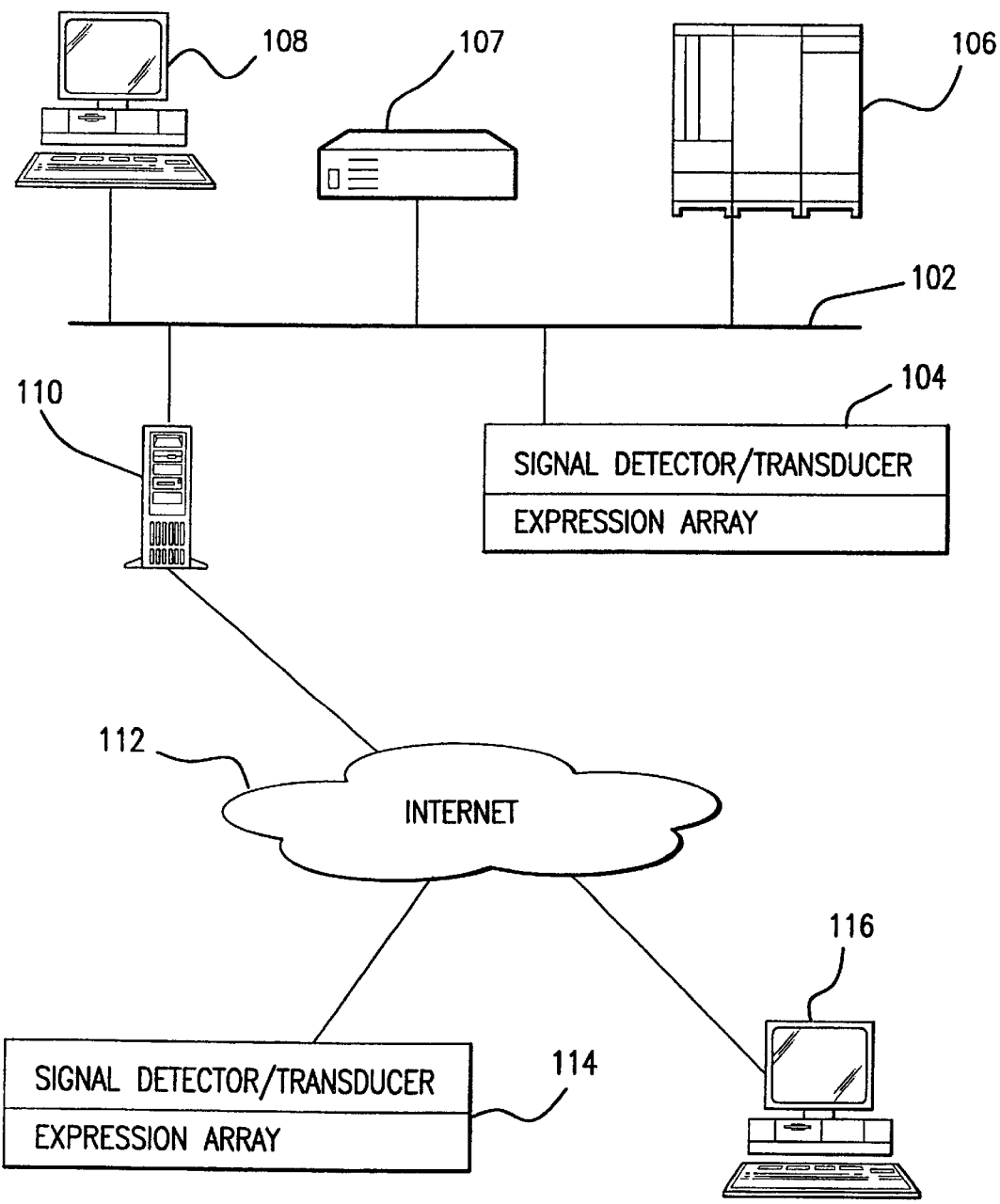
FIG. 1 shows a biological response data network in accordance with a preferred embodiment.

This section presents a detailed description of the invention and its applications. In particular, Section 5.1 generally describes the methods of the invention. Sections 5.2 and 5.3 describe, in detail, types of biological response signals which may be analyzed according to the methods of the present invention, as well as methods for obtaining such biological response signals. In particular, Section 5.2 describes methods of measuring cellular constituents and Section 5.3 describes various targeted methods of perturbing the biological state of a cell or organism.

The description is by way of several exemplary illustrations, in increasing detail and specificity, of the general methods of the invention. The examples are non-limiting, and related variants that will be apparent to one skilled in the art are intended to be encompassed by the appended claims. Following these examples are descriptions of embodiments of the data gathering steps that accompany the general methods.

5.1. Overview of the Methods of the Invention

Preferred embodiments are described herein with respect to one example of a system yielding biological response signals, although it is to be appreciated that the scope of the preferred embodiments is not so limited and may be applied to any of a variety of experimental environments involving biological response signals. An expression array is a microarray adapted to generate light signals at each matrix site responsive to an amount of mRNA being expressed for a particular gene product at that site. Such systems are generally described in U.S. Pat. No. 6,203,987, "Methods for Using Co-regulated Genesets to Enhance Detection and Classification of Gene Expression Patterns," filed Oct. 27, 1998; U.S. patent application Ser. No. 09/220,142, "Methods of Characterizing Drug Activities Using Consensus Profiles," filed Dec. 23, 1998; U.S. patent application Ser. No. 09/220,274, "Methods for Robust Discrimination of Profiles," filed Dec. 23, 1998; and U.S. patent application Ser. No. 09/220,275, "Methods for Using Co-regulated Genesets to Enhance Detection and Classification of Gene Expression Patterns,". The contents of each of the these applications is hereby incorporated by reference into the present application. Moreover, all publications cited herein are incorporated by reference in their entirety.

Microarrays are known in the art and consist of a surface to which probes that correspond in sequence to genes or gene products (e.g., cDNAs, mRNAs, cRNAs, polypeptides, and fragments thereof), can be specifically hybridized or bound at a known position. The microarray is an array (i.e., a matrix) in which each position represents a discrete binding site for a gene or gene product (e.g., a DNA or protein), and in which binding sites are present for most or almost all of the genes in the organism's genome.

As disclosed supra, a perturbation includes but is not limited to the exposure of a biological sample to a drug candidate, the introduction of an exogenous gene into a biological sample, the deletion of a gene from the biological sample, or changes in the culture conditions of the biological sample. Responsive to a perturbation, a gene corresponding to a microarray site may, to varying degrees, be (a) upregulated, in which more mRNA corresponding to that gene may be present, (b) downregulated, in which less mRNA corresponding to that gene may be present, or (c) unchanged. The amount of upregulation or downregulation for a particular matrix location is made capable of machine measurement using known methods which cause photons of a first wavelength (e.g., green) to be emitted for upregulated genes and photons of a second wavelength (e.g., red) to be emitted for downregulated genes.

After perturbation and appropriate processing of the microarray, the photon emissions are scanned into numerical form, and an image of the entire microarray is stored in the form of an image representation such as a color JPEG format. The presence and degree of upregulation or downregulation of the gene at each microarray site represents, for the perturbation imposed on that site, the relevant output data for that experimental run or "scan."

FIG. 1 shows a biological response data network 100 for storage, retrieval, and analysis of biological response data in accordance with a preferred embodiment. FIG. 1 shows a data network 102 coupled to a scanning device 104, a database server 106, a computational server 107, an exemplary user computer 108, and a gateway computer 110. Gateway computer 110 is coupled to the Internet 112 which, in turn, is coupled to a remote scanning device 114 and a remote user computer 116. While a single instance of each of the above elements is disclosed in FIG. 1 for purposes of clarity of disclosure, it is to be appreciated that a typical implementation will generally include a plurality of user computers, data networks, scanning devices, computational servers, database servers, etc., in accordance with the preferred embodiments.

Data network 102 generally corresponds to a private local area network (LAN) such as an Ethernet, Token Ring, or FDDI (Fiber Distributed Data Interface) LAN, although the scope of the preferred embodiments is not so limited. Indeed, data network 102 may also comprise a wide area network (WAN) coupling LANs distributed across many corporate or university sites coupled by data bridges, routers, and switches as necessary. Protocols for coupling various sites corresponding to data network 102 may include X.25, SMDS (Switched Multimegabit Data Service), Frame Relay, ATM (Asynchronous Transfer Mode), or other data protocols as necessary. In general, the data network 102 should be capable of providing high-speed data communications between the database server 106 and other nodes in the network.

Figure 2:
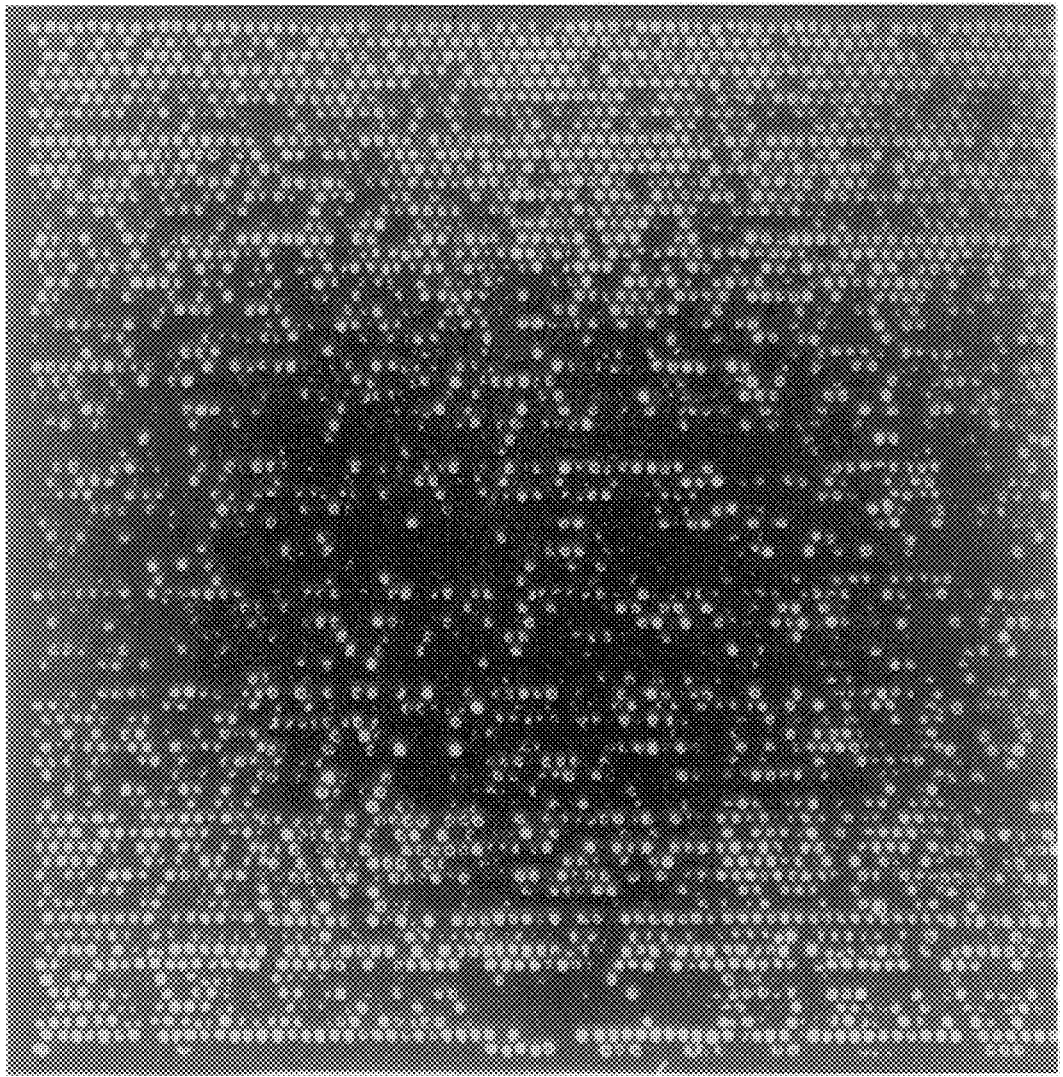
FIG. 2 shows an image of a DNA microarray.

FIG. 2 shows a JPEG image 200 of an expression array scan produced by scanning device 104. While JPEG image 200 appears in black-and-white in FIG. 2 for ease of photocopy distribution of the present disclosure, it is actually a color image as known in the art, and represents the primary data generated from any gene/protein expression level measurement technology. As indicated in FIG. 1, scanning device 104 comprises a signal detector/transducer for scanning an expression array using methods known in the art to provide experimental data in the form of the color JPEG image 200. The color JPEG image 200 is transmitted to computational server 107 and database server 106 using the networking protocol appropriate for the data network 102. A significant amount of processing may be performed by the scanning device 104 or computational server 107 prior to or following transmission of the color JPEG image 200 to database server 106. The data resulting from this processing is generally a set of alphanumeric data identifying various characteristics of the expression array, such as quantitative signal intensity levels, expression ratios, p-values, the total number of usable sites on the expression array, and a large amount of other information known in the art. This alphanumeric data is sent in along with JPEG image 200 for storage in the database server 106. Remote scanning device 114 comprises similar hardware and software for performing tasks similar to scanning device 104, except that remote scanning device 114 is adapted to communicate with database server 106 over the Internet 112 using, for example, a TCP/IP protocol.

It is to be appreciated that scanning device 104 and the corresponding color JPEG image 200 represent only a single example of biological response signal data systems in accordance with a preferred embodiment, and that other systems for generating biological response signals are within the spirit and scope of the preferred embodiments. The analytical tools disclosed herein are broadly applicable to gene and protein expression data. For example, biological response signal data including gene expression level data generated from serial analysis of gene expression (SAGE, supra) (Velculescu et al., 1995, Science, 270:484) and related technologies are within the scope of data suitable for analysis of the preferred embodiments. Other methods of generating biological response signals suitable for the preferred embodiments include, but are not limited to: traditional Northern and Southern blot analysis; antibody studies; chemiluminescence studies based on reporter genes such as luceriíase or green fluorescent protein; Lynx; READS (GeneLogic); and methods similar to those disclosed in U.S. Pat. No. 5,569,588 to Ashby et. al., "Methods for drug screening," the contents of which are hereby incorporated by reference into the present disclosure.

It is to be further appreciated that biological response signals that are suitable for analysis by the methods of the preferred embodiments are not limited to analog signals but can include binary event representations. For instance, in some embodiments, the biological response signal that is measured may be considered a "1" if a cellular constituent which comprises the signal is present in the biological sample and a "0" if it is not present. Thus, using a binary representation, the biological signal data considered by the methods of the preferred embodiments can be derived from expressed sequence tag (EST) approaches (Adams, et al., 1992, Science, 252:1651), RNA blotting, ribonuclease protection and reverse-transcriptase-polymerase chain reaction analysis (Alwine et al., 1977, Proc. Natl. Acad. Sci. U.S.A., 74:5350). As used herein the term "cellular constituent" includes individual genes, proteins, mRNA expressing a gene, and/or any other cellular component that is typically measured in a biological response experiment by those skilled in the art.

Data derived from methods that identify specific genes in a biological sample ("gene identification experiments") are also suitable for the methods of the present invention. In this context, the biological sample may be a cell line that has been incubated under controlled conditions. These controlled conditions may optionally include exposure of the cell line to a perturbation such as increasing concentrations of a pharmacological agent. Alternatively, the biological sample may be tissue obtained from a multicellular organism. Regardless of the type of biological sample utilized, there are a considerable number of experimental methods for identifying specific genes in such biological samples. Typically such experimental methods involve the extraction of the messenger RNA ("mRNA") from the cell line of interest. Complementary DNA ("cDNA") sequences are synthesized by reverse transcription of the extracted mRNA. Then, techniques that utilize specific oligonucleotide probes, which have been designed to selectively hybridize to particular DNA or gene sequences, are used according to the methods of Watson et al. See e.g. Watson et al., Recombinant DNA, chap. 7, W. H. Freemen, New York. For the purpose of obtaining a desirable form of input data for the methods of the present invention, data obtained by gene identification experiments may optionally be represented as binary events. Thus if specific oligonucleotide probes identify a particular gene in a biological sample, such an event may be represented as a "1" whereas the inability to identify a gene of interest in a biological sample may be represented as a "0" or perhaps a "−1". More comprehensive illustrations of gene identification experiments are illustrated in the following paragraphs. One skilled in the art will readily appreciate that if the biological sample is first subjected to a perturbation, these gene identification experiments may be adapted to track differential expression of particular genes within the biological sample.

Often in gene identification experiments, the cDNA obtained from the extracted mRNA may be in the form of an arrayed cDNA library. An arrayed cDNA library is formed by placing the cDNA into vectors that are plated in a manner so that the progeny of individual vectors bearing the clone of one cDNA sequence can be separately identified. Replicas of such plates are then probed with a labeled DNA oligomer that has been selected to hybridize with the cDNA representing the gene of interest. As those colonies bearing the cDNA of interest are found and isolated, the corresponding cDNA inserts are harvested and sequenced by methods such as the Sanger dideoxy chain termination method (Sanger et al., 1977, "DNA sequencing with chain terminating inhibitors", Proc. Natl. Acad Sci. USA 74(12):5463–5467).

The DNA oligomer probes used in colony selection of cDNA libraries are synthesized to hybridize, preferably, only with the cDNA for the gene of interest. One manner of achieving this specificity is to start with the protein product of the gene of interest. If the sequence of a 5 to 10-mer peptide fragment from an active region of the protein product can be determined, corresponding 15 to 30-mer degenerate oligonucleotides that code for this peptide can be prepared. This collection of degenerate oligonucleotides will typically be sufficient to selectively identify the corresponding gene. Similarly, any experimental process that is capable of deriving a 15 to 30 long oligonucleotide gene subsequence can be used to create an oligonucleotide probe that is capable of selectively identifying the gene of interest.

Other types of gene identification experiments search for a known gene in a cDNA or genomic DNA prepared from a biological sample using single gene or single sequence probes that are complementary to unique subsequences of the known gene sequences. For example, the expression of a particular oncogene in biological sample can be determined by probing cDNA derived from the sample with a probe that is designed based on a subsequence of the oncogene's expressed sequence tag. Similarly the presence of a rare pathogen, such as the TB bacillus or the HIV, can be determined by probing gDNA with a hybridization probe specific to a gene of the pathogen. The heterozygous presence of a mutant allele in a phenotypically normal individual, or its homozygous presence in a fetus, can be determined by probing with an allele specific probe complementary only to the mutant allele (See, e.g., Guo et al., 1994, Nucleic Acid Research, 22: 5456–65).

Another class of gene identification experiments include the method of sequencing by hybridization ("SBH"). SBH uses combinatorial probes that are not gene specific (Drmanac et al., 1993, Science 260:1649–52; U.S. Pat. No. 5,202,231, Apr. 13, 1993, to Drmanac et al). An exemplary implementation of SBH to identify a gene requires that a single cDNA clone be probed with all DNA oligomers of a given length, say, for example, all 6-mers. The complete set of all oligomers of a given length synthesized without any further criteria is known as a combinatorial probe library. From knowledge of all hybridization results for a combinatorial probe library, a partial DNA sequence for cDNA clones of interest can be reconstructed. Complete sequences are not determinable because, at least, repeated subsequences cannot be fully determined. SBH adapted to the classification of known genes is called oligomer sequence signatures ("OSS") (Lennon et al., 1991, Trends In Genetics 7(10):314–317). This technique classifies a single clone based on the pattern of probe hits against an entire combinatorial library, or a significant sub-library. It requires that the tissue sample library be arrayed into clones, each clone comprising only one pure sequence from the library. It cannot be applied to mixtures.

In contrast to the gene identification experiments outlined in the preceding paragraphs, another existing experimental technique, known as differential display, involves the "fingerprinting" of a mixture of expressed genes. The mixture of expressed genes may be, for example, a pooled cDNA library obtained from the total mRNA expressed by a biological sample. This fingerprinting seeks merely to distinguish two samples. No attempt is made to determine the quantitative, or even qualitative, expression of particular, determined genes (Liang et al., 1995, Current Opinions in Immunology 7:274–280; Liang et al., 1992, Science 257:967–71; Welsh et al., 1992, Nucleic Acid Res. 20:4965–70; McClelland et al., 1993, Exs 67:103–15; Lisitsyn, 1993, Science 259:946–50). Differential display uses the polymerase chain reaction ("PCR") to amplify DNA subsequences of various lengths, which are defined by being between the hybridization sites of arbitrarily selected primers. Ideally, the pattern of lengths observed is characteristic of the tissue from which the library was prepared. Typically, one primer used in differential display is oligo(dT) and the other is one or more arbitrary oligonucleotides designed to hybridize within a few hundred base pairs of the poly-dA tail of a cDNA in the library. Thereby, on electrophoretic separation, the amplified fragments of lengths up to a few hundred base pairs should generate bands characteristic and distinctive of the sample. Changes in tissue gene expression may be observed as changes in one or more bands. These and other gene identification experiments are more fully described in PCT Publication No. WO 97/15690, "Method and Apparatus for Identifying, Classifying, or Quantifying DNA Sequences in a Sample Without Sequencing," published on May 1, 1997, the contents of which are hereby incorporated by reference into the present disclosure.

The methods outlined in the preceding paragraphs can collectively be termed biological response signal experiments. One skilled in the art will recognize that biological response signal experiments can be coupled based on a perturbation. For example, a pair of biological response signal experiments can be performed using a biological sample. One member of the pair of biological response signal experiments is run before the biological sample is subjected to a perturbation and the second member of the biological response signal experiments is performed after the sample has been subjected to a perturbation. After the pair of biological response signal experiments is run, each cellular constituent tracked by the pair of biological response signal experiments is compared. In one embodiment, this data is compared by representing cellular constituent that were present after introduction of the perturbation as a "1", representing cellular constituents whose presence was not altered by the perturbation in the coupled experiment as a "0", and representing cellular constituent that were present prior but not after the perturbation as a "−1". The reduced biological response signal data may then be analyzed in accordance with the preferred embodiments.

Database server 106 and computational server 107 typically comprise very high powered processors for processing large amounts of data, preferably arranged into a dual processor or multiprocessor systems. A suitable dual processor server may correspond, for example, to a Compaq DIGITAL™ Server 1200 equipped with two Pentium®-II processors, a Sun Enterprise™ 250 Server equipped with two UltraSPARC™-II processors, or a Compaq Alphaserver™ GS140 Server equipped with dual Alpha 21264 processors. A suitable multiprocessor server having four or more processors may correspond, for example, to a Compaq DIGITAL™ AlphaServer 8400 or a Sun Enterprise™ 10000 Server. Database server 106 will typically also comprise large, high performance storage media for data storage.

Database server 106 and computational server 107 each include an operating system such as UNIX or Windows® NT, along with hardware and software necessary to achieve a data communications interface with user computer 108, scanning device 104, remote scanning device 114, remote user computer 116, and generally any computer that is coupled to the Internet 112 using any of the communication protocols discussed supra. In a preferred embodiment, the database server 106, the computational server 107, the data network 102, and the gateway computer 110 are adapted to communicate with Internet 112 users using a TCP/IP protocol.

Database server 106 serves as the host site for a relational database management system for storing and retrieving biological data in accordance with a preferred embodiment. A database management system is a software program that typically operates on a database server or mainframe system to manage data, accept queries from users, and respond to those queries. A typical database management system is capable of: providing a way to structure data as records, tables, or objects; accept data input from operators and store that data for later retrieval; provide a query language for searching, sorting, reporting, and other decision support activities that help users correlate and make sense of the collected data; providing multi-user access to the data, along with security features that prevent some users from viewing and/or changing certain types of information; providing data integrity features that prevent more than one user from accessing and changing the same information simultaneously; and providing a data dictionary that describes the structure of the database, related files, and record information.

Most database management systems, such as that hosted by database server 106, are client/server based and operate over networks. In the embodiment of FIG. 1, the server is the database server 106, whereas the clients include user computers 108 and 116, as well as scanning devices 104 and 114. Database management systems include an engine that runs on a powerful server with a high-performance channel to the large data store. The database server 106 system accepts requests from the clients that may require sorting and extracting data. Once the database server 106 has processed the request, it returns the information to the client. The common language for accessing most database systems is SQL (Structured Query Language). In a preferred embodiment, database server 106 uses an Oracle database management system that operates responsive to SQL queries.

Although within the scope of the preferred embodiments, flat-file database systems are not recommended for use in biological response data network 100. Flat-file databases are generally applicable to simple data systems, since all the information can be stored in one file. Flat-file databases are generally inadequate for complex database applications such as that of biological response data network 100. Rather, relational database systems and/or object-oriented database systems are more appropriate for the biological response data network 100. A relational database management system in accordance with the preferred embodiments is a system that stores biological data in multiple tables. The tables can be related and combined in a number of ways to correlate and view the data. A typical database for a biological analysis system might contain hundreds of tables that can potentially produce thousands of relationships. A common element, such as a scan ID or a gene ID, may link information across the tables. A query for a particular scan, for example, may pull the scan date from a first table, the involved genes from a second table, the perturbation types from a third table, and so on.

Object-oriented databases, which are also within the scope of the preferred embodiments, generally include the capabilities of relational databases but are capable of storing many different data types including images, audio, and video. Additionally, object oriented databases are adapted to store methods, which include properties and procedures that are associated with objects directly in the database. A variety of references are publicly available for further information on implementing relational and/or object oriented databases for enabling the implementation of the systems and methods disclosed herein; see, for example, Cassidy, *High Performance Oracle8 SQL Programming and Tuning*, Coriolis Group (March 1998), and Loney and Koch, *Oracle 8: The Complete Reference (Oracle Series)*, Oracle Press (September 1997), the contents of which are hereby incorporated by reference into the present disclosure.

User computer 108 comprises a computing device or workstation capable of implementing biological response analysis software in accordance with a preferred embodiment. User computer 108 may correspond, for example, to a personal computer having a Pentium®-II processor and a Windows® NT Workstation operating system, to a Sun workstation having a SPARC processor and a UNIX operating system, or other similar systems. Although the scope of the preferred embodiments is not so limited, user computer 108 is generally not required to have computing power comparable to that of database server 106, although it is preferable for user computer 108 to have a high degree of graphics capability for displaying multiple graphical windows to the user. Remote user computer 116 is similar but is also adapted to communicate with database server 106 over the Internet 112 using, for example a TCP/IP protocol as disclosed supra. Although the scope of the preferred embodiments is not so limited, a typical biological response data network 100 will comprise a plurality of user computers 108 and a plurality of remote user computers 116 for each such database server 106. Thus, many users may simultaneously perform analysis on the biological response data stored in database server 106.

Figure 3:
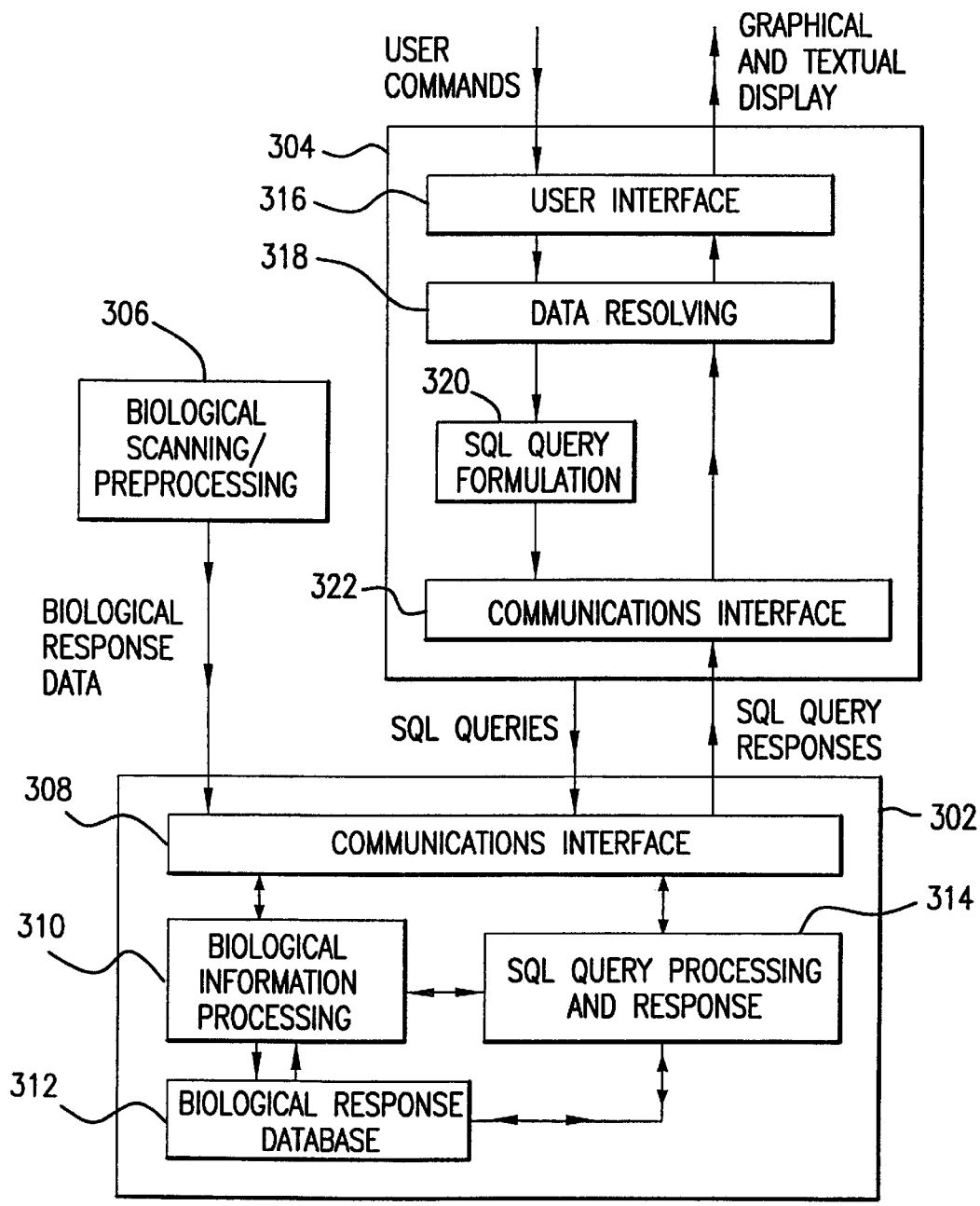
FIG. 3 shows a block diagram corresponding to three primary software elements of a biological response data network in accordance with a preferred embodiment.

FIG. 3 shows a block diagram corresponding to three primary software elements of the biological response data network 100, in particular software corresponding to the scanning device 104, the database server 106, and the user computer 108. More specifically, FIG. 3 shows biological database software 302 corresponding to the database server 106, biological response analysis software 304 corresponding to the user computer 108, and scanning/preprocessing software 306 corresponding to scanning device 104. For simplicity and clarity of disclosure, the function of the computational server 107 is integrated into the database server 106 for the purposes of FIG. 3, although it is to be understood that the scope of the preferred embodiments extends to systems that may separate their respective functions into different hardware systems. Importantly, it is to be appreciated that while the software elements of FIG. 3 are shown corresponding to separate computing devices, any or all or their functionality may be carried out in fewer devices, e.g. a single computer system, or in a far greater number of distributed devices having dedicated computers or even application specific integrated circuits (ASICs) for each specific function, without departing from the scope of the preferred embodiments.

FIG. 3 shows biological scanning/preprocessing software 306 as comprising a single block. Using methods known in the art, biological scanning/preprocessing software 306 performs the steps of (a) directing the physical scanning apparatus to read the scans into image files and/or other primary data, (b) processing part or all of the biological response data, and (c) transferring the biological response data including image files and/or other primary data to database server 106.

FIG. 3 shows biological database software 302 as comprising a communications interface module 308, a biological information processing module 310, a database 312, and a SQL query processing/response module 314. Communications interface module 308 coordinates data transfer between the database server 106 and the scanning device 104 for receiving biological response information. Communications interface module 308 also coordinates data transfer in the form of SQL database queries and responses between the database server 106 and the user computer 108. Biological information processing module 310 processes as necessary any biological information that was not already preprocessed by the biological scanning/preprocessing software 306 such that the requisite data is in appropriate form for storage in database 312 or distilled for presentation by biological response analysis software 304. For example, as described further infra, biological information processing module 310 may precompute correlation coefficients among all pairs of experiments being loaded into the database, or automatically group repeated experiments together based upon information in the database. In accordance with a preferred embodiment, database 312 is a set of tables and/or other data objects stored in accordance with the Oracle 8® database management system. Finally, SQL query processing and response module 314 handles SQL queries received from the user computer 108, searches the database 312, and provides responses for communication back to user computer 108. Depending on the query type, this may involve the invocation of further processing by biological information processing module 310.

FIG. 3 also shows biological response analysis software 304 in accordance with a preferred embodiment, which is installed on user computer 108 and a plurality of other user computers in biological response data network 100. As shown in FIG. 3, biological response analysis software 304 comprises a plurality of functional modules including a user interface module 316, a resolving module 318, an SQL query module 320, and a communications module 322.

Advantageously, according to a preferred embodiment, biological response analysis software 304 is written in the Java programming language, thus allowing for platform independence such that it may be executed on any of a variety of user computers 108 and remote user computers 116 having different operating systems. As known in the art, Java is a programming language optimized for cross-platform, object-oriented, distributed, multithreaded computing, which is particularly advantageous in view of the functionality of biological response analysis software 304. Information on Java programming may be found, for example, in Ritchey, *Java!*, New Riders Publishing (1995), and Lemay, Perkins, and Morrison, *Teach Yourself Java in 21 Days: Professional Reference Edition,* Sams.net Publishing (1996), the contents of both of these references being hereby incorporated by reference into the present application.

User interface module 316 comprises software for driving a menu-driven, multi-window graphical interface for allowing the user to easily manipulate and analyze data in oner or more viewer windows. In a preferred embodiment, the user interface module 316 is adapted to provide the look and feel of an Internet browser interface, a Windows® 95 interface, or an X-Windows type interface. Resolving module 318 comprises software for coordinating data presentation among multiple windows, processing search parameters, performing statistical analysis, projecting biological datasets, and other routines within biological response analysis software 304 in accordance with the preferred embodiments. SQL query module 320 comprises software for formulating SQL queries compatible with the Oracle 8® based database 312 responsive to the data requirements of biological response analysis software 304. Communications interface module 322 comprises software for transmitting SQL queries to database server 106 containing the database 312 and for receiving responses therefrom.

It is to be appreciated that the specific programming structure of biological response analysis software 304 may vary significantly, but in all cases is enabled by the present disclosure, it being understood that one skilled in the art will be readily capable of implementing the preferred embodiments given the present descriptions and the referenced works. It is to be further appreciated that, as necessary infra to clearly describe the preferred embodiments, hypothetical biological examples may be used instead of actual biological materials, e.g. "Gene X", "Gene Y", "Drug A", etc.

FIG. 4 shows a query composition and results display window 400 corresponding to biological response analysis software 304 in accordance with a preferred embodiment. In the example of FIG. 4 the biological response analysis software 304 is adapted for analysis of gene or protein expression data, although the scope of the preferred embodiments is not so limited and may include software for analyzing any type of biological experiment configuration that produces machine readable signals. Query composition and results display window 400 comprises an experiments tab 402, a scans tab 404, a biosets tab 406, and a genes tab 408 which, although used for searching among different groupings of expression array data, present similar search interfaces to the user when selected.

Query composition and results display window 400 comprises, within the currently active experiments tab 402, scans tab 404, biosets tab 406, or genes tab 408, as the case may be, an alphanumeric data display area 409 for displaying the selected set of experiments, scans, biosets, or genes. Data is generally listed in column format, the columns being adjustable and scrollable. It is to be appreciated that the data area 409 of FIG. 4, while showing several fields including Chip Barcode, Hyb Name (i.e. the type of perturbation), Scan Date, Analysis Date, Mean Sig/Bkgd, Sample (G), and Sample (R), may contain many different sets of fields as determined by the contents of biological response database 318, and may be right-scrollable for showing many more fields.

Generally speaking, the scans tab 404 is used to search for primary expression data from individual hybridizations, i.e., readings from individual experimental perturbations. The experiments tab 402 is used to search for combined sets of scans derived from analysis of repeated hybridizations. The genes tab 408 is used to search for genes contained in the biological response database 312, which may include any arrayed substances including controls, PCR products, genomic data, and the like. Finally, the biosets tab 406 is used to search for collections of experiments or genes. Basic searching is performed by (a) selecting a search criteria item from the search criteria menu 410, (b) selecting a search condition from the search condition menu 412, (c) selecting or entering search values into search value field 414, and (d) pressing the execute launch button 415. The experiments, scans, biosets, or genes in biological response database 312 that match the search criteria appear in the alphanumeric data display area 409.

In general, and as will be further described herein, in a preferred embodiment the user operation of biological response analysis software 304 involves a first step of selecting a single set or a plurality of sets of experiments, scans, or genes by a query process similar to the above basic search process. Following this step, a second step may be performed wherein selected data is viewed using one or more biological viewers. An exemplary set of basic biological viewers includes an expression image biological viewer, a signature plot biological viewer, a table biological viewer, and a statistics biological viewer. Following this step, a third step may be performed wherein a subset of data being displayed on one of the biological viewers is selected and projected onto other active biological viewers for further user analysis, the subset being identified based on a search for datapoints meeting specific conditions and/or based on other identification procedures. Depending on nature of the analysis that is being performed, useful results may occur after any of the above steps. Generally speaking, the above steps will be iteratively performed by the user whose biological research, including the search for biological pathways, is enhanced through the use of the biological response analysis software 304.

Alternatively or in conjunction with the above steps, an additional step of comparing several experiments, scans, or genes may be performed using a biological comparison algorithm (e.g., "ROAST") and biological viewers associated therewith. An exemplary set of biological viewers associated with the biological comparison algorithm (e.g., ROAST) includes a correlation plot viewer. Finally, either alternatively or in conjunction with all of the above steps, a further additional step of forming defined biological sets may be performed in conjunction with the use of still other biological viewers. An exemplary set of biological viewers associated with the analysis of defined biological sets includes a trend biological viewer and a cluster tree or gene coregulation tree biological viewer.

Query composition and results display window 400 further comprises a plot launch button 416 that is functional when the experiments tab 402, scans tab 404, or genes tab 408 is active. In particular, when pressed by the user, the plot launch button 416 launches a signature plot biological viewer, a software routine that creates a separate display window showing a signature plot for the selected experiment or scan, or gene.

Figure 5:
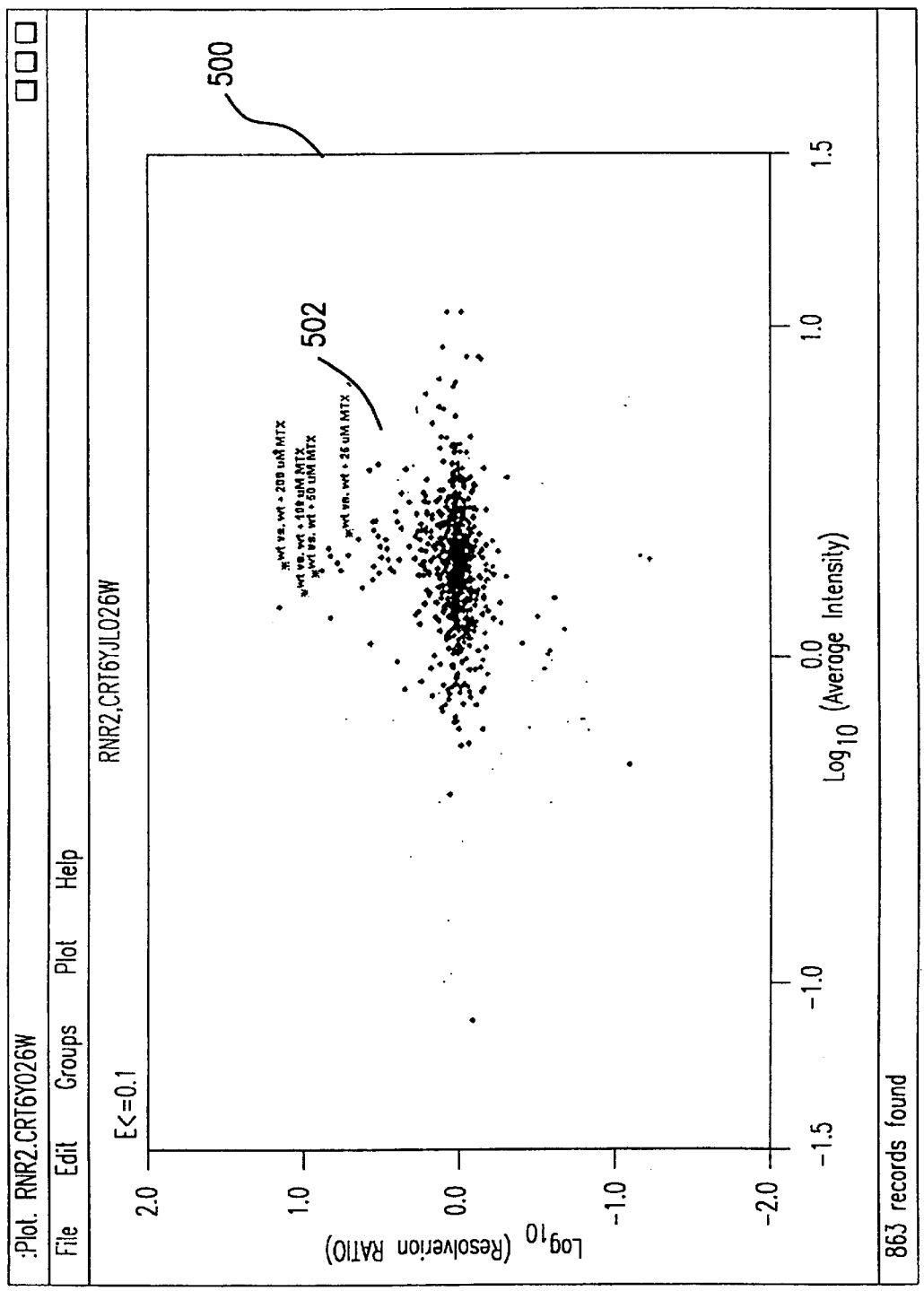
FIG. 5 shows a signature plot biological viewer in accordance with a preferred embodiment.

FIG. 5 shows a signature plot viewer 500 in accordance with a preferred embodiment. Signature plot viewer 500 appears in a separate window than the query composition and results display window 400 when launched. While signature plot viewer 500 is shown in FIG. 5 as plotting the base-10 logarithm of expression ratio versus the base-10 logarithm of intensity, many different scales may be used. At the selection of the user, gene labels may activated on the display for viewing one or more specific gene names. One such label 502 appears in FIG. 5 as an example. Further options are made available to the user for more optimal display of the signature plot viewer 500. As a nonlimiting example, the user is permitted to enter commands that highlight groups of genes (upregulated, downregulated, signature, controls, flagged spots, or a custom set) in a particular color, for example, genes with a p-value less than 0.1 and a log(expression ratio) greater than 0 could be highlighted in the color red. As a further nonlimiting example, the user may enter commands that highlight all upregulated genes above, for example, 0.5, in the color red, and all downregulated genes below, for example, −1.0, in the color green for easier viewing.

With reference to FIG. 4, query composition and results display window 400 further comprises a table launch button 418 that is functional when the experiments tab 402, scans tab 404, or genes tab 408 is active. The table launch button 418 launches a table biological viewer, a software routine that creates a separate display window (not shown) showing alphanumeric data in spreadsheet format corresponding to the selected experiment, scan, or gene.

Query composition and results display window 400 further comprises an info launch button 422, which is functional when any of the experiments tab 402, scans tab 404, biosets tab 406, or genes tab 408 is active. The info launch button 422 invokes a statistics biological viewer (not shown) for viewing vital statistics for the selected experiment, scan, bioset, or gene. As an example, vital statistics for a selected experiment or scan may include quality information.

From the scans tab 404, an image launch button (not shown) may be executed by the user. The image launch button invokes an image biological viewer for viewing an image of the primary biological signal data, e.g., the expression microarray as taken by scanning device 104, along with other data.

Figure 6:
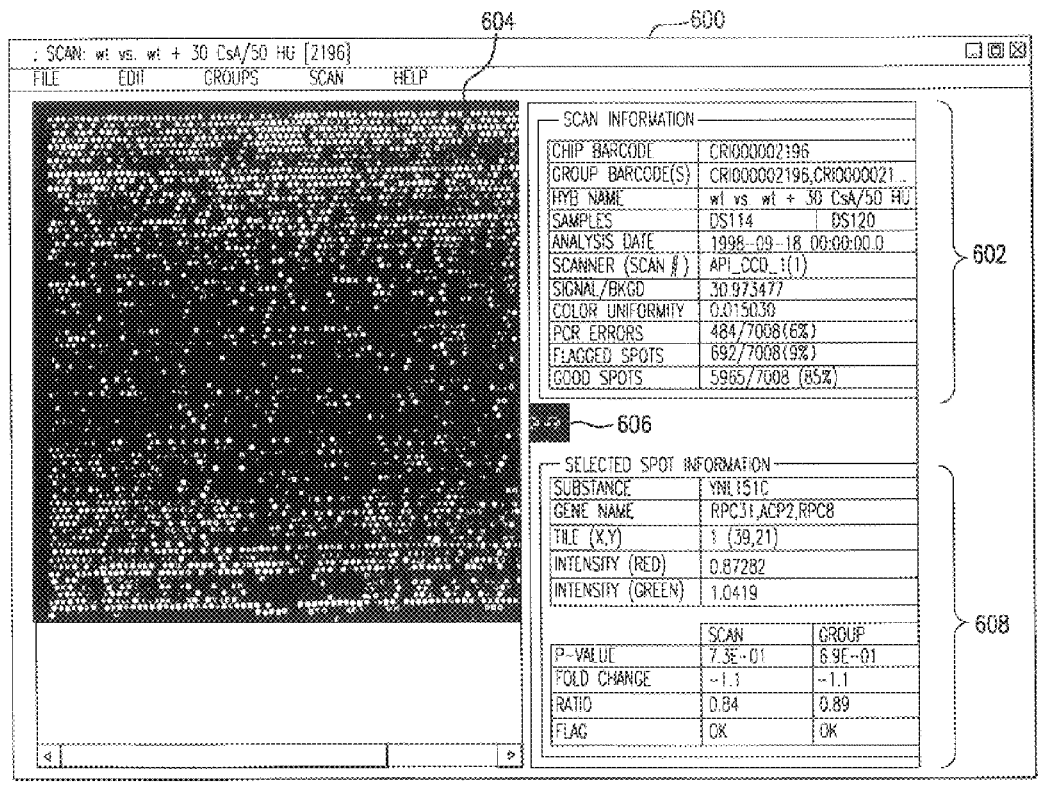
FIG. 6 shows an image biological viewer in accordance with a preferred embodiment.

FIG. 6 shows an scan image 600 corresponding to an image viewer in accordance with a preferred embodiment.

As shown in FIG. 6, a scan information panel 602 on the right hand side of the display shows critical statistics for the scan including computed quality statistics, while the JPEG image 604 for the scan is shown at the left of the display. As known in the art, JPEG image 604 shows hundreds or thousands of spots, each corresponding to an individual gene. In accordance with a preferred embodiment, the image viewer includes the ability for the user to select an individual spot with a mouse button, which will then be shown in an enlarged spot image 606 as shown in FIG. 6. A spot information panel 608 displays critical statistics for that spot, including the p-value, fold-change, and other critical statistics known in the art.

Query composition and results display window 400 further comprises a biological comparison algorithm launch button (e.g., "ROAST") 424 that is functional when the experiments tab 402, scans tab 404, or genes tab 408 is active. A biological comparison algorithm in accordance with a preferred embodiment allows the user to search and compare experiments, scans, or genes to each other in the biological response database 318.

Generally speaking, the biological comparison algorithm permits comparison of experiments to experiments, scans to scans, or genes to genes in a variety of advantageous manners. For example, with respect to experiments, the biological comparison algorithm enables the user to perform the steps of (a) searching the biological response database 318 for correlated response profiles, (b) obtaining a listing of similar response profiles prioritized by degree of correlation (correlation coefficient, p-value, or other similarity metric), and (c) viewing a correlation plot of two such experiments.

Regarding step (a), the search for correlated experiments begins when the user identifies a "query" biological response profile. The query may correspond to any profile of particular interest to the user, e.g., an experiment involving a cellular perturbation with a specific concentration of drug X. The user identifies the query by performing one or more searches using the query composition and results display window 400, selecting a query response profile, then pressing the a biological comparison algorithm ("ROAST") launch button 424.

Following the selection of the source set of experiments resulting from the query response profile, the user again presses the biological comparison algorithm launch button ("ROAST") 424. A wizard window resembling a search window then appears (not shown), allowing the user to select a target set of experiments. The target set of experiments may be as broad as the entire biological response database 312, or may be a specific target set, such as experiments involving cellular perturbations with various concentrations of drugs W, Y, and Z. Advantageously, in a biological comparison algorithm in accordance with a preferred embodiment, several such searches may be performed, the results being added to a shopping cart after each search, the final contents of the shopping cart being used as the target set.

Following the selection of the source sets and target sets, a correlation execution launch button (e.g., "FINISH") is then pressed. The biological comparison algorithm then searches for profiles within the target set that are similar to the query profile by comparing similarity metrics among the pairs, then sorting the result list using the similarity metrics (e.g., correlation coefficients) between experiments in the respective source and target sets. A NEXT button may optionally be pressed to "refine" the search. The user can select genes within an experiment profile or experiments within a gene profile for use in the computation of similarity metrics such as the correlation coefficient. If this step is skipped, all data points in the profiles will be used for the comparison.

Advantageously, in accordance with a preferred embodiment, the correlation coefficients between experiments are precomputed, that is, computed at a prior time nearer to a time when the experiments were first loaded from the scanning device 104 into the biological response database 312. The correlation coefficients are precomputed using methods known in the art and stored along with the experiment data in biological response database 318. While the correlation coefficients are usually scalar numbers between 0.0 and 1.0, correlation data may alternatively comprise correlation matrices, p-values, or other similarity metrics in accordance with the preferred embodiments. Significant time savings may be attained by precomputing the similarity metrics at a prior time, as there is no need for real time "on the fly" computation of the correlation coefficients by the user computer 108 after the correlation execution launch button ("FINISH") is pressed.

Regarding step (b) above for viewing an ordered list of correlations between the query profile and each of the target profiles, the search results in a preferred embodiment can be displayed in columns, usually ordered from highest to lowest correlation coefficient. Regarding step (c), the user may then select any target match listed therein, and then select a correlation plot launch button to spawn a correlation plot biological viewer.

Figure 7:
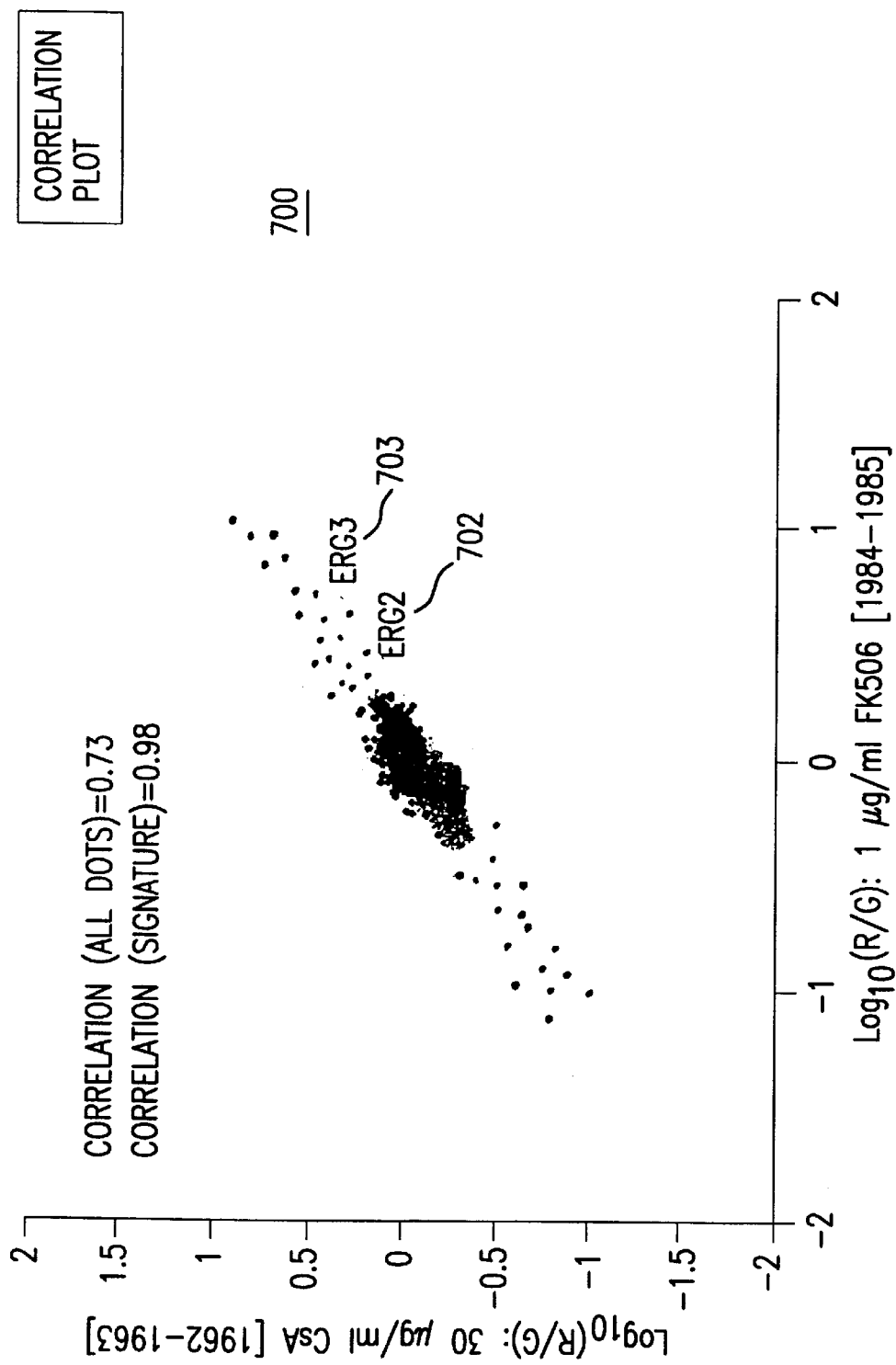
FIG. 7 shows a correlation plot biological viewer in accordance with a preferred embodiment.

FIG. 7 shows a correlation plot viewer 700 in accordance with a preferred embodiment. As with all viewers in a preferred embodiment, correlation plot viewer 700 appears in a separate window than the query composition and results display window 400 when launched, and also in a window separate from any other active biological viewer such as the signature plot viewer 500 supra. Each gene common to the two experiments is plotted on the correlation plot viewer 700 at a vertical axis location corresponding to its expression ratio or another measure of biological signal response in the first experiment (30 $\mu$g/ml CsA in the example of FIG. 7) and at a horizontal axis location corresponding to its expression ratio or another measure of biological signal response in the second experiment (1 $\mu$g/ml FK506 in the example of FIG. 7). While the correlation plot viewer 700 is shown in FIG. 7 as plotting the base-10 logarithm of expression ratios, many different scales or biological signal response measurements may be used. As is generally the case with all biological viewers disclosed herein, datapoint labels (e.g., gene or experiment) may be activated on the display for viewing one or more specific gene names, two such labels 702 and 704 appearing in FIG. 7. As with the signature plot viewer 500 of FIG. 5, several display options are available to the user for optimal viewing, such as color highlighting of genes that are significantly upregulated for both experiments.

Query composition and results display window 400 further comprises a bioset launch button 420, which is functional when the experiments tab 402 or genes tab 408 is active. When pressed by the user, bioset launch button 420 launches a software routine for creating, managing, and viewing biosets, that is, collections of experiments, genes, or other biological reagents. Biosets can be created for any of a variety of relationships among genes or experiments, such as members of a titration curve or other sets of experiments that may be of interest to the user. The biosets tab 420 contains data from gene and experiment clustering experiments, as well as other "ExperimentSets" or "GeneSets" that may be built by the user using intuitive menu-driven commands from within the experiments tab 402 or genes tab 408, respectively.

Figure 8:
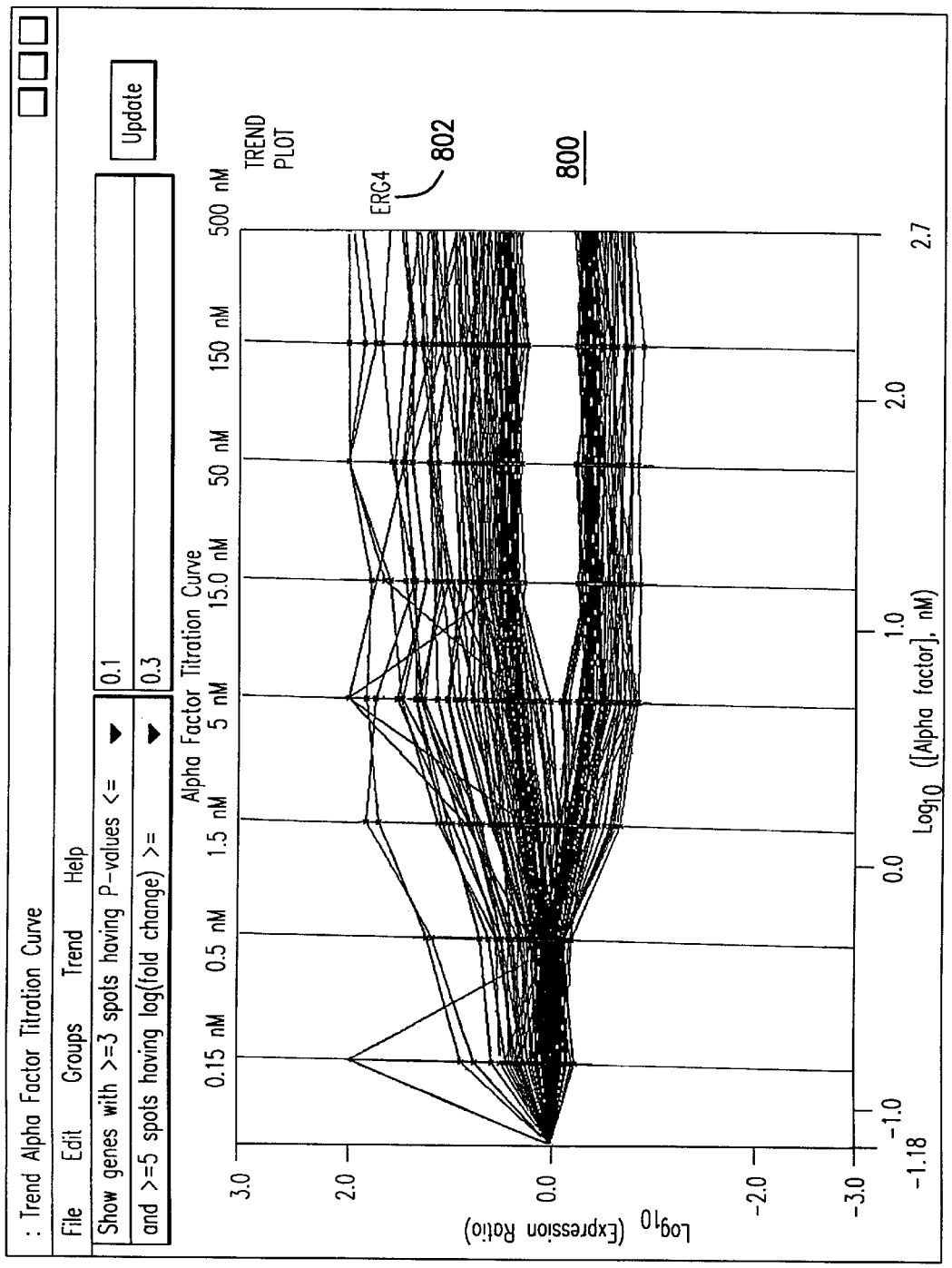
FIG. 8 shows a trend plot biological viewer in accordance with a preferred embodiment.

FIG. 8 shows a trend plot viewer 800 in accordance with the preferred embodiments. The trend plot biological viewer 800 is spawned from within the biosets tab 420 upon user selection of an experiment set and pressing of a trend plot launch button (not shown). As known in the art, trend plot viewer 800 comprises a set of titration curves for a set of genes, where the expression ratios are plotted for each gene versus a successively changing perturbation amount (Alpha factor concentration in FIG. 8). As with other biological viewers disclosed herein, datapoint labels may activated on the display for viewing one or more specific gene names, one such label 802 appearing in FIG. 8. As with the signature plot viewer 700 of FIG. 7, several display options are available to the user for optimal viewing, such as color highlighting of genes that are significantly upregulated or downregulated as the intensity of the perturbation factor increases.

Figure 9:
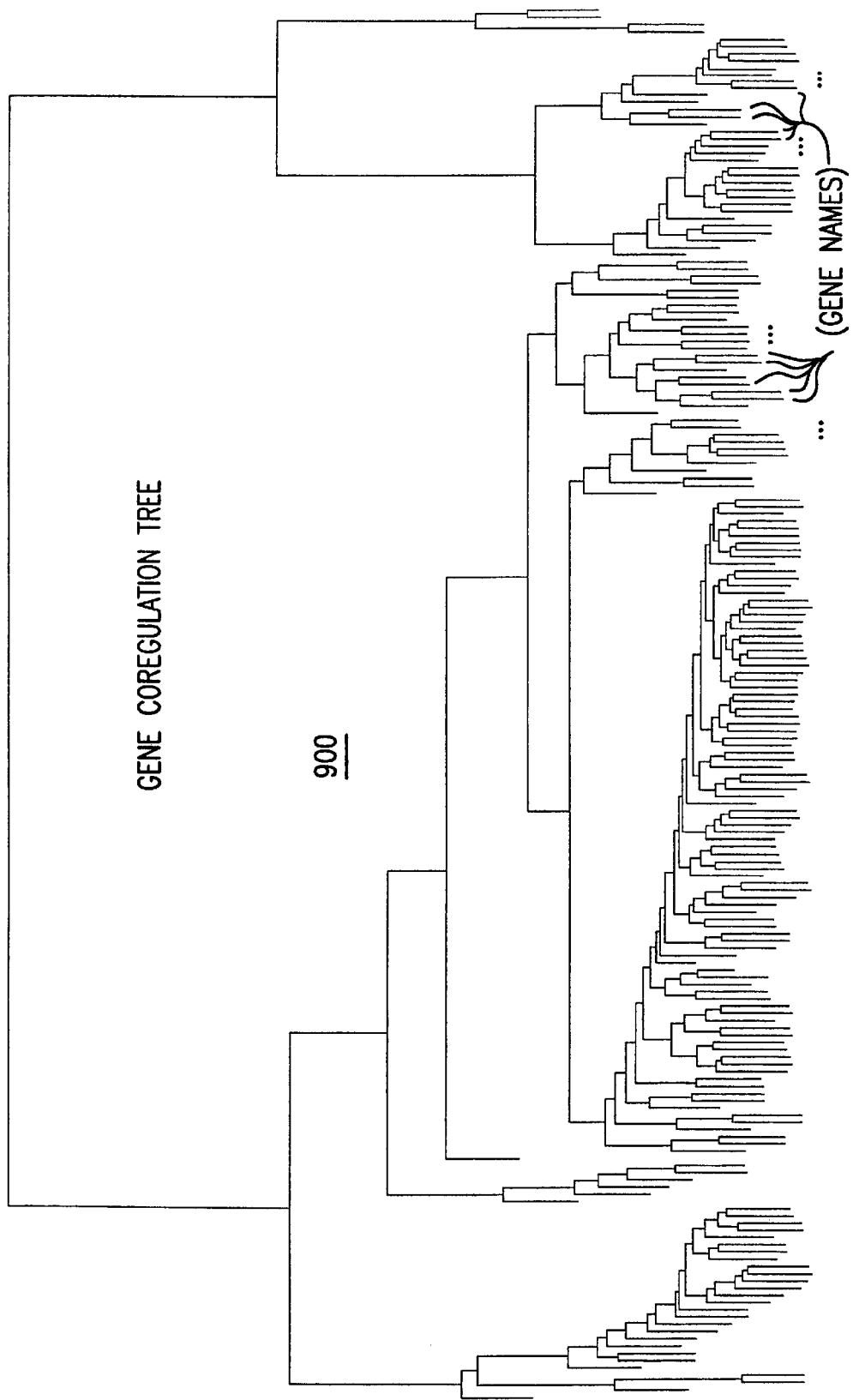
FIG. 9 shows a biological response profile cluster tree.

FIG. 9 shows a biological response profile cluster tree 900 in accordance with the prior art. More specifically, FIG. 9 shows a gene coregulation tree, which corresponds to one type of biological response profile cluster tree. Using data obtained from multiple experiments on a set of genes, a gene coregulation tree may be constructed using methods known in the art for cluster analysis, grouping genes based upon commonality of gene responses to various biological perturbations. Generally speaking, response profiles that are highly similar to one another will be close together within the cluster tree, and significantly different profiles will be farther apart. Each gene eventually populates its own "leaf" on the end of the coregulation tree. Increasing distance between upstream nodes in common to two genes (profiles) is indicative of more significant dissimilarity between those two genes (profiles).

The prior art cluster tree 900 presents difficulties to computer users in analyzing its structure on a computer monitor. In particular, the lateral separation of branches in a single direction (the horizontal direction in FIG. 9) causes excessive crowding of lower branch nodes and a loss of perspective when zooming. For example, when zooming in on a lower level "outer" branch in a computer display of FIG. 9, the user quickly loses perspective of the big picture, i.e. where they are with respect to higher level nodes and to the origin or "root node" of the tree.

Figure 10:
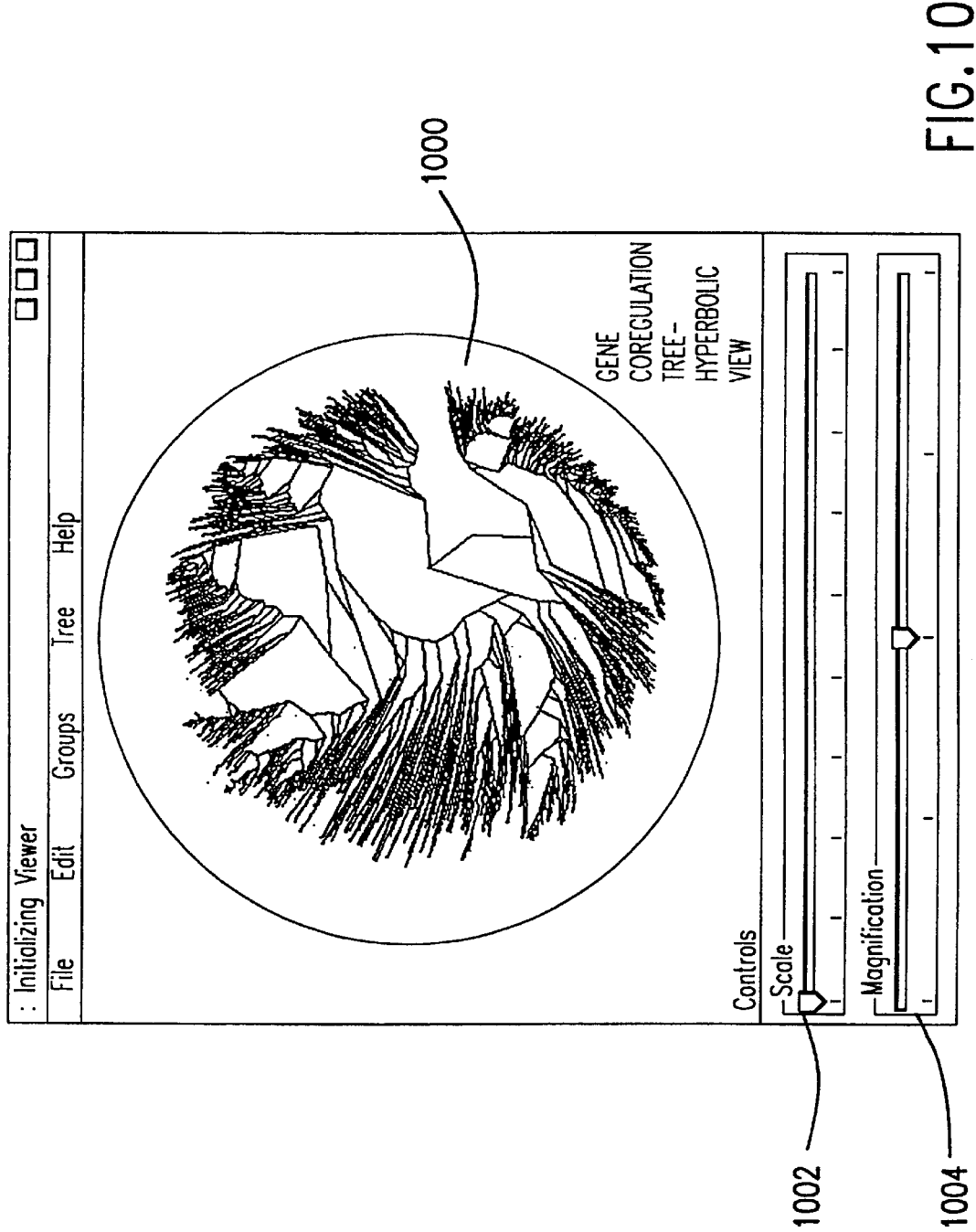
FIG. 10 shows a cluster tree biological viewer in accordance with a preferred embodiment.
Figure 11:
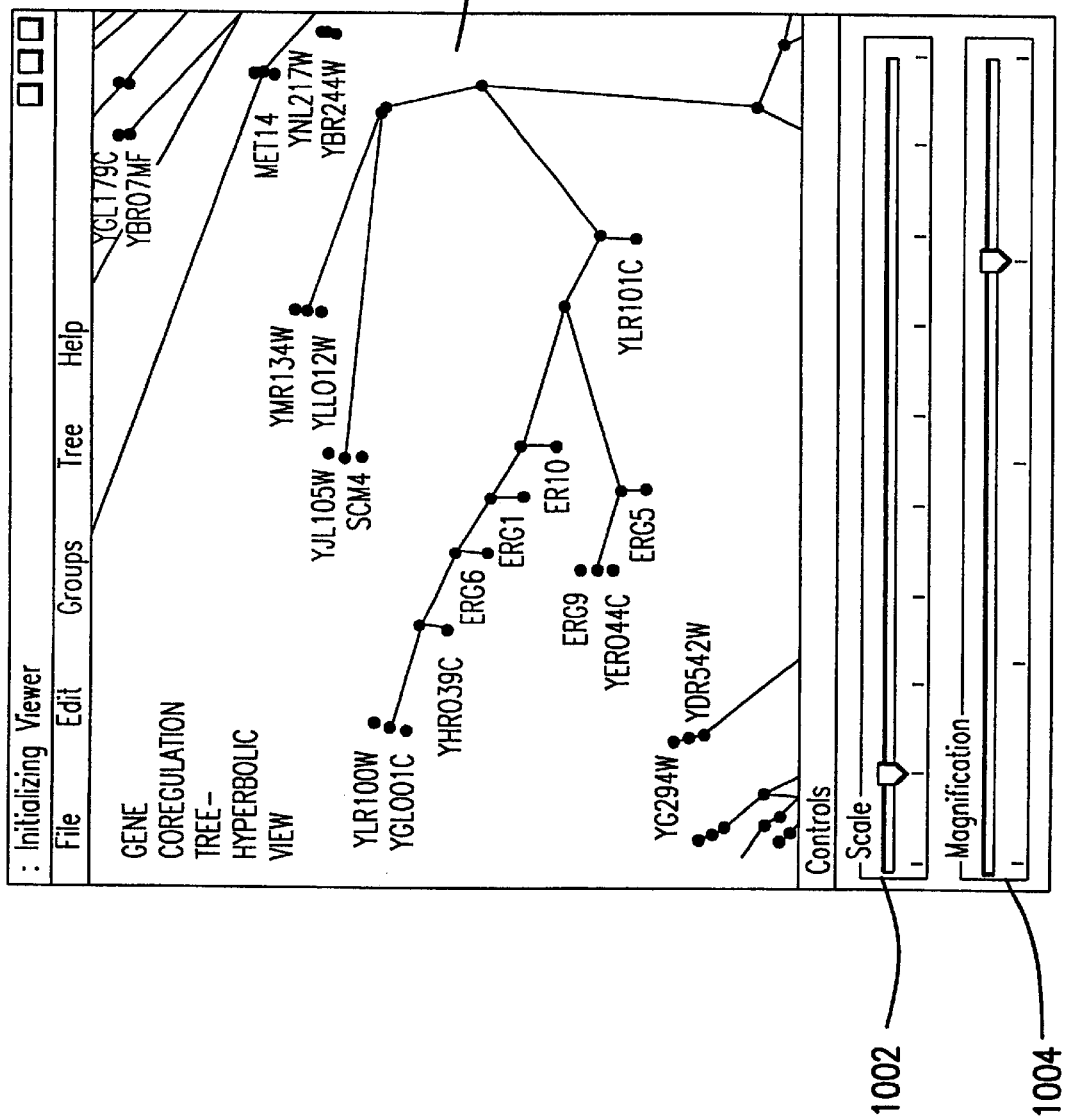
FIG. 11 shows the cluster tree biological viewer of FIG. 10 at a different magnification and scale.

FIGS. 10 and 11 show computer display outputs of a cluster tree biological viewer in accordance with the preferred embodiments. The cluster tree biological viewer is launched from within the biosets tab 420 upon user selection of an ExperimentSet or GeneSet and the pressing of a tree plot launch button (not shown). In accordance with a preferred embodiment, a cluster tree is first computed using methods known in the art, and then adapted for display in a hyperbolic display format. By hyperbolic display format, it is meant that the gene coregulation tree appears on the computer screen as if it has been mapped according to a hyperbolic mapping function. As shown in FIGS. 10 and 11, the specific hyperbolic mapping function used may be regulated by a user-selectable scale input 1002 and a user-selectable magnification input 1004.

Figures 20A, 20B:
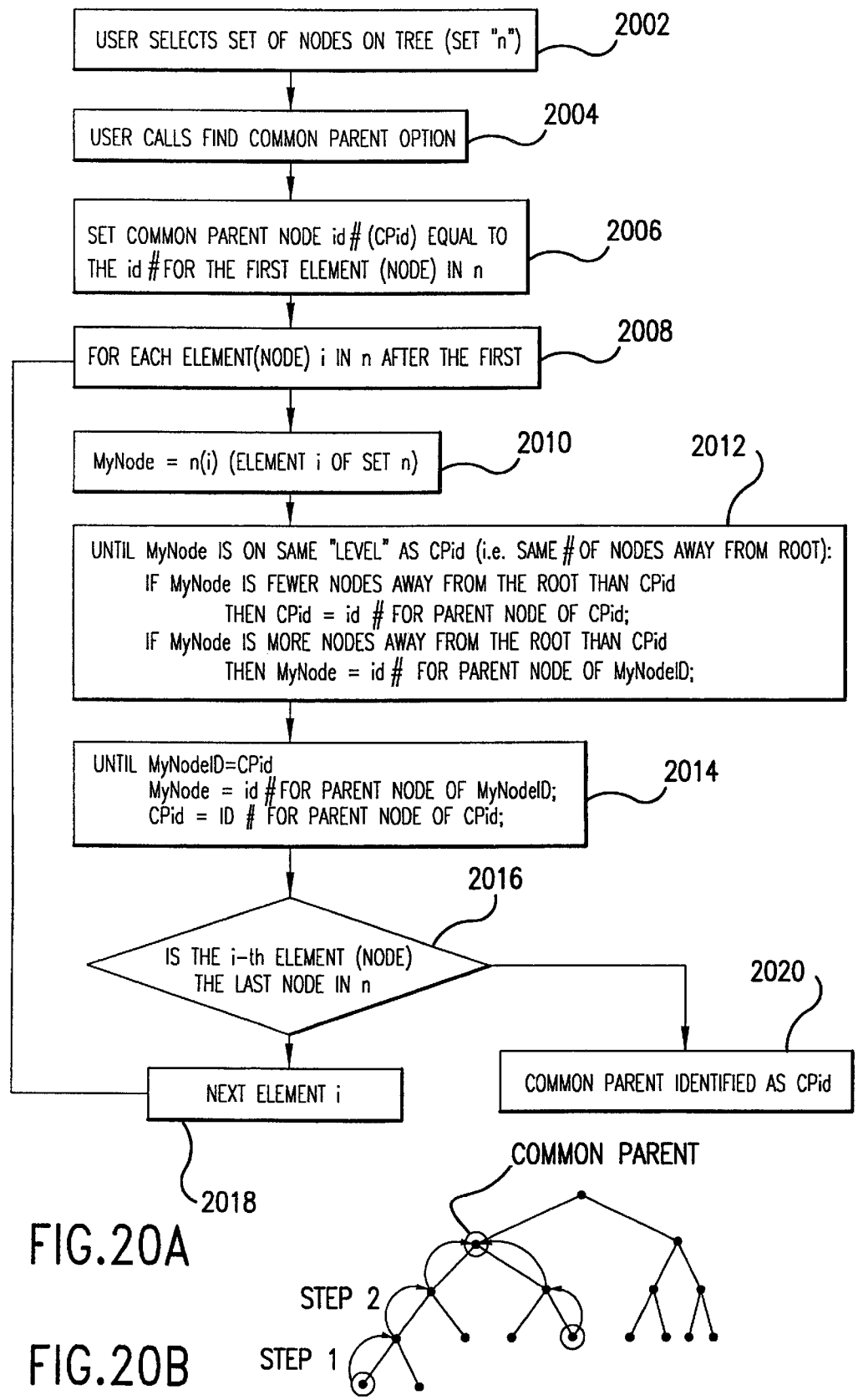
FIG. 20 shows steps for finding the common parent node of two biological signal profiles on a hierarchical cluster tree in accordance with a preferred embodiment.

Advantageously, the hyperbolically displayed gene coregulation trees shown in FIGS. 10 and 11 provide for convenient viewing of specific locations on the gene coregulation tree, without losing perspective of where the user is looking relative to the branches nearer to the "root" of the tree. As shown in FIG. 11, even at very close magnification near the specific genes ("leaves"), there is an immediate sense to the user as to the location of the center of the tree. As with other biological viewers disclosed herein, gene labels may activated on the display for viewing one or more specific gene names and several display options are available to the user for optimal viewing. For example, in a preferred embodiment, the user may hold the shift key down, and then click-and-drag using the mouse to rotate the tree about the "root" node. In a preferred embodiment, the user may invoke a "find common parent" algorithm to identify the parent node in common to all currently selected profiles (genes or experiments), one such algorithm being illustrated and explained by FIG. 20.

Advantageously, hyperbolic displays similar to those of FIGS. 10 and 11 may be utilized for analyzing expression array data using the steps of (a) generating a coregulation tree using expression array data, (b) displaying the coregulation tree in a hyperbolic display format, (c) manipulating the display of the coregulation tree to display a first gene or gene product located on a branch thereof, the first gene or gene product having a known function, (d) locating a second gene or gene product on the coregulation tree on the same branch as the first gene or gene product, and (e) assigning a function to the second gene or gene product using information related to the known function of the first gene or gene product and information related to a positional relationship or distance metric between the second gene or gene product and the first gene or gene product on the branch of the coregulation tree. Assignment of function includes, but is not limited to, the identification of new drug targets by starting with known drug targets on the tree. Given one or more known successful drug targets, this technique allows the identification of new prospective drug targets involved in the same cellular pathway or process based on their positional relationship with known targets on the cluster tree (or distance metric between them).

In another preferred embodiment, hyperbolic displays similar to those of FIGS. 10 and 11 may be utilized for analyzing expression array data using the steps of (a) generating an experiment profile cluster tree using the expression array data, (b) displaying the experiment profile cluster tree in a hyperbolic display format, (c) manipulating the display of the experiment profile cluster tree to display a first experiment located on a branch thereof, the first experiment corresponding to a known function of a perturbation assayed therein, (d) locating a second experiment on the experiment profile cluster tree on the same branch as the first experiment, and (e) assigning a function to a biological perturbation assayed in the second experiment using information related to the known function of the perturbation assayed in the first experiment and information related to a positional relationship or distance metric between the second experiment and the first experiment on the branch of the experiment profile cluster tree. Assignment of function includes, but is not limited to, the identification of new drug targets by starting with known drug targets on the tree. Given one or more known successful drugs or drug target deletion profiles, this technique allows the identification of similar profiles that represent new prospective drugs or drug targets affecting or involved in the same cellular pathway or process.

Figure 12:
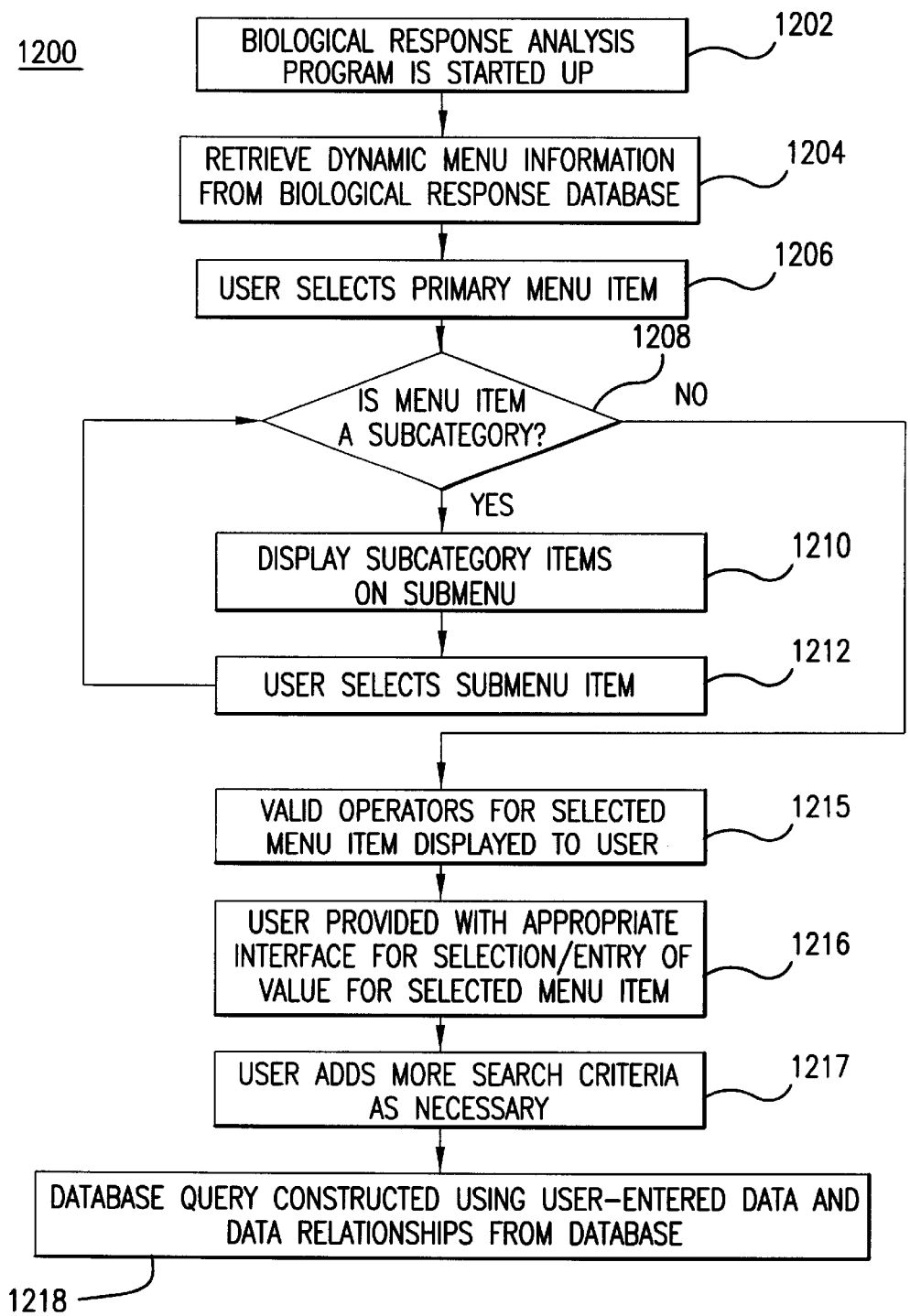
FIG. 12 shows a flowchart of a dynamic biological menu generation algorithm in accordance with a preferred embodiment.
Figure 13:
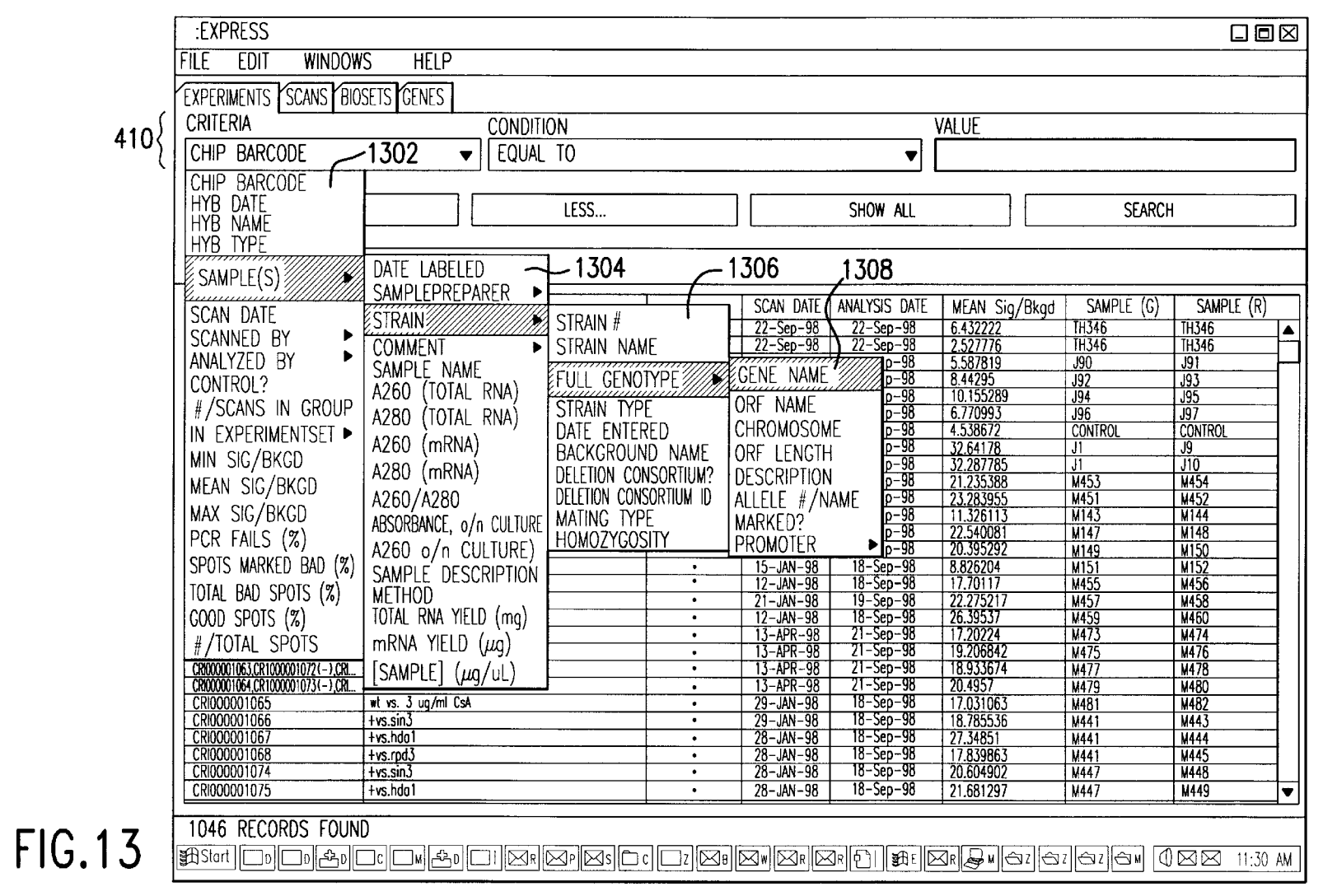

FIG. 12 shows a flowchart of a dynamic biological menu generation algorithm 1200 in accordance with a preferred embodiment. FIG. 13 shows the query composition and results display window 400 with the criteria menu 410 expanded to illustrate the steps 1200 of FIG. 12. As shown in FIG. 13, the criteria menu 410 comprises a primary menu 1302 and a series of submenus, some of which are shown as submenus 1304, 1306, and 1308. The user activates the primary menu 1302 by clicking in the relevant space directly under the "Criteria" label. The primary menu 1302, as well as the submenus 1304, 1306, and 1308 each comprise one or more of the following: (a) field labels, representing final biological field choices for the criteria menu 410, such as Chip Barcode, Hyb Date, Hyb Name, Hyb Type, Scan Date, Control, #/Scans in Group, and generally all items in that menu except for those labeled with a marker (➤); and biological subcategory labels, characterized by a marker (➤), which do not represent field choices but rather are indicative that further biological subcategory items to be displayed are available and queried upon.

In accordance with a preferred embodiment, the primary menu items and submenu items including all field labels, biological subcategory labels, and relationships among them are not "hard-coded" into the biological response analysis software 304. Rather, they are obtained from the database at program initiation, thus allowing for increased flexibility and customizability. Thus, at step 1202, the biological response analysis software 304 is initiated ("started up") by the user. At step 1204, biological response analysis software 304 retrieves dynamic menu information from the biological response database 312, the dynamic menu information including the primary menu items and submenu items including all field labels, biological subcategory labels, etc., needed for menuing. By dynamic menu information, it is meant that this menu information may be changed by simply changing the contents of the biological response database 312 without the need for changing the "hard-coding" of the biological response analysis software 304.

At step 1206 the user selects a primary menu item, which may be either a biological field label or a biological subcategory label. At step 1208 it is determined whether the user has selected a biological subcategory label. If not, then the user has selected a biological field label, and the menu selection process is complete, which is then followed by step 1215. If a biological subcategory label was chosen at step 1208, the dynamic menu information that was retrieved at program start-up is used at step 1210 to construct and display the subcategory items on a submenu such at submenu 1304 in FIG. 13. At step 1212, the user selects an item from the submenu and the process is repeated until a biological field label is chosen, in which case the menu selection process is complete, which is then followed by step 1215.

At step 1215, the valid operators for the selected menu item are displayed to the user. At step 1216, the user is provided with the appropriate interface for selection or entry of a value for the selected menu item for search. At step 1217, the user adds more search criteria if necessary by repeating the above steps as appropriate. At step 1218, a database query is constructed using the user-entered data and data relationships stored in the database for transmission to the biological database software 302. In the example of FIG. 13, the user selects biological subcategory labels "Sample(s)," "Strain," and "Full Genotype" from the successive menus and submenus 1302, 1304 and 1306, respectively, and is in the process of finally selecting a biological field label "Gene Name" in submenu 1308.

Advantageously, the dynamic biological menu generation algorithm shown in FIGS. 12 and 13 allows for an enhanced degree of flexibility and customization in the implementation of biological response analysis software 304, as it no longer needs to be programmed directly with the submenu data shown at submenus 1304, 1306, and 1308 of FIG. 13. Rather, the they are obtained from the database at program initiation at step 1204. As a result, one or more menuing systems of the biological response analysis software 304, such as the criteria menu 410, is fully changeable by loading the appropriate data into the biological response database 312, and programming or updating of the biological response analysis software 304 is not required. From a practical implementation perspective, this is advantageous because the modification of the biological response database 312 is easier to implement than widespread updating of the biological response analysis software 304. Moreover, because different databases 312 (as discussed supra, the database 312 may be only one of many such databases) may correspond to different research entities, each research entity having its own specific menuing needs, flexibility is achieved because the separate entities may be provided with the same biological response software 304, and their differing menuing needs may be met simply through a custom programming of their respective databases 312. In a biological response data network 100 according to the preferred embodiments, when a change is desired in biological response analysis software 304 menuing systems, or when the nature of the experiments change for providing different biological response results, or when a specific site or user requires specific needs, changes may be implemented quickly and efficiently through the relatively simple process of changing the biological response database 312.

Figure 14:
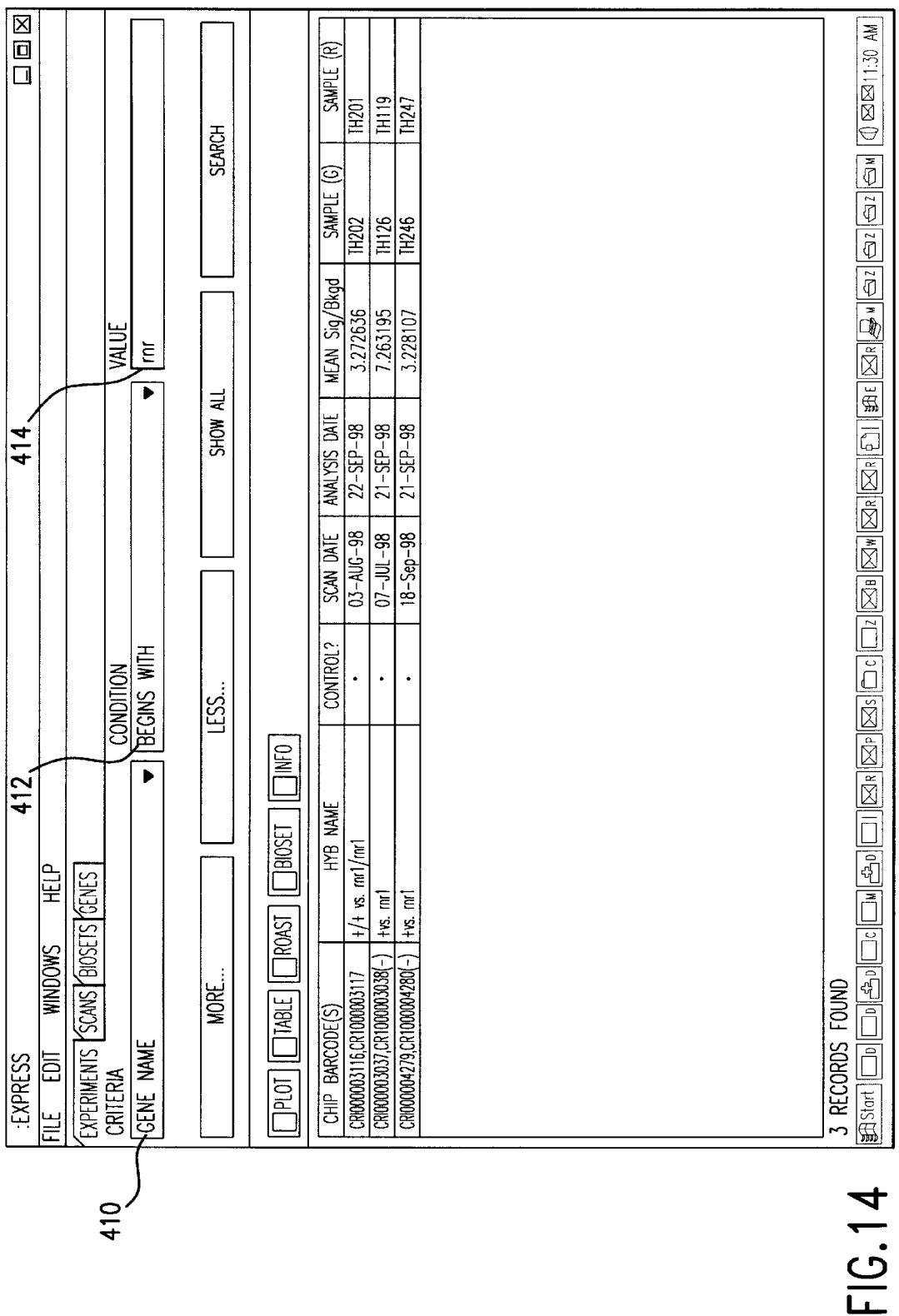
FIG. 14 shows the main search window of FIG. 13 after a search has been performed.

FIG. 14 shows a exemplary main search menu display screen after a search has been performed, wherein the user has selected "Gene Name" in the experiments tab 402 from the dynamic biological menu generation algorithm of FIG. 12 for the criteria menu 410, has selected the condition "begins with" from the condition menu 412, and has entered the character string "rnr" into the value field 410. As shown in FIG. 14, only 3 of the 1,046 records contained in the biological response database 312 of that example contained that entry.

Figure 15:
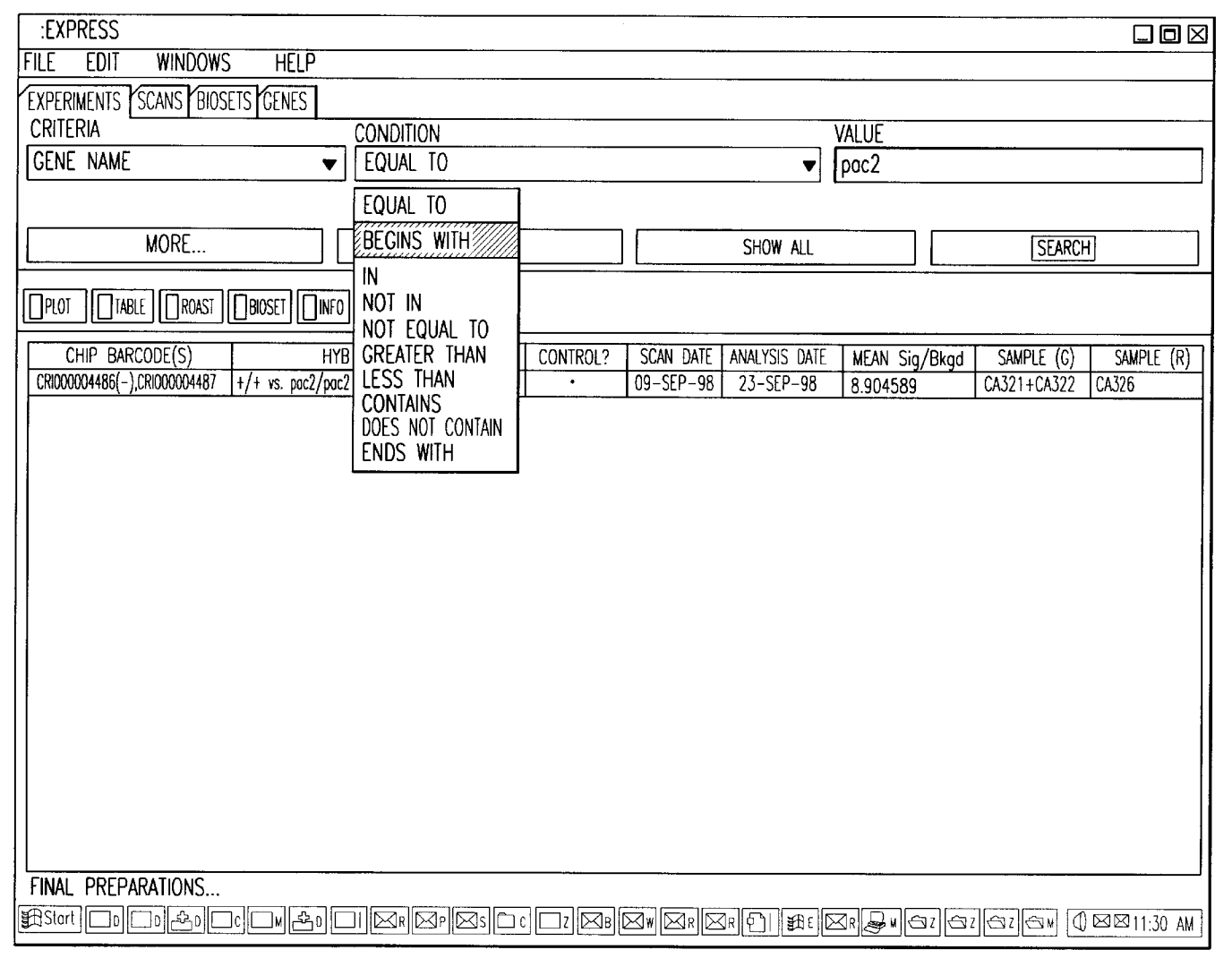

FIG. 15 shows a pull-down menu corresponding to the condition menu 412 under the experiments tab 402, showing generally the types of conditions that may be imposed on the search criteria. In the example of FIG. 15, the user has selected the condition "equal to," and has entered the search value "PAC 2." As shown, only a single experiment in the biological response database 312 is found to involve a perturbation of the PAC2 gene. It is to be appreciated that while the condition menu 412 does not contain subcategory items in the example of FIG. 15, such configuration is within the scope of the preferred embodiments. The condition menu 412 can also dynamically change to a selection interface if a criteria or condition selected is appropriate to a particular value interface. For example, when the "Hyb Type" criteria is selected, which has a small number of possible distinct values, a selector is displayed to allow easy selection from among the possibilities.

Figure 16:
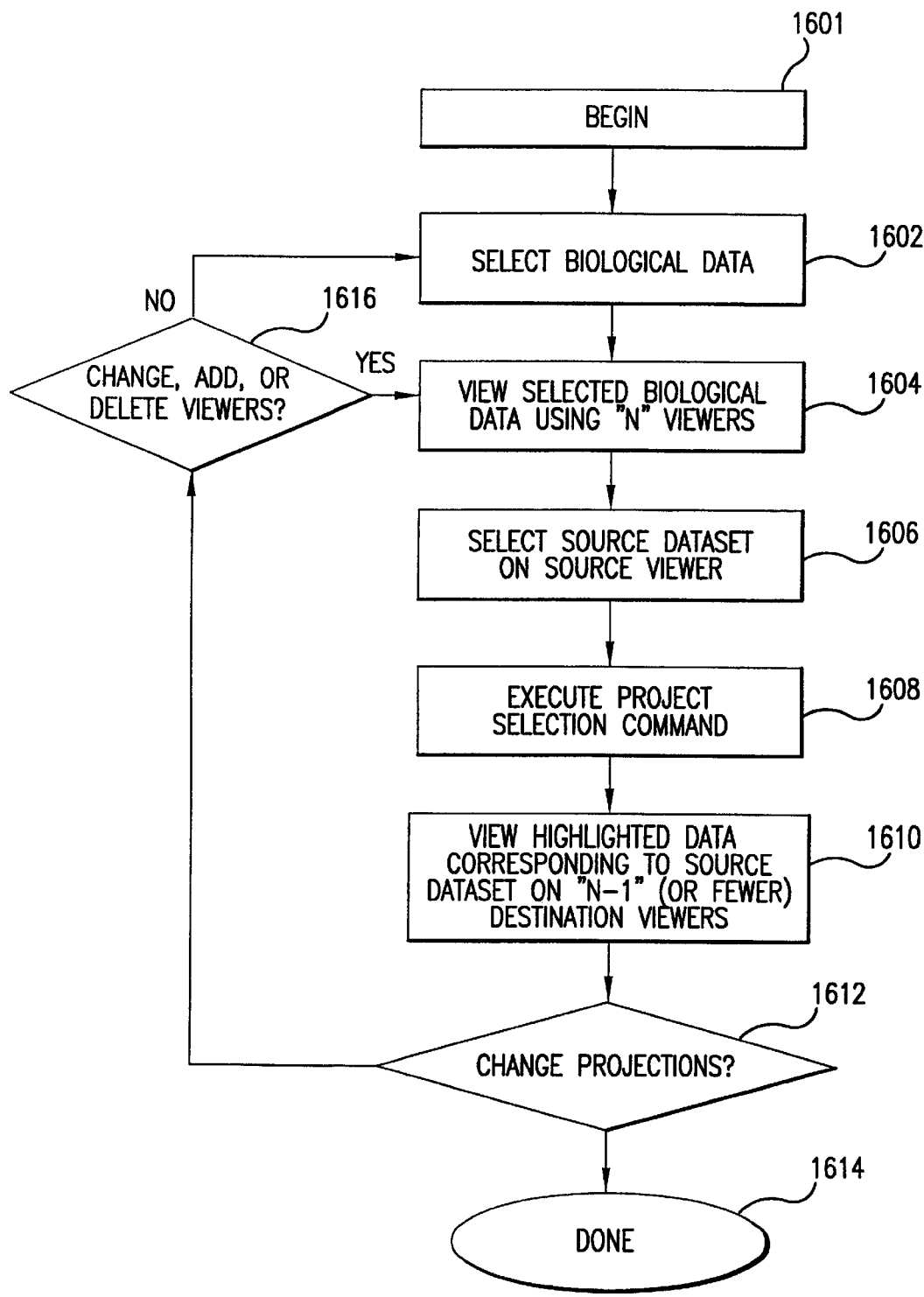
FIG. 16 shows steps for computer-assisted analysis of biological response data in accordance with a preferred embodiment.

FIG. 16 shows steps for computer-assisted analysis of biological response data in accordance with a preferred embodiment, the steps being used in conjunction with the biological response analysis software 304. It has been found that it is desirable not only to provide computer software for analyzing biological data using the separated biological viewers disclosed supra, but also to integrate these biological viewers by allowing the projection of selected datasets onto these biological viewers. In one preferred embodiment, the dataset to be projected is selected according to search methods disclosed supra and projected onto all currently active biological viewers, using appropriate highlighting such as color highlighting. In another preferred embodiment, a source dataset is selected from a source viewer, i.e., a first currently active biological viewer, and projected onto one or more destination viewers, i.e., one or more of the other currently active biological viewers. The source dataset is projected onto the destination biological viewers through the highlighting of destination data points that correspond to the source dataset, making these data points stand out for clear recognition by the user, thus enhancing the ability to recognize relationships, trends, patterns, etc. in the biological response database. This also allows the user to identify a meaningful response using a viewer well-suited to a particular purpose, then see the same response in other viewers to support or refute the discovery.

Figure 17A:
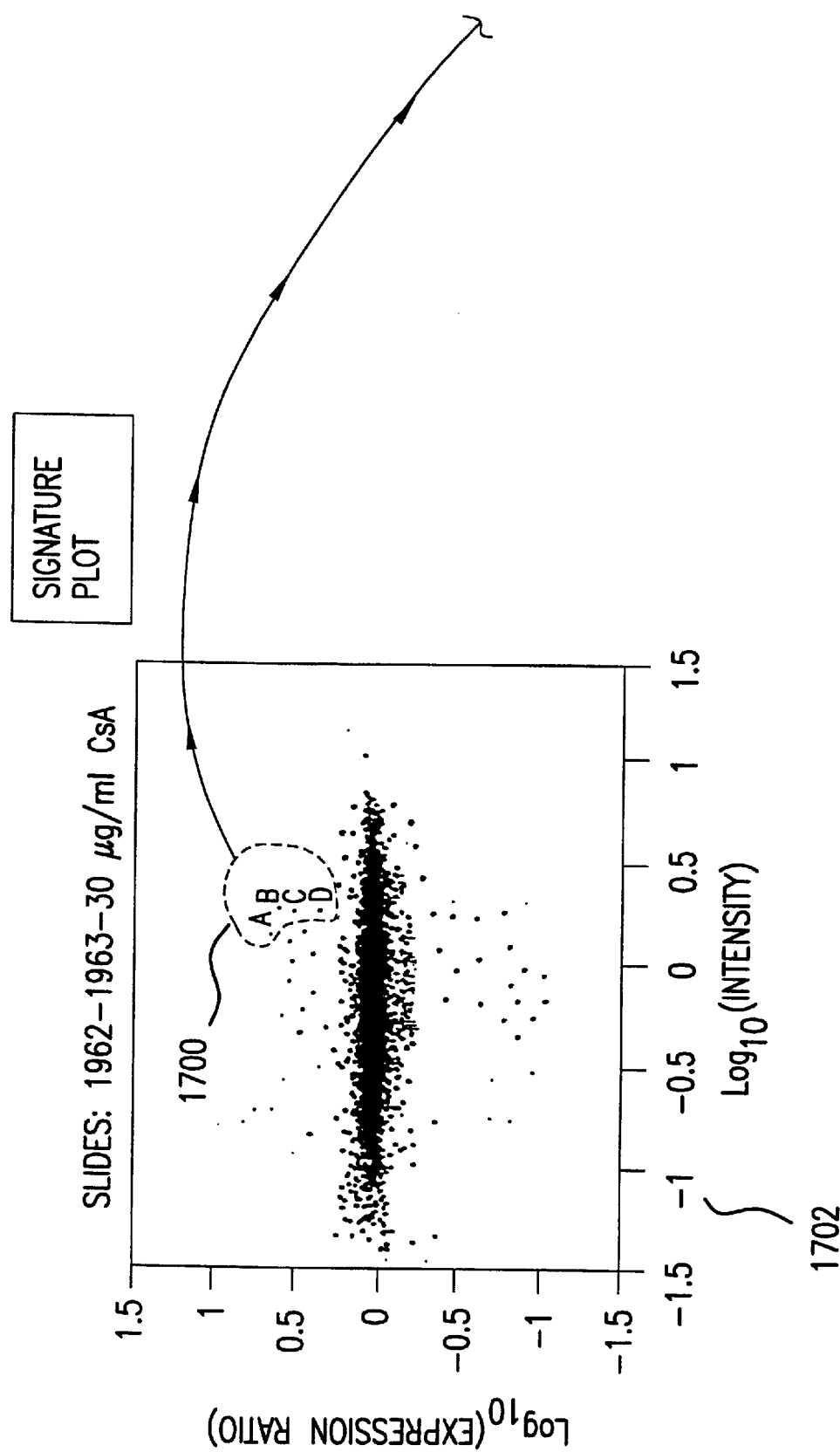
Figure 17B:
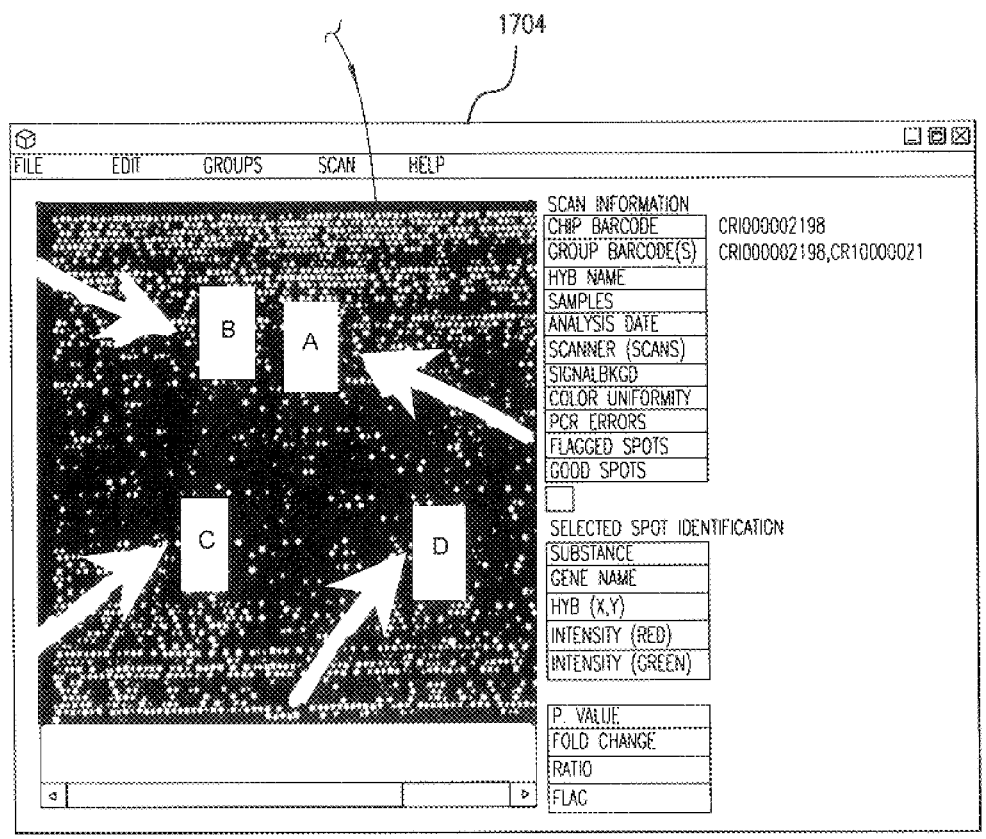

FIG. 17 shows a projection of selected biological data in accordance with a preferred embodiment, wherein a source dataset 1700 selected from a source viewer 1702 is projected onto a destination viewer 1704. The steps of FIG. 16 will be described with reference to the projection of FIG. 17, it being understood that the scope of the preferred embodiments is not so limited. At steps 1602 and 1604, the user selects and displays experiment, scan, bioset, gene, or other biological response datapoints taken from biological response database 312 in accordance with the search and display algorithms described supra in the present disclosure, and displays them in "N" biological data viewers simultaneously on the display screen of user computer 108. In FIG. 17, for example, the user has chosen a particular scan and displayed it using the signature plot biological viewer in window 1702, and has also chosen a particular scan (which may be the same scan or another scan having some genes in common) and displayed its data using the expression image biological viewer in window 1704. Although the number of active biological viewers "N" is only 2 in the example of FIG. 17 for simplicity and clarity of disclosure, "N" may be quite large in practice as windows may overlap, and is limited only by the size of the display screen and the computational resources available in user computer 108.

At step 1606, the user selects the source dataset 1700 from a source viewer using a graphical and/or query-based selection process. In the example of FIG. 17, the source dataset 1700 is circled using a lasso technique, wherein the user clicks the left mouse button while drawing a polygon around datapoints displayed on the plot. Accordingly, the source dataset comprises the set of genes corresponding to the circled locations on the plot. It is to be appreciated that many other graphical selection processes may be used in accordance with the preferred embodiments, e.g. multiple individual mouse clicks, circling with pen computing device pointers, etc. Also, query-based selection processes may be performed, wherein a database query is formulated using the "find" command from the edit menu.

At step 1608, the user executes a project selection command by pressing a project selection launch button or selecting a similar menu item. Responsive to the project selection command, biological response analysis software 304 causes the genes in the selected dataset to be highlighted in the destination viewer 1704, as shown in FIG. 17. The user then views the highlighted data at step 1610. It is to be appreciated that the arrow between windows in FIG. 17 is included only for clarity of disclosure, and does not actually show up on the display screen in a preferred embodiment. The example of FIG. 17 shows highlighting of the projected dataset by the placement of arrows to the projected genes, which may be suitable for a binary black and white display environment (or, more particularly, a binary black and white photocopy environment as with the present disclosure). Preferably, however, the projected data points are highlighted using a different screen contrast, brightness, color differentiation scheme colors, or other marking methods suitable for drawing the attention of the user to the projected dataset.

In accordance with a preferred embodiment, the user is permitted to disable projections for any biological viewer window by selecting a "disable projections" option using a launch button or menu command made available in each biological viewer. When "disable projections" is activated, there will be no highlighting of data on that biological viewer during projections made from other biological viewers. The "disable projections" option is preferably made available on an individual window basis, and disabling projections on one biological viewer does not affect projection operations onto other biological viewers.

FIG. 18 shows a projection of selected biological data in accordance with a preferred embodiment. In FIG. 18, a source dataset 1800 from a first signature plot biological viewer 1802 is projected onto a second signature plot biological viewer 1804 and onto a third signature plot biological viewer 1806. The source dataset comprises the hypothetical genes A, B, C, D, E, and F that were circled using a lasso technique as described supra. In the hypothetical example of FIG. 18, the Biological response analysis software 304 may permit the user to more readily observe certain behaviors regarding genes A–F and drugs X, Y, and Z. In particular, the Biological response analysis software 304 may permit the user to quickly observe that the genes A–F, which are significantly upregulated by the drug X, are not all upregulated by drug Y, and indeed only gene A, gene B, and perhaps gene C are substantially upregulated. The user may also quickly observe that genes A, B, and C are substantially downregulated by drug Z and none are substantially upregulated.

FIG. 19 shows projection of selected biological data in accordance with a preferred embodiment. In FIG. 19, a source dataset 1900 from a signature plot biological viewer 1902 is projected onto a correlation plot biological viewer 1904 and onto a trend plot biological viewer 1906. Prior to projection of the source dataset 1900, the user has created the signature plot in biological viewer 1902 using the plot launch button 416 on the experiments tab 402 as described supra, and has also created the trend plot in biological viewer 1904 from the biosets viewer as described supra. The user may also make observations regarding the genes A–F and drugs X–Z from these dataset projections. It is to be appreciated there are many combinations of dataset projections that are possible in accordance with the preferred embodiments using the many biological viewers disclosed supra. As a nonlimiting example, the source datasets may be taken from a gene coregulation tree biological viewer disclosed supra and projected onto any of the destination viewer of FIGS. 17, 18 or 19, or the source datasets may be taken from any of the destination viewer of FIGS. 17, 18 or 19 and projected onto the gene coregulation tree biological viewer.

Figure 21:
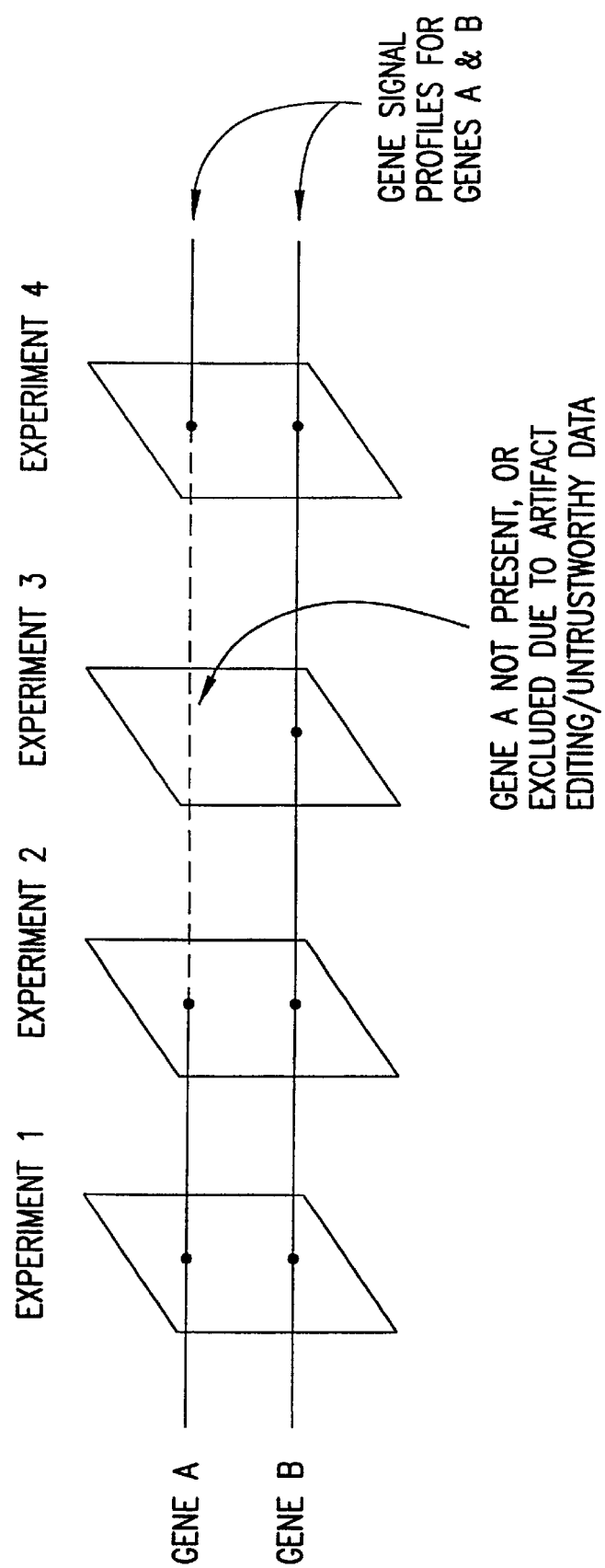
FIG. 21 shows a conceptual diagram corresponding to steps for constructing a gene signal profile from a plurality of experimental profiles in accordance with a preferred embodiment.

With reference to FIG. 21, in accordance with the preferred embodiments, a cellular signal profile may be constructed from multiple experimental signal profiles rather than just a single experimental signal profile. As used herein, when multiple experimental signal profiles are combined into a single experimental signal profile, each experimental signal profile that was combined is referred to as a constitutive experimental profile. By combining constitutive experimental profiles into a single cellular signal profile, the methods of the present invention, including the ability to group particular cellular constituents (such as gene expression levels) and the ability to compare and visualize response data, have been extended so that the same methods can be used to analyze multiple experimental signal profiles simultaneously.

As an alternative to combining all the data found in constitutive experimental profiles, the response of a single gene can be collected from each of the constitutive experimental profiles to form a "gene signal profile". Thus the gene signal profile represents the response of a particular gene in several constitutive experimental signal profiles. The individual responses of the particular gene in each of the constitutive experimental signal profiles is not averaged together to form the gene signal profile. Rather the individual responses are preserved in a multidimensional data structure.

The extension of the methods of the present invention to simultaneous analysis of gene response across multiple experiments has substantial advantages over prior art. For example, the expression level of a particular gene, or a family of particular genes, in response to a plurality of biological perturbations, such as increasing exposure to a pharmacological agent, can easily be determined using the methods of the present invention. In another example, the expression level of particular genes and/or any other types of measurable experimental biological response data can be correlated across multiple diverse experiments in order to identify genes or signals that are coregulated with respect to the various perturbations used in the multitude of experimental signal profiles analyzed. Alternatively, because the plurality of experimental signal profile experiments is capable of establishing a "baseline" expression level and/or amount for each cellular constituent, simultaneous analysis of multiple experimental signal profiles allows for the identification of particular experimental signal profiles in which the response of particular gene or group of genes is unique. These methods further provide an excellent method for validating the biological response of a pharmacological agent or test agent. By comparing the exposure of aliquots of a nominal biological sample, such as a particular cell line, in which each aliquot has been exposed to a reference compounds or the test compound, one can determine whether the test compound affects the same class of cellular constitutions as the reference compounds. Further, one can use the methods of the present invention to precisely define the relationship between the test compound and the reference compound over a multitude of perturbations including genetic manipulations of the biological sample.

To apply the methods of the present invention to multiple experiment signal profiles, it is necessary that the individual experiment profiles used for the construction of the gene signal profile be constructed such that, taken together, they yield one or more biological signal measurements for each of the genes whose profiles are being created. The experiments must also be normalizable. That is, the experiments must all yield data with common units, or data that is convertible to common units. For example, experiments based upon sequence tag based gene expression methods measure relative or absolute abundance of each gene transcript. Other experiments may measure gene or protein expression and/or activity levels and alternatively express these measurements as percent of transcript pool, copies per cell, hybridization intensity on Western blots or single-channel microarrays and related forms of measurement depending upon the nature of the experiment. Regardless of the form taken, all measurements must have the same units (dimension) and be directly applicable to the construction of composite gene signal profiles.

Dimensionless experiments, such as ratio-based measurements based upon multi-flour microarray experiments (Shalon et. al., 1996, "A DNA Microarray System for Analyzing Complex Samples Using Two-Color Flourescent Probe Hybridization," Genome Research 6:639–645) can also be adapted for use according the methods of the present embodiment by insuring that each experiment included in the analysis has one or more measurements of reference cellular constituents (expressed as a ratio) relative to a "baseline" ratio. The "baseline" may be established by measuring one or more reference cellular constituents in all ratio-based experiments included in the analysis or it may be compared to a condition that is itself a common baseline or normalizable to a common baseline within the database of experiment profiles.

For example, with reference to FIG. 21, experiment signal profiles 1, 2, 3 and 4 are all ratio-based gene expression measurements. With data corresponding to . . .

Experiment Profile 1: GeneA Signal, GeneB Signal
Experiment Profile 2: GeneA Signal, GeneB Signal
Experiment Profile 3: GeneB Signal
Experiment Profile 4: GeneA Signal, Gene B Signal
. . . one can construct the following gene signal profiles:
GeneA: Experiment1 Signal, Experiment2 Signal, Experiment4 Signal
GeneB: Experiment1 Signal, Experiment2 Signal, Experiment3 Signal, Experiment4 Signal This approach can be used for example to identify the experiments in which a particular gene or collection of genes is perturbed or affected.

The approach illustrated in this section has been used to identify experiments in which a particular gene or collection of genes is perturbed or affected. In the example of FIG. 5, a gene signal profile for a yeast gene RNR2 has been constructed using the RNR2 component of 863 biological signal profiles for experiments involving yeast gene expression monitoring of samples derived from cells with a variety of drug treatments or genetic perturbations. The profile exposes that RNR2 transcript levels are elevated with increasing concentration of the drug methotrexate (labeled MTX on plot). In that example, all experiments chosen to construct the RNR2 signal profile have a common baseline: yeast "wild type" untreated cells.

Figure 22:
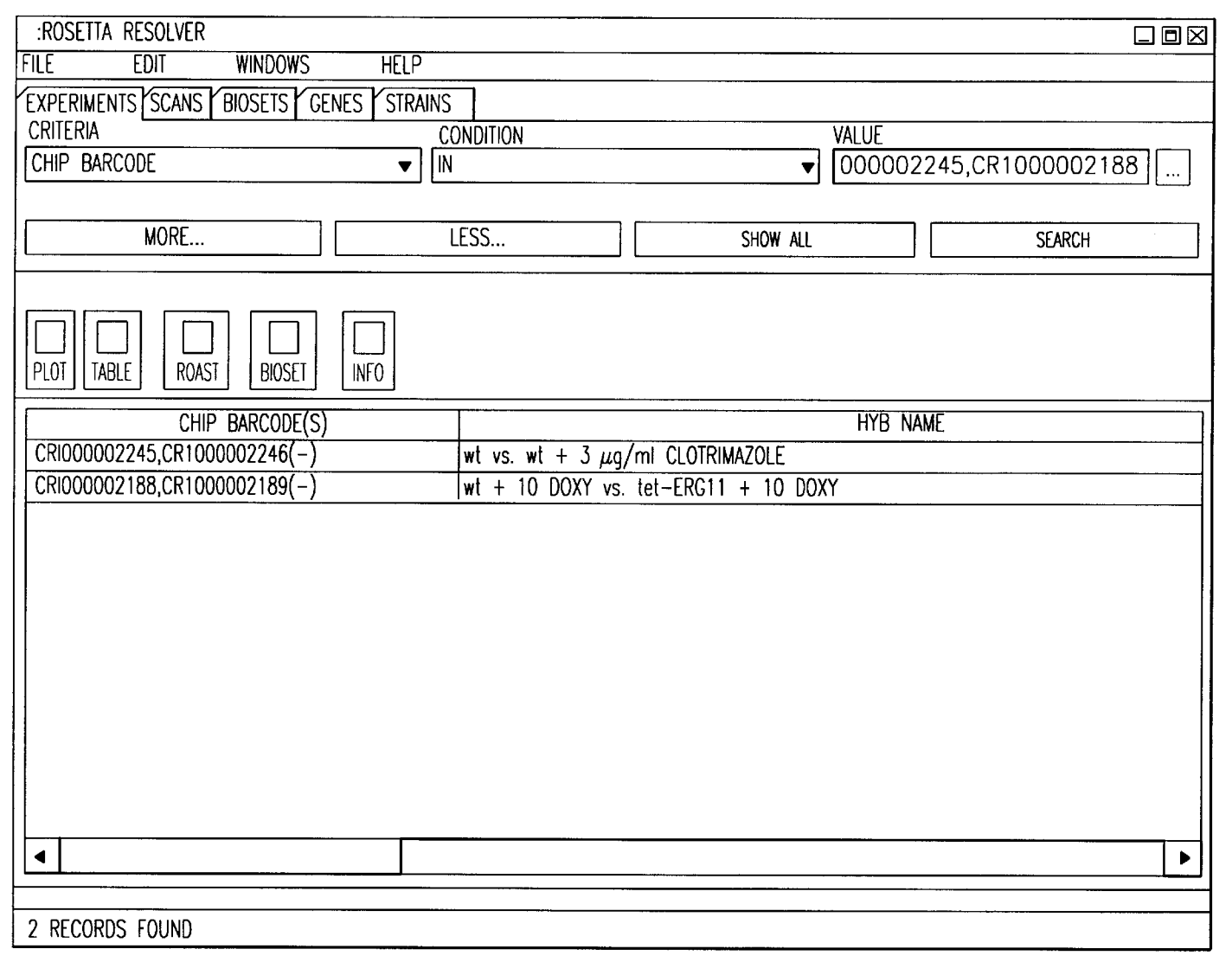
Figure 23A:
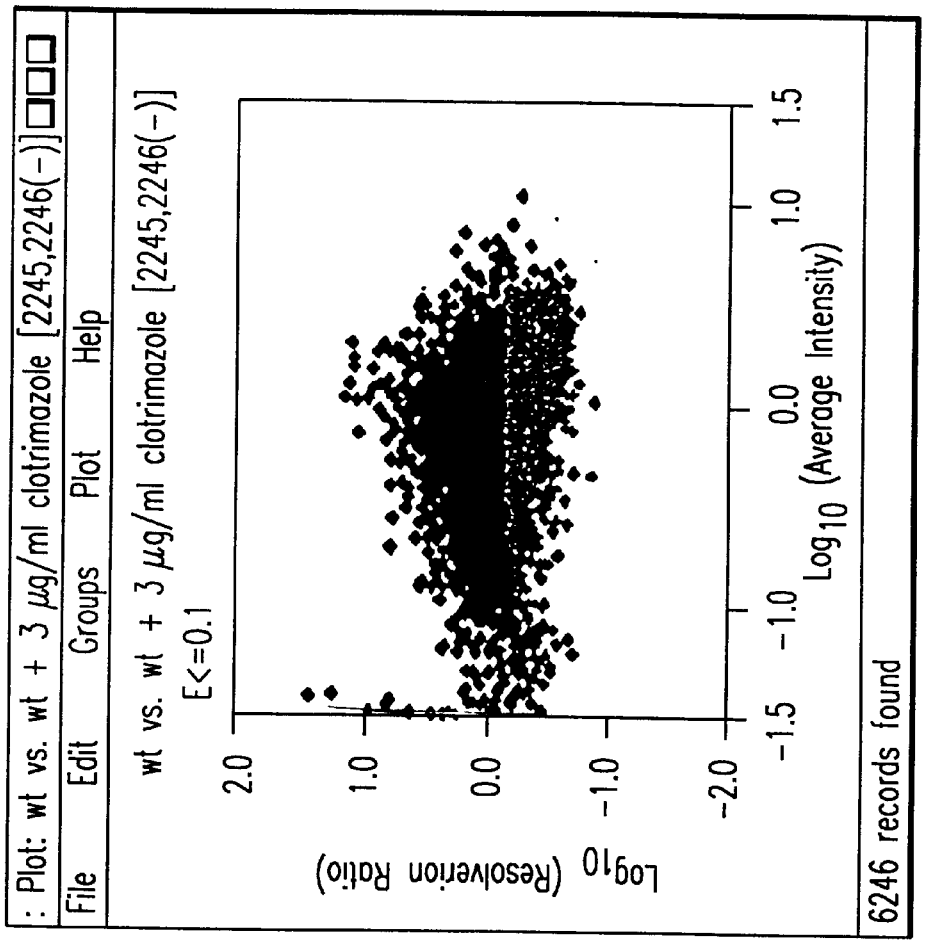
FIG. 23 shows a "resolved" profile that is the result of subtracting an Experiment profile of yeast cells harboring an impaired version of a gene, ERG11 and an Experiment profile of yeast cells treated with the drug clotrimazole.
Figure 23B:
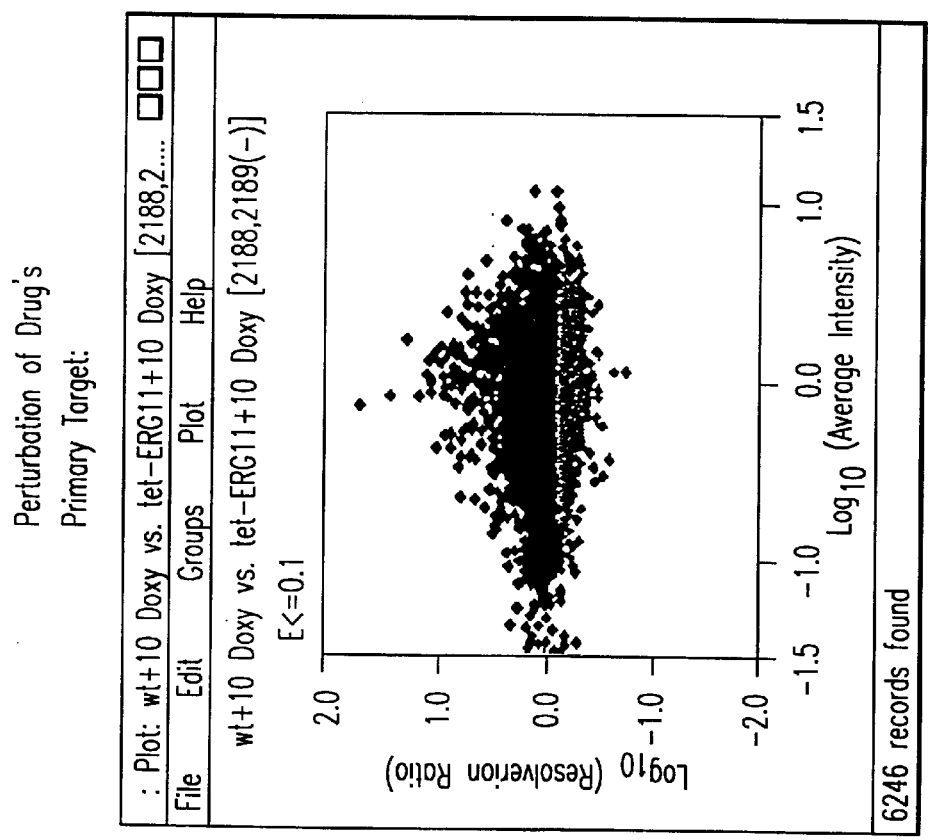
Figure 23C:
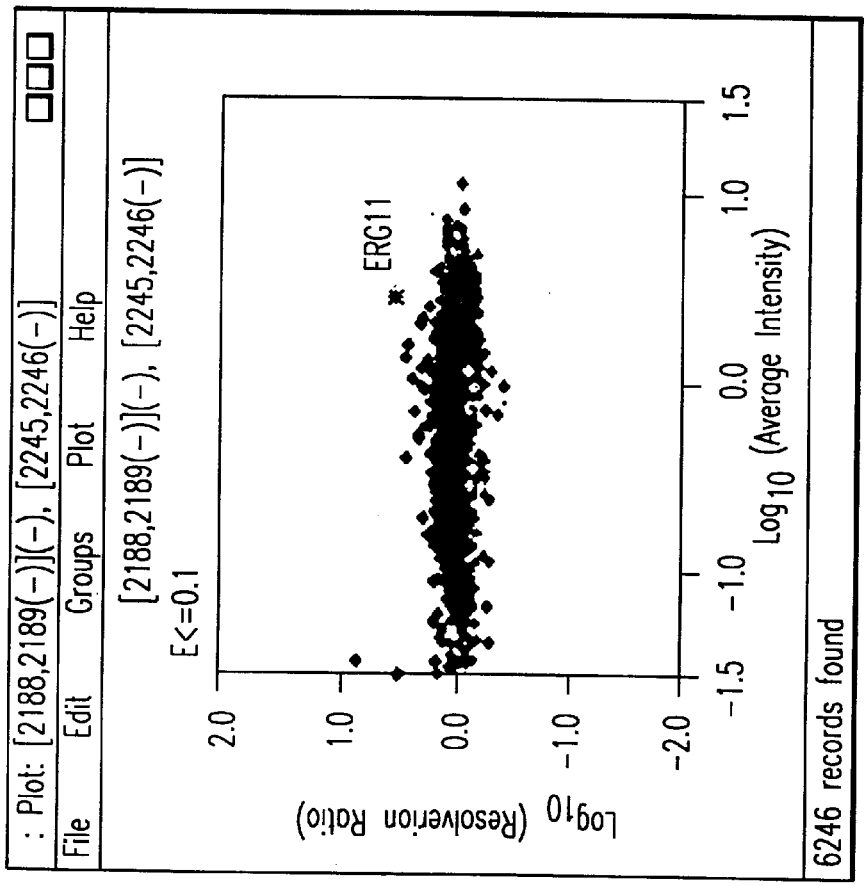

With reference to FIG. 22 and 23, in accordance with the preferred embodiments, a "Resolve" feature is provided that allows subtraction of biological signal profiles or combinations thereof from one another. The resolve feature can be used in many circumstances to validate drug targets. As shown in FIG. 22 and FIG. 23, exemplary profiles such as, an Experiment profile based on yeast cells harboring an impaired version of a gene, ERG11, which is the target of the antifungal drug clotrimazole (ERG11; at left on FIG. 23), along with an Experiment profile of yeast cells treated with the drug clotrimazole (tet; at right on FIG. 23) can serve as input to the "Resolve" feature. The "resolved" profile, showing the differences between the two profiles (clotrimazole treated cell profile minus tet-ERG11 cell profile) is shown at the bottom of FIG. 23. The only significant outlier is the ERG11 gene, because it was turned off in the tet-ERG11 experiment, but remains active in the drug treated cell. This is indicative of a very precise drug that closely mimics the cellular effects of the deletion of its target. As this example illustrates, the "resolve" feature represents an method for validating the effects of drugs or for validating drug targets. While this illustration demonstrates the subtraction of one Experiment profile from another, one skilled in the art will appreciate that combinations of profiles may be subtracted from a single profile or from yet other combinations of profiles.

While preferred embodiments have been described, these descriptions are merely illustrative and are not intended to limit their scope. For example, although preferred embodiments described above were in the context of a system for storage, retrieval, and analysis of biological expression array data, those skilled in the art will recognize that the disclosed methods and structures are readily adaptable for broader applications. For example, the preferred embodiments are readily applicable to a variety of tools that analyze large amounts of machine-readable biological experiment data. Further, one skilled in the art will note that, although the concept of "hyperbolic trees" is discussed, hyperbolic trees are by no means the only form of cluster visualization utilized by the methods of the present invention. The concept of a hyperbolic tree is only one embodiment of the cluster visualization envisioned by the patent and serves as a non-limiting example.

5.2. Measurement Methods

Biological response signals are obtained for use in the instant invention by measuring the cellular constituents changed, e.g., by drug exposure or by pathway perturbation. These cellular constituents can be of any aspect of the biological state of a cell. They can be, e.g., of the transcription state, in which RNA abundances are measured, the translation state, in which protein abundances are measured, the activity state, in which protein activities are measured. The cellular characteristics can also be of mixed aspects, for example, in which the activities of one or more proteins; originating a particular biological pathway are measured along with RNA abundances (gene expression) of cellular constituents in the pathway downstream of the originating protein(s). This section describes exemplary methods for measuring the cellular constituents in drug or pathway responses. This invention is adaptable to other methods of such measurement.

Embodiments of this invention based on measuring the transcriptional state of drug and pathway responses are preferred. The transcriptional state can be measured by techniques of hybridization to arrays of nucleic acid or nucleic acid mimic probes, described in the next subsection, or by other gene expression technologies, described in the subsequent subsection. However measured, the result is response data including values representing RNA abundance ratios, which usually reflect DNA expression ratios (in the absence of differences in RNA degradation rates). Such measurement methods are described in Section 5.4.2.

In various alternative embodiments of the present invention, aspects of the biological state other than the transcriptional state, such as the translational state, the activity state, or mixed aspects can be measured. Details of these embodiments are described in this section. Such measurement methods are described in Section 5.4.3.

5.2.1. Measurement of Drug Response Data

To measure drug response data, cell are exposed to graded levels of the drug or drug candidate of interest. When the cells are grown in vitro, the compound is usually added to their nutrient medium. In the case of yeast, such as *S. cerevisiae*, it is preferably to harvest the cells in early log phase, since expression patterns are relatively insensitive to time of harvest at that time. The drug is added in a graded amount that depends on the particular characteristics of the drug, but usually will be between about 1 ng/ml and 100 mg/ml. In some cases a drug will be solubilized in a solvent such as DMSO.

The biological state of cells exposed to the drug and cells not exposed to the drug is measured according to any of the below described methods. Preferably, transcript or microarrays are used to find the mRNAs with altered expression due to exposure to the drug. However, other aspects of the biological state may also be measured to determine, e.g., proteins with altered translation or activities due to exposure to the drug.

It is preferable for measurements of drug responses, in the case of two-colored differential hybridization described below, to measure also with reversed labeling. Also, it is preferable that the levels of drug exposure used provide sufficient resolution of rapidly changing regions of the drug response, e.g., by using approximately ten levels of drug exposure.

5.2.2. Transcriptional State Measurement

In general, measurement of the transcriptional state can be performed using any probe or probes which comprise a polynucleotide sequence and which are immobilized to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probe may be full or partial sequences of genomic DNA, cDNA, or mRNA sequences extracted from cells. The polynucleotide sequences of the probes may also be synthesized nucleotide sequences, such as synthetic oligonucleotide sequences. The probe sequences can be synthesized either enzymatically in vivo, enzymatically in vitro, (e.g., by PCR), or non-enzymatically in vitro.

The probe or probes used in the methods of the invention are preferably immobilized to a solid support or surface which may be either porous or non-porous. For example, the probes of the invention may be polynucleotide sequences which are attached to a nitrocellulose or nylon membrane or filter. Such hybridization probes are well known in the art (see, e.g., Sambrook et al., Eds., 1989, *Molecular Cloning: A Laboratory Manual*, 2nd ed., Vols. 1–3, Cold Spring Harbor Laboratory, Cold Spring Harbor, N.Y.). Alternatively, the solid support or surface may be a glass or plastic surface.

5.2.2.1. Microarrays Generally

In a particularly preferred embodiment, measurement of the transcriptional state are made by hybridization to microarrays of probes consisting of a solid phase, on the surface of which are immobilized a population of polynucleotides, such as a population of DNA or DNA mimics, or, alternatively, a population of RNA. Specifically, a microarray is an array of less than 6.25 cm$^2$ in size. Microarrays can be employed, e.g., for analyzing the transcriptional state of a cell, such as the transcriptional states of cells exposed to graded levels of a drug of interest.

In preferred embodiments, a microarray comprises a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably, the microarrays are small, usually smaller than 5 cm$_2$, and they are made from materials that are stable under binding (e.g., nucleic acid hybridization) condition. Preferably, a given binding site or unique set of binding sites in the microarray will specifically bind (e.g., hybridize) to the product of a single gene in a cell (e.g., to a specific mRNA, or to a specific cDNA derived therefrom). However, as discussed supra, in general other, related or similar sequences will cross hybridize to a given binding site. Although there may be more than one physical binding site per specific RNA or DNA, for the sake of clarity the discussion below will assume that there is a single, completely complementary binding site.

The microarrays of the present invention include one or more test probes, each of which has a polynucleotide sequence that is complementary to a subsequence of RNA or DNA to be detected. Each probe preferably has a different nucleic acid sequence. The position of each probe on the solid surface is preferably known. In one embodiment, the microarray is a high density array, preferably having a density greater than about 60 different probes per 1 cm$^2$. In one embodiment, the microarray is an array (i.e., a matrix) in which each position represents a discrete binding site for a product encoded by a gene (i.e., an mRNA or a cDNA derived therefrom), and in which binding sites are present for products of most or almost all of the genes in the organism's genome. For example, the binding site can be a DNA or DNA analogue to which a particular RNA can specifically hybridize. The DNA or DNA analogue can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often to about 75%, more often to at least about 85%, even more often to about 90%, and still more often to at least about 99%. Preferably, the microarray has binding, sites for genes relevant to the action of a drug of interest or in a biological pathway of interest. A "gene" is identified as an open reading frame ("ORF") which encodes a sequence of preferably at least 50, 75, or 99 amino acids from which a messenger RNA is transcribed in the organism or in some cell in a multicellular organism. The number of genes in a genome can be estimated from the number of mRNAs expressed by the organism, or by extrapolation from a well characterized portion of the genome. When the genome of the organism of interest has been sequenced, the number of ORF's can be determined and mRNA coding regions identified by analysis of the DNA sequence. For example, the genome of *Saccharomyces cerevisiae* has been completely sequenced, and is reported to have approximately 6275 ORFs longer than 99 amino acids. Analysis of the ORFs indicates that there are 5885 ORFs that are likely to encode protein products (Goffeau et al., 1996, *Science* 274:546–567). In contrast, the human genome is estimated to contain approximately 10$^5$ genes.

5.2.2.2. Preparing Probes for Microarrays

As noted above, the "probe" to which a particular polynucleotide molecule specifically hybridizes according to the invention is usually a complementary polynucleotide sequence. In one embodiment, the probes of the microarray are DNA or DNA "mimics" (e.g., derivatives and analogues) corresponding to at least a portion of each gene in an organism's genome. In another embodiment, the probes of the microarray are complementary RNA or RNA mimics.

DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtain, e.g., by polymerase chain reaction ("PCR") amplicafication of gene segments from genomic DNA, cDNA (e.g., by RT-PCR), or clones sequences. PCR primers are preferably chosen based on known sequences of the genes or cDNA that result in amplification of unique fragments (i.e.g, fragments that do not share more than 10 bases of contiguous identical sequence with any other fragment on the microarray). Computer programs that are well known in the art are useful in the design of primer with the required specificity and optimal amplification properties, such as Oligo version 5.0 (National Biosciences). Typically, each probe of the microarray will be between about 20 bases and about 12,000 bases, and usually between about 300 bases and about 2,000 bases in length, and still more usually between about 300 bases and about 800 bases in length. PCR methods are well known in the art, and are described, for example, in Innis et al., eds., 1990, *PCR Protocols: A Guide to Methods and Applications,* Academic Press Inc., San Diego, Calif. It will be apparent to one skilled in the art that controlled robotic systems are useful for isolating and amplifying nucleic acids.

An alternative means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399–5407; McBrid et al., 1983, *Tetrahedron Lett.* 24:246–248). Synthetic sequences are typically between about 15 and about 500 bases in length, more typically between about 20 and about 50 bases. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566–568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207–209).

5.2.2.3. Attaching Probes to the Solid Surface

The probes are attached to a solid support or surface, which may be made, e.g., from glass, plastic (e.g., polypropylene, nylon), polyacrylamide, nitrocellulose, or other materials. A preferred method for attaching the nucleic acids to a surface is by printing on glass plates, as is described generally by Schena et al., 1995, *Science* 270:467–470. This method is especially useful for preparing microarrays of cDNA (See also, DeRisi et al., 1996, *Nature Genetics* 14:457–460; Shalon et al., 1996, *Genome Res.* 6:689–645; and Schena et al., 1995, *Proc. Natl. Acad. Sci. U.S.A.* 93:10539–11286). Blanchard discloses the use of an ink jet printer for oligonucleotide synthesis (U.S. application Ser. No. 09/008,120, filed Jan. 16, 1998).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767–773; Pease et al., 1994, *Proc. Natl. Acad. Sci. U.S.A.* 91:5022–5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687–690). When these methods are used, oligonucleotides (e.g., 20-mers) of known sequence are synthesized directly on a surface such as a derivatized glass slides. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids. Res.* 20:1679–1684), may also be used. In principle, any type of array, for example, dot blots on a nylon hybridization membrane (see Sambrook et al., supra) could be used. However, as will be recognized by those skilled in the art, very small arrays will frequently be preferred because hybridization volumes will be smaller.

5.2.2.4. Target Polynucleotide Molecules

As described, supra, the polynucleotide molecules which may be analyzed by the present invention may be from any source, including naturally occurring nucleic acid molecules, as well as synthetic nucleic acid molecules. In a preferred embodiment, the polynucleotide molecules analyzed by the invention comprise RNA, including, but by no means limited to, total cellular RNA, poly(A)$^-$ messenger RNA (mRNA), fractions thereof, or RNA transcribed from cDNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–5299). Poly (A)$^+$ RNA is selected by selection with oligo-dT cellulose. Cells of interest include, but are by no means limited to, wild-type cells, drug-exposed wild-type cells, modified cells, diseased cells, and, in particular, cancer cells.

In one embodiment, RNA can be fragmented by methods known in the art, e.g., by incubation with $ZnCl_2$, to generate fragments of RNA. In one embodiment, isolated mRNA can be converted to antisense RNA synthesized by in vitro transcription of double-stranded cDNA in the presence of labeled dNTPs (Lockhart et al., 1996, *Nature Biotechnology* 14:1675).

In other embodiments, the polynucleotide molecules to be analyzed may be DNA molecules such as fragmented genomic DNA, first strand cDNA which is reverse transcribed from mRNA, or PCR products of amplified mRNA or cDNA.

5.2.2.5. Hybridization to Microarrays

Nucleic acid hybridization and wash conditions are chosen so that the polynucleotide molecules to be analyzed by the invention "specifically bind" or "specifically hybridize" to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA or DNA) of probe and target nucleic acids. General parameters for specific (i.e., stringent) hybridization conditions are described in Sambrook et al. (supra), and in Ausubel et al., 1987, *Current Protocols in Molecular Biology,* Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in high stringency wash buffer (0.1×SSC plus 0.2% SDS) (Shena et al., 1996, *Proc. Natl. Acad. Sci. U.S.A.* 93:10614). Useful hybridization conditions are also provided, e.g., Tijessen, 1993, *Hybridization With Nucleic Acid Probes,* Elsevier Science Publishers B.V.; and Kricka, 1992, *Nonisotopic DNA Probe Techniques,* Academic Press, San Diego, Calif.

5.2.2.6. Signal Detection and Data Analysis

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses, one cell is exposed to a drug and another cell of the same type is not exposed to the drug. The cDNA derived from each of the two cell types are differently labeled so that they can be distinguished. In one embodiment, for example, cDNA from a cell treated with a drug is synthesized using a fluorescein-labeled dNTP, and cDNA from a second cell, not drug-exposed, is synthesized using a rhodamine-labeled DNTP. When the two cDNAs are mixed and hybridized to the microarray, the relative intensity of signal from each cDNA set is determined for each site on the array, and any relative difference in abundance of a particular mRNA is thereby detected.

In the example described above, the cDNA from the drug-treated cell will fluoresce green when the fluorophore is stimulated, and the cDNA from the untreated cell will fluoresce red. As a result, when the drug treatment has no effect, either directly or indirectly, on the relative abundance of a particular mRNA in a cell, the mRNA will be equally prevalent in both cells, and, upon reverse transcription, red-labeled and green-labeled cDNA will be equally prevalent. When hybridized to the microarray, the binding site(s) for that species of RNA will emit wavelength characteristic of both fluorophores. In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, *Science* 270:467–470. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639–645). In a preferred embodiment, the arrays are scanned with a laser fluorescent scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639–645. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two cells or cell lines is scored as a perturbation and its magnitude determined (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

5.2.2.7. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci. U.S.A.* 93:659–663). Other methods statistically sample cDNA pools, such as by sequencing sufficient bases (e.g., 20–50 bases) in each of multiple cDNAs to identify each cDNA, or by sequencing short tags (e.g., 9–10 bases) which are generated at known positions relative to a defined mRNA end (see, e.g., Velculescu, 1995, *Science* 270:484–487).

Such methods and systems of measuring transcriptional state, although less preferable than microarrays, may, nevertheless, be used in the present invention.

5.2.3. Measurement of Other Aspects of Biological State

Although monitoring cellular constituents other than mRNA abundances currently presents certain technical difficulties not encountered in monitoring mRNAs (i.e., the transcriptional state), it will be apparent to those skilled in the art that the use of methods of this invention are applicable to any cellular constituent that can be monitored.

In various embodiments of the present invention, aspects of the biological state other than the transcriptional state, such as the translational state, the activity state, or mixed aspects thereof can be measured in order to obtain drug responses for the present invention. Details of these embodiments are described in this section.

5.2.3.1. Translational State Measurements

Measurements of the translational state may be performed according to several methods. For example, whole genome monitoring of protein (i.e., the "proteome," Goffea et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual,* Cold Spring Harbor, N.Y.). In a preferred embodiment, monoclonal antibodies are raised against synthetic peptide fragments designed based on genomic sequence of the cell. With such an antibody array, proteins from the cell are contacted to the array, and their binding is assayed with assays known in the art.

Alternatively, proteins can be separated by two-dimensional gel electrophoresis systems. Two-dimensional gel electrophoresis is well known in the art, and typically involves iso-electric focusing along a first dimension followed by SDS-PAGE electrophoresis along a second dimension. See, e.g., Hames et al., 1990, *Gel Electrophoresis of Proteins: A Practical Approach,* IRL Press, New York; Shevchenko et al., 1996, *Proc. Natl. Acad. Sci. U.S.A.* 93:1440–1445; Sagliocco et al., 1996, *Yeast* 12:1519–1533; and Lander, 1996, *Science* 274:536–539. The resulting electropherograms can be analyzed by numerous techniques, including mass spectrometric techniques, western blotting, and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or overexpression of a specific gene.

5.2.3.2. Activity State Measurements

Where activities of proteins relevant to the characterization of drug action can be measured, embodiments of this invention can be based on such measurements. Activity measurements can be performed by my functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle (control, performance of the function can be observed. However known or measured, the changes in protein activities form the response data analyzed by the foregoing methods of this invention.

5.2.3.3. Mixed Aspects of Biological State

In alternative and non-limiting, embodiments, response data may be formed of mixed aspects of the biological state of a cell. Response data can be constructed from combinations of, e.g., changes in certain mRNA abundances, changes in certain protein abundances, and changes in certain protein activities.

5.3. Targeted Perturbation Methods

Methods for targeted perturbation of biological pathways at various levels of a cell are increasingly widely known and applied in the art. Any such methods that are capable of specifically targeting and controllably modifying (e.g., either by a graded increase or activation or by a graded decrease or inhibition) specific cellular constituents (e.g., gene expression, RNA concentrations, protein abundances, protein activities, or so forth) can be employed in performing pathway perturbations. Controllable modifications of cellular constituents consequentially controllably perturb pathways originating at the modified cellular constituents. Such pathways originating at specific cellular constituents are preferably employed to represent drug action in this invention. Preferable modification methods are capable of individually targeting each of a plurality of cellular constituents and most preferably a substantial fraction of such cellular constituents.

The following methods are exemplary of those that can be used to modify cellular constituents and thereby to produce pathway perturbations which generate the pathway responses used in the steps of the methods of this invention as previously described. This invention is adaptable to other methods for making controllable perturbations to pathways, and especially to cellular constituents from which pathways originate.

Pathway perturbations are preferably made in cells of cell types derived from any organism for which genomic or expressed sequence information is available and for which methods are available that permit controllably modification of the expression of specific genes. Genome sequencing is currently underway for several eukaryotic organisms, including humans, nematodes, Arabidopsis, and flies. In a preferred embodiment, the invention is carried out using a yeast, with *Saccharomyces cerevisiae* most preferred because the sequence of the entire genome of a *S. cerevisiae* strain has been determined. In addition, well-established methods are available for controllably modifying expression of year genes. A preferred strain of yeast is a *S. cerevisiae* strain for which yeast genomic sequence is known, such as strain S288C or substantially isogeneic derivatives of it (see, e.g., Dujon et al., 1994, *Nature* 369:371–378; Bussey et al., 1995, *Proc. Natl. Acad. Sci. U.S.A.* 92:3809–3813; Feldmann et al., 1994, *E.M.B.O. J* 13:5795–5809; Johnston et al., 1994, *Science* 265:2077–2082; Galibert et al., 1996, *E.M.B.O. J.* 15:2031–2049). However, other strains may be used as well. Yeast strains are available, e.g., from American Type Culture Collection, 10801 University Boulevard, Manassas, Va, 20110-2209. Standard techniques for manipulating yeast are described in C. Kaiser, S. Michaelis, & A. Mitchell, 1994, *Methods in Yeast Genetics: A Cold Spring Harbor Laboratory Course Manual,* Cold Spring Harbor Laboratory Press, New York; and Sherman et al., 1986, *Methods in Yeast Genetics: A Laboratory Manual,* Cold Spring Harbor Laboratory, Cold Spring Harbor. N.Y.

The exemplary methods described in the following include use of titratable expression systems, use of transfection or viral transduction systems, direct modifications to RNA abundances or activities, direct modifications of protein abundances, and direct modification of protein activities including use of drugs (or chemical moieties in general) with specific known action.

5.3.1. Titratable Expression Systems

Any of the several known titratable, or equivalently controllable, expression systems available for use in the budding yeast Saccharomyces cerevisiae are adaptable to this invention (Mumberg et al., 1994, *Nucl. Acids Res.* 22:5767–5768). Usually, gene expression is controlled by transcriptional controls, with the promoter of the gene to be controlled replaced on its chromosome by a controllable, exogenous promoter. The most commonly used controllable promoter in yeast is the GALL promoter (Johnston et al., 1984, *Mol Cell. Biol.* 8:1440–1448). The GALL promoter is strongly repressed by the presence of glucose in the growth medium, and is gradually switched on in a graded manner to high levels of expression by the decreasing abundance of glucose and the presence of galactose. The GAL1 promoter usually allows a 5–100 fold range of expression control on a gene of interest.

Other frequently used promoter systems include the MET25 promoter (Kerjan et al., 1986, *Nucl. Acids. Res.* 14:7861–7871), which is induced by the absence of methionine in the growth medium, and the CUP1 promoter, which is induced by copper (Mascorro-Gallardo et al., 1996, *Gene* 172:169–170). All of these promoter systems are controllable in that gene expression can be incrementally controlled by incremental changes in the abundances of a controlling moiety in the growth medium.

One disadvantage of the above listed expression systems is that control of promoter activity (effected by, e.g., changes in carbon source, removal of certain amino acids), often causes other changes in cellular physiology which independently alter the expression levels of other genes. A recently developed system for yeast, the Tet system, alleviates this problem to a large extent (Gari et al., 1997, *Yeast* 13:837–848). The Tet promoter, adopted from mammalian expression systems (Gossen et al., 1995, *Proc. Nat. Acad. Sci. USA* 89:5547–5551) is modulated by the concentration of the antibiotic tetracycline or the structurally related compound doxycycline. Thus, in the absence of doxycycline, the promoter induces a high level of expression, and the addition of increasing levels of doxycycline causes increased repression of promoter activity. Intermediate levels gene expression can be achieved in the steady state by addition of intermediate levels of drug. Furthermore, levels of doxycycline that give maximal repression of promoter activity (10 micrograms/ml) have no significant effect on the growth rate on wild type yeast cells (Gari et al., 1997, *Yeast* 13:837–848).

In mammalian cells, several means of titrating expression of genes are available (Spencer, 1996, *Trends Genet.* 12:181–187). As mentioned above, the Tet system is widely used, both in its original form, the "forward" system, in which addition of doxycycline represses transcription, and in the newer "reverse" system, in which doxycycline addition stimulates transcription (Gossen et al., 1995, *Proc. Natl. Acad. Sci. USA* 89:5547–5551; Hoffmann et al., 1997, *Nucl. Acids. Res.* 25:1078–1079; Hofmann et al., 1996, *Proc. Natl. Acad. Sci. USA* 83:5185–5190; Paulus et al., 1996, *Journal of Virology* 70:62–67). Another commonly used controllable promoter system in mammalian cells is the ecdysone-inducible system developed by Evans and colleagues (No et al., 1996, *Proc. Nat. Acad. Sci. USA* 93:3346–3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, *Proc. Nat. Acad. Sci. USA* 93:4604–4607; Spencer, 1996, *Trends Genet.* 12:181–187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, titratable expression systems, such as the ones described above, are introduced for use into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, *Development* 122:4149–4157; Spradling et al., 1995, *Proc. Natl. Acad. Sci. USA*, 92:10824–10830; Ramirez-Solis et al., 1993, *Methods Enzymol.* 225:855–878; and Thomas et al., 1987, *Cell* 51:503–512.

5.3.2. Transfection Systems for Mammalian Cells

Transfection or viral transduction of target genes can introduce controllable perturbations in biological pathways in mammalian cells. Preferably, transfection or transduction of a target gene can be used with cells that do not naturally express the target gene of interest. Such non-expressing, cells can be derived from a tissue not normally expressing the target gene or the target gene can be specifically mutated in the cell. The target gene of interest can be cloned into one of many mammalian expression plasmids, for example, the pcDNA3.1 +/− system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated.

A particular example of the use of this method is the search for drugs that target the src-family protein tyrosine kinase, lck, a key component of the T cell receptor activation pathway (Anderson et al., 1994, *Adv. Immunol.* 56:171–178). Inhibitors of this enzyme are of interest as potential immunosuppressive drugs (Hanke J H, 1996, *J. Biol Chem* 271(2):695–701). A specific mutant of the Jurkat T cell line (JcaM1) is available that does not express lck kinase (Straus et al., 1992, *Cell* 70:585–593). Therefore, introduction of the lck gene into JCaM1 by transfection or transduction permits specific perturbation of pathways of T cell activation regulated by the lck kinase. The efficiency of transfection or transduction, and thus the level of perturbation, is dose related. The method is generally useful for providing perturbations of gene expression or protein abundances in cells not normally expressing the genes to be perturbed.

5.3.3. Method of Modifying RNA Abundances or Activities

Methods of modifying RNA abundances and activities currently fall within three classes, ribozymes, antisense species and RNA aptamers (Good et al., 1997, *Gene Therapy* 4: 45–54). Controllable application or exposure of a cell to these entities permits controllable perturbation of RNA abundances.

Ribozymes are RNAs which are capable of catalyzing RNA cleavage reactions. (Cech, 1987, *Science* 236:1532–1539; PCT International Publication WO 90/11364, published Oct. 4, 1990; Sarver et al., 1990, *Science* 247: 1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, *Nature* 334:585–591; Koizumi et al., 1988, *FEBS Lett.* 228:228–230; Koizumi et al., 1988, *FEBS Lett.* 239:285–288). Ribozyme methods involve exposing a cell to, inducing expression in a cell, etc. of such small RNA ribozyme molecules. (Grassi and Marini, 1996, *Annals of Medicine* 28: 499–510; Gibson, 1996, *Cancer and Metastasis Reviews* 15: 287–299).

Ribozymes can be routinely expressed in vivo in sufficient number to be catalytically effective in cleaving mRNA, and then by modifying mRNA abundances in a cell. (Cotten et al., 1989, *EMBO J.* 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, *Proc. Natl. Acad. Sci. U.S.A.* 86: 6553–6556; Lemaitre et al., 1987, *Proc. Natl. Acad. Sci. U.S.A.* 84: 648–652; PCT Publication No. WO 88/09810, published Dec. 15, 1988), hybridization-triggered cleavage agents (see, e.g., Krol et al., 1988, *BioTechniques* 6: 958–976) or intercalating agents (see, e.g., Zon, 1988, *Pharm. Res.* 5: 539–549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil. dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15: 6625–6641).

The oligonucleotide may be conjugated to another molecule, e.g., a peptide, hybridization triggered cross-linking agent, transport agent, hybridization-triggered cleavage agent, etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16: 3209), methylphosphonate oligonucleotides can be prepared by use of controlled pore glass polymer supports (Sarin et al., 1988, *Proc. Natl. Acad. Sci. U.S.A.* 85: 7448–7451), etc. In another embodiment, the oligonucleotide is a 2'-0-methylribonucleotide (Inoue et al., 1987, *Nucl. Acids Res.* 15: 6131–6148), or a chimeric RNA-DNA analog (Inoue et al., 1987, *FEBS Lett.* 215: 327–330).

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Less preferably usable promoters for mammalian cells include, but are not limited to: the SV40 early promoter region (Bernoist and Chambon, 1981, *Nature* 290: 304–310), the promoter contained in the 3' long terminal repeat of Rous sarcoma virus (Yamamoto et al., 1980, *Cell* 22: 787–797), the herpes thymidine kinase promoter (Wagner et al., 1981, *Proc. Natl. Acad. Sci. USA.* 78: 1441–1445), the regulatory sequences of the metallothionein gene (Brinster et al., 1982, *Nature* 296: 39–42), etc.

Therefore, antisense nucleic acids can be routinely designed to target virtually any mRNA sequence, and a cell can be routinely transformed with or exposed to nucleic acids coding for such antisense sequences such that an effective and controllable amount of the antisense nucleic acid is expressed. Accordingly the translation of virtually any RNA species in a cell can be controllably perturbed.

Finally, in a further embodiment, RNA aptamers can be introduced into or expressed in a cell. RNA aptamers are specific RNA ligands for proteins, such as for Tat and Rev RNA (Good et al., 1997, *Gene Therapy* 4: 45–54) that can specifically inhibit their translation.

5.3.4. Methods of Modifying Protein Abundances

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et al., 1994, *Science* 263:1273–1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell,* Chpt. 8, New York: W. H. Freeman and Co.) with a gene coding for the fus .on protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrons which are responsive to other inducing factors, such as drugs and temperature changes.

Target protein abundances and also, directly or indirectly, their activities can also be decreased by (neutralizing) antibodies. By providing for controlled exposure to such antibodies, protein abundances/activities can be controllably modified. For example, antibodies to suitable epitopes on protein surfaces may decrease the abundance, and thereby indirectly decrease the activity, of the wild-type active form of a target protein by aggregating active forms into complexes with less or minimal activity as compared to the wild-type unaggregated wild-type form. Alternately, antibodies may directly decrease protein activity by, e.g., interacting directly with active sites or by blocking access of substrates to active sites. Conversely, in certain cases, (activating) antibodies may also interact with proteins and their active sites to increase resulting activity. In either case, antibodies (of the various types to be described) can be raised against specific protein species (by the methods to be described) and their effects screened. The effects of the antibodies can be assayed and suitable antibodies selected that raise or lower the target protein species concentration and/or activity. Such assays involve introducing antibodies into a cell (see below), and assaying the concentration of the wild-type amount or activities of the target protein by standard means (such as immunoassays) known in the art. The net activity of the wild-type form can be assayed by assay means appropriate to the known activity of the target protein.

Antibodies can be introduced into cells in numerous fashions, including, for example, microinjection of antibodies into a cell (Morgan et al., 1988, *Immunology Today* 9:84–86) or transforming hybridoma mRNA encoding a desired antibody into a cell (Burke et al., 1984, *Cell* 36:847–858). In a further technique, recombinant antibodies can be engineering and ectopically expressed in a wide variety of non-lymphoid cell types to bind to target proteins as well as to block target protein activities (Biocca et al., 1995, *Trends in Cell Biology* 5:248–252). Preferably, expression of the antibody is under control of a controllable promoter, such as the Tet promoter. A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, *Current Opinion in Immunology* 9:210–212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, *Antibody Engineering,* vol. 2, Borrebaeck ed., IRL Press, pp 295–351). In particular, the ScFv format appears to be particularly suitable for cytoplasmic targeting.

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacillus Calmette-Guerin (BCG) and corynebacterium parvum.

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, *Nature* 256: 495–497), the trioma technique, the human B-cell hybridoma technique (Kozbor et al., 1983, *Immunology Today* 4: 72), and the EBV hybridoma technique to produce human monoclonal antibodies (Cole et al, 1985, in *Monoclonal Antibodies and Cancer Therapy,* Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. U.S.A.* 80: 2026–2030), or by transforming human B cells with EBV virus in vitro (Cole et al., 1985, in *Monoclonal Antibodies and Cancer Therapy,* Alan R. Liss, Inc., pp. 77–96). In fact, according to the invention, techniques developed for the production of "chimeric antibodies" (Morrison et al., 1984, *Proc. Natl. Acad. Sci. U.S.A.* 81: 6851–6855; Neuberger et al., 1984, *Nature* 312:604–608; Takeda et al., 1985, *Nature* 314: 452–454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, *J. Biol. Chem.* 267:16007–16010). Using this technique, libraries of up to $10^{12}$ different antibodies have been expressed on the surface of fd filamentous phage, creating a "single pot" in vitro immune system of antibodies available for the selection of monoclonal antibodies (Griffiths et al., 1994, *EMBO J.* 13:3245–3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946, 778) can be adapted to produce single chain antibodies specific to the target protein. An additional embodiment of the invention utilizes the techniques described for the construction of Fat) expression libraries (Huse et al., 1989, *Science* 246: 1275–1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the F(ab')$_2$ fragment which can be produced by pepsin digestion of the antibody molecule; the Fab' fragments that can be generated by reducing the disulfide bridges of the F(ab')$_2$ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

5.3.5. Methods of Modifying Protein Activities

Methods of directly modifying protein activities include, inter alia, dominant negative mutations, specific drugs (used in the sense of this application) or chemical moieties generally, and also the use of antibodies, as previously discussed.

Dominant negative mutations are mutations to endogenous genes or mutant exogenous genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, *Nature* 329:219–222). In the case of active monomeric forms, over expression of an inactive form can cause competition for natural substrates or ligands sufficient to significantly reduce net activity of the target protein. Such over expression can be achieved by, for example, associating a promoter, preferably a controllable or inducible promoter, of increased activity with the mutant gene. Alternatively, changes to active site residues can be made so that a virtually irreversible association occurs with the target ligand. Such can be achieved with certain tyrosine kinases by careful replacement of active site serine residues (Perlmutter et al., 1996, *Current Opinion in Immunology* 8:285–290).

In the case of active multimeric forms, several strategies can guide selection of a dominant negative mutant. Multimeric activity can be controllably decreased by expression of genes coding exogenous protein fragments that bind to multimeric association domains and prevent multimer formation. Alternatively, controllable over expression of an inactive protein unit of a particular type can tie up wild-type active units in inactive multimers, and thereby decrease multimeric activity (Nocka et al., 1990, *EMBO J.* 9:1805–1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of associations of many subunits of a few types. These structures are often highly sensitive to disruption by inclusion of a few monomeric units with structural defects. Such mutant monomers disrupt the relevant protein activities and can be controllably expressed in a cell.

In addition to dominant negative mutations, mutant target proteins that are sensitive to temperature (or other exogenous factors) can be found by mutagenesis and screening procedures that are well-known in the art.

Also, one of skill in the art will appreciate that expression of antibodies binding and inhibiting a target protein can be employed as another dominant negative strategy.

5.3.6. Drugs of Specific Known Action

Finally, activities of certain target proteins can be controllably altered by exposure to exogenous drugs or ligands. In a preferable case, a drug is known that interacts with only one target protein in the cell and alters the activity of only that one target protein. Graded exposure of a cell to varying amounts of that drug thereby causes graded perturbations of pathways originating at that protein. The alteration can be either a decrease or an increase of activity. Less preferably, a drug is known and used that alters the activity of only a few (e.g., 2–5) target proteins with separate, distinguishable, and non-overlapping effects. Graded exposure to such a drug causes graded perturbations to the several pathways originating at the target proteins.

6. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for processing biological signal profile data for storage in a computer database and for retrieval therefrom by a user comprising the steps of:

storing a plurality of biological signal profiles in said computer database in computer readable form, each said biological signal profile in said plurality of biological signal profiles comprising a plurality of data points, each data point being a measurement of a level of a cellular constituent;

receiving a command from said user to initiate a comparison algorithm, said command identifying a query profile selected from among said plurality of biological signal profiles in said computer database;

computing a plurality of similarity metrics, each similarity metric being computed in accordance with said comparison algorithm, between (i) data points of said query profile and (ii) corresponding data points of a different target profile selected from among said plurality of biological signal profiles stored in computer readable form in said computer database; and communicating as an ordered list said plurality of similarity metrics or said different target profiles, said ordered list being ordered by degree of correlation between said data points of said query profile and said corresponding data points of each said different target profile, thereby processing biological signal profile data for storage in said computer database and for retrieval therefrom by said user.

2. A method for processing biological signal profile data for storage in a computer database and for retrieval therefrom by a user comprising the steps of:

storing a plurality of biological signal profiles in said computer database in computer readable form, each said biological signal profile in said plurality of biological signal profiles comprising a plurality of data points, each data point being a measurement of a level of a cellular constituent;

computing a plurality of similarity metrics, each similarity metric being computed in accordance with a comparison algorithm between (i) data points of a query profile selected from among said plurality of biological signal profiles stored in computer readable form in said computer database, and (ii) corresponding data points of a different target profile selected from among said plurality of biological signal profiles stored in computer readable form in said computer database;

storing said plurality of similarity metrics in said computer database in computer readable form;

receiving a command from said user to initiate said comparison algorithm, said command identifying said query profile;

retrieving from said computer database said plurality of similarity metrics; and communicating as an ordered list said plurality of similarity metrics or said different target profiles, said ordered list being ordered by degree of correlation between said data points of said query profile and said corresponding data points of each said different target profile, thereby processing biological signal profile data for storage in said computer database and for retrieval therefrom by said user.

3. A computer program product for processing biological signal profile data for storage in a computer database and for retrieval therefrom by a user, said computer program product comprising on computer readable medium:

computer code for storing a plurality of biological signal profiles in said computer database in computer readable form, each said biological signal profile in said plurality of biological signal profiles comprising a plurality of data points, each data point being a measurement of a level of a cellular constituent;

computer code for receiving a command from said user to initiate a comparison algorithm, said command identifying a query profile selected from among said plurality of biological signal profiles stored in computer readable form in said computer database;

computer code for computing a plurality of similarity metrics, in accordance with said comparison algorithm, between (i) data points of said query profile and (ii) corresponding data points of a different target profile selected from among said plurality of biological signal profiles stored in computer readable form in said computer database; and computer code for communicating as an ordered list said plurality of similarity metrics or said different target profiles, said ordered list being ordered by degree of correlation between said data points of said query profile and said corresponding data points of each said different target profile, thereby processing biological signal profile data for storage in said computer database and for retrieval therefrom by said user.

4. A computer program product for processing biological signal profile data for storage in a computer database and for retrieval therefrom by a user, said computer program product comprising on computer readable medium:

computer code for storing a plurality of biological signal profiles in said computer database in computer readable form, each said biological signal profile in said plurality of biological signal profiles comprising a plurality of data points, each data point being a measurement of a level of a cellular constituent;

computer code for computing a plurality of similarity metrics, each similarity metric being computed in accordance with a comparison algorithm between (i) data points of a query profile selected from among said plurality of biological signal profiles stored in computer readable form in said computer database, and (ii) corresponding data points of a different target profile selected from among said plurality of biological signal profiles stored in computer readable form in said computer database;

computer code for storing said plurality of similarity metrics in said computer database in computer readable form;

computer code for receiving a command from said user to initiate said comparison algorithm, said command identifying said query profile;

computer code for retrieving from said computer database said plurality of similarity metrics; and computer code for communicating as an ordered list said plurality of similarity metrics, or said different target profiles, said ordered list being ordered by degree of correlation between said data points of said query profile and said corresponding data points of each said different target profile thereby processing biological signal profile data for storage in said computer database and for retrieval therefrom by said user.

5. A computer system for processing biological signal profile data for storage in a computer database and for retrieval therefrom by a user, the computer system comprising:

one or more processors;

storage media for storing a computer database;

a program module, executable by said one or more processors, for processing said biological signal profile data, said program module comprising:

instructions for storing a plurality of biological signal profiles in said computer database in computer readable form, each said biological signal profile in said plurality of biological signal profiles comprising a plurality of data points, each data point being a measurement of a level of a cellular constituent;

instructions for receiving a command from said user to initiate a comparison algorithm, said command identifying a query profile selected from among said plurality of biological signal profiles stored in computer readable form in said computer database;

instructions for computing a plurality of similarity metrics, each similarity metric being computed in accordance with said comparison algorithm, between (i) data points of said query profile and (ii) corresponding data points of a different target profile selected from among said plurality of biological signal profiles stored in computer readable form in said computer database; and instructions for communicating as an ordered list said plurality of similarity metrics or said different target profiles, said ordered list being ordered by degree of correlation between said data points of said query profile and said corresponding data points of each said different target profile, thereby processing biological signal profile data for storage in said computer database and for retrieval therefrom by said user.

6. A computer system for processing biological signal profile data for storage in a computer database and for retrieval therefrom by a user, the computer system comprising:

one or more processors;

storage media for storing a computer database;

a program module, executable by said one or more processors, for processing said biological signal profile data, said program module comprising:

instructions for storing a plurality of biological signal profiles in said computer database in computer readable form, each said biological signal profile in said plurality of biological signal profiles comprising a plurality of data points, each data point being a measurement of a level of a cellular constituent;

instructions for computing a plurality of similarity metrics, each similarity metric being computed in accordance with a comparison algorithm, between (i) data points of a query profile selected from among said plurality of biological signal profiles stored in computer readable form in said computer database and (ii) corresponding data points of a different target profile selected from among said plurality of biological signal profiles stored in computer readable form in said computer database;

instructions for receiving a command from said user to initiate said comparison algorithm, said command identifying said query profile;

instructions for communicating as an ordered list said plurality of similarity metrics or said different target profiles, said ordered list begin ordered by degree of correlation between said data points of said query profile and said corresponding data points of each said different target profile thereby processing biological signal profile data for storage in said computer database and for retrieval therefrom by said user;

wherein said instructions for receiving said command from said user to initiate said comparison algorithm are to be executed at a time subsequent to execution of said instructions for computing said similarity metrics.

7. A computer system for processing biological signal profile data for storage in a computer database and for retrieval therefrom by a user, said computer system comprising:

one or more processors;

storage media for storing a computer database;

a program module, executable by said one or more processors, for processing said biological signal profile data, said program module comprising:

instructions for storing a plurality of biological signal profiles in said computer database in computer readable form, each said biological signal profile in said plurality of biological signal profiles comprising a plurality of data points, each data point being a measurement of a level of a cellular constituent;

instructions for computing a plurality of similarity metrics, each similarity metric being computed in accordance with a comparison algorithm between (i) data points of a query profile selected from among said plurality of biological signal profiles stored in computer readable form in said computer database, and (ii) corresponding data points of a different target profile selected from among said plurality of biological signal profiles stored in computer readable form in said computer database;

instructions for storing said plurality of similarity metrics in said computer database in computer readable form;

instructions for receiving a command from said user to initiate said comparison algorithm, said command identifying said query profile;

instructions for retrieving from said computer database said plurality of similarity metrics; and instructions for communicating as an ordered list said plurality of similarity metrics or said different target profiles, said ordered list being ordered by degree of correlation between said data points of said query profile and said corresponding data points of each said different target profile, thereby processing biological signal profile data for storage in said computer database and for retrieval therefrom by said user.

8. A method for processing biological signal profile data comprising the steps of:

receiving a command from a user to initiate a comparison algorithm, said command identifying a query profile selected from among a plurality of biological signal profiles stored in computer readable form in a computer database, each said biological signal profile in said plurality of biological signal profiles comprising a plurality of data points, each data point being a measurement of a level of a cellular constituent;

computing a plurality of similarity metrics, each similarity metric being computed in accordance with said comparison algorithm between (i) data points of said query profile and (ii) corresponding data points of a different target profile selected from among said plurality of biological signal profiles stored in computer readable form in said computer database; and communicating as an ordered list said plurality of similarity metrics or said different target profiles, said ordered list being ordered by degree of correlation between said data points of said query profile and said corresponding data points of each said different target profile, thereby processing biological signal profile data.

9. A method for processing biological signal profile data comprising the steps of:

receiving a command from a user to initiate a comparison algorithm, said command identifying a query profile selected from among a plurality of biological signal profiles stored in computer readable form in a computer database, each said biological signal profile in said plurality of biological signal profiles comprising a plurality of data points, each data point being a measurement of a level of a cellular constituent;

retrieving, from said computer database, a plurality of similarity metrics stored in computer readable form in said computer database, each similarity metric having been computed, in accordance with said comparison algorithm, between (i) data points of said query profile and (ii) corresponding data points of a different target profile selected from among said plurality of biological signal profiles stored in computer readable form in said computer database; and communicating as an ordered list said plurality of similarity metrics or said different target profiles, said ordered list being ordered by degree of correlation between said data points of said query profile and said corresponding data points of each said different target profile, thereby processing biological signal profile data.

10. A computer program product for processing biological signal profile data, said computer program product comprising on computer readable medium:

computer code for receiving a command from a user to initiate a comparison algorithm, said command identifying a query profile selected from among a plurality of biological signal profiles stored in computer readable form in a computer database, each said biological signal profile in said plurality of biological signal profiles comprising a plurality of data points, each data point being a measurement of a level of a cellular constituent;

computer code for computing a plurality of similarity metrics, each similarity metric being computed in accordance with said comparison algorithm, between (i) data points of said query profile, and (ii) corresponding data points of a different target profile selected from among said plurality of biological signal profiles stored in computer readable form in said computer database; and computer code for communicating as an ordered list said plurality of similarity metrics or said different target profiles, said ordered list being ordered by degree of correlation between said data points of said query profile and said corresponding data points of each said different target profile, thereby processing biological signal profile data.

11. A computer program product for processing biological signal profile data, said computer program product comprising on computer readable medium:

computer code for receiving a command from a user to initiate a comparison algorithm, said command identifying a query profile selected from among a plurality of biological signal profiles stored in computer readable form in a computer database, each said biological signal profile in said plurality of biological signal profiles comprising a plurality of data points, each data point being a measurement of a level of a cellular constituent;

computer code for retrieving, from said computer database, a plurality of similarity metrics stored in computer readable form in said computer database, each similarity metric in said plurality of similarity metrics having been computed in accordance with said comparison algorithm between (i) data points of said query profile and (ii) corresponding data points of a different target profile selected from among said plurality of biological signal profiles stored in computer readable form in said computer database; and computer code for communicating as an ordered list said plurality of similarity metrics or said different target profiles, said ordered list being ordered by degree of correlation between said data points of said query profile and said corresponding data points of each said different target profile, thereby processing biological signal profile data.

12. A computer system for processing biological signal profile data, the computer system comprising:

one or more processors;

storage media for storing a computer database;

a program module, executable by said one or more processors, for processing said biological signal profile data, said program module comprising:

instructions for receiving a command from a user to initiate a comparison algorithm, said command identifying a query profile selected from among a plurality of biological signal profiles stored in said computer database in computer readable form, each said biological signal profile in said plurality of biological signal profiles comprising a plurality of data points, each data point being a measurement of a level of a cellular constituent;

instructions for computing a plurality of similarity metrics, each similarity metric being computed in accordance with said comparison algorithm, between (i) data points of said query profile and (ii) corresponding data points of a different target profile selected from among said plurality of biological signal profiles stored in computer readable form in said computer database; and instructions for communicating as an ordered list said plurality of similarity metrics or said different target profiles, said ordered list being ordered by degree of correlation between said data points of said query profile and said corresponding data points of each said different target profile, thereby processing biological signal profile data.

13. A computer system for processing biological signal profile data, the computer system comprising:

one or more processors;

storage media for storing a computer database;

a program module, executable by said one or more processors, for processing said biological signal profile data, said program module comprising:

instructions for receiving a command from a user to initiate a comparison algorithm, said command identifying a query profile selected from among a plurality of biological signal profiles stored in computer readable form in said computer database, each said biological signal profile in said plurality of biological signal profiles comprising a plurality of data points, each data point being a measurement of a level of a cellular constituent;

instructions for retrieving, from said computer database, a plurality of similarity metrics stored in computer readable form in said computer database, each similarity metric in said plurality of similarity metrics having been computed between (i) data points of said query profile, and (ii) corresponding data points of a different target profile selected from among said plurality of biological signal profiles stored in computer readable form in said computer database; and instructions for communicating as an ordered list said plurality of similarity metrics or said different target profiles, said ordered list being ordered by degree of correlation between said data points of said query profile and said corresponding data points of each said different target profile, thereby processing biological signal profile data.

14. A computer network for processing biological signal profile data for storage in a computer database and for retrieval therefrom by a user, the computer network comprising:

a first computer and a second computer; and a data network coupled to said first and said second computer;

said first computer comprising:
a first processor;
a first storage media for storing a computer database;
a first program module, executable by said first processor, said first program module comprising:
instructions for storing a plurality of biological signal profiles in computer readable form in said computer database, each said biological signal profile in said plurality of biological signal profiles comprising a plurality of data points, each data point being a measurement of a level of a cellular constituent; and
instructions for receiving a command from said user to initiate a comparison algorithm, said command identifying a query profile selected from among said plurality of biological signal profiles stored in computer readable form in said computer database; and said second computer comprising:
a second processor;
a second program module, executable by said second processor, said second program module comprising:
instructions for computing a plurality of similarity metrics, each similarity metric being computed in accordance with said comparison algorithm, between (i) data points of said query profile, and (ii) corresponding data points of a different target profile selected from among said plurality of biological signal profiles stored in computer readable form in said computer database; and
instructions for communicating as an ordered list said plurality of similarity metrics or said different target profiles, said ordered list being ordered by degree of correlation between said data points of said query profile and said corresponding data points of each said different target profile.

15. A computer network for processing biological signal profile data for storage in a computer database and for retrieval therefrom by a user, the computer network comprising:

a first computer and a second computer; and a data network coupled to said first and said second computer;

said first computer comprising:
a first processor;
a first storage media for storing said computer database;
a first program module, executable by said first processor, said first program module comprising:
instructions for storing a plurality of biological signal profiles in said computer database in computer readable form, each said biological signal profile in said plurality of biological signal profiles comprising a plurality of data points, each data point being a measurement of a level of a cellular constituent;
instructions for receiving a command from said user to initiate a comparison algorithm, said command identifying a query profile selected from among said plurality of biological signal profiles stored in computer readable form in said computer database;
instructions for retrieving from said computer database a plurality of similarity metrics, each similarity metric in said plurality of similarity metrics having been computed in accordance with said comparison algorithm between said query profile and a different target profile selected from among said plurality of biological signal profiles stored in computer readable form in said computer database; and
instructions for communicating as an ordered list said plurality of similarity metrics or said different target profiles, said ordered list being ordered by degree of correlation between said data points of said query profile and said corresponding data points of each said different target profile; and said second computer comprising:
a second processor;
a second program module, executable by said second processor, said second program module comprising:
instructions for computing said plurality of similarity metrics; and
instructions for storing said plurality of similarity metrics in said computer database in computer readable form.

16. A computer network for processing biological signal profile data, the computer network comprising:

a first computer and a second computer; and a data network coupled to said first and said second computer;

said first computer comprising:
a first processor;
a first storage media for storing a computer database;
a first program module, executable by said first processor, for processing said biological signal profile data, said first program module comprising:
instructions for receiving a command from a user to initiate a comparison algorithm, said command identifying a query profile selected from among a plurality of biological signal profiles stored in computer readable form in said computer database, each said biological signal profile in said plurality of biological signal profiles comprising a plurality of data points, each data point being a measurement of a level of a cellular constituent; and said second computer comprising:
a second processor;
a second program module, executable by said second processor, said second program module comprising instructions for computing said plurality of similarity metrics, each similarity metric being computed in accordance with said comparison algorithm, between (i) data points of said query profile and (ii) corresponding data points of a different target profile selected from among said plurality of biological signal profiles stored in computer readable form in said computer database; and said first program module further comprising:
instructions for communicating as an ordered list said plurality of similarity metrics or said different target profiles represented by said plurality of similarity metrics, said plurality of similarity metrics or said different target profiles in said ordered list being ordered by degree of correlation between said data points of said query profile and said corresponding data points of each said different target profile.

17. A method of using a computer network for processing biological signal profile data for storage in a computer database and for retrieval therefrom by a user, the method comprising:
storing a plurality of biological signal profiles in computer readable form in said computer database, each said biological signal profile in said plurality of biological signal profiles comprising a plurality of data points, each data point being a measurement of a level of a cellular constituent; and
receiving a command from said user to initiate a comparison algorithm, said command identifying a query profile selected from among said plurality of biological signal profiles stored in computer readable form in said computer database;
computing a plurality of similarity metrics, each similarity metric being computed in accordance with said comparison algorithm, between (i) data points of said query profile, and (ii) corresponding data points of a different target profile selected from among said plurality of biological signal profiles stored in computer readable form in said computer database; and
communicating as an ordered list said plurality of similarity metrics or said different target profiles, said ordered list being ordered by degree of correlation between said data points of said query profile and said corresponding data points of each said different target profile.

18. The computer system of claim 6, wherein said plurality of similarity metrics is to be computed by said instructions for computing said plurality of similarity metrics using said one or more processors at a time prior to execution of said instructions for receiving said command from said user to initiate said comparison algorithm, thereby decreasing a time required until said instructions for communicating are initiated.

19. The method of claim 1, 2, 8, or 9 wherein said computer database is a relational database.

20. The method of claim 1, 2, 8 or 9 wherein said computer database is an object oriented database.

21. The method of claim 1, 2, 8, or 9 wherein said plurality of biological signal profiles comprise gene expression level data.

22. The computer program product of claim 3, 4, 10 or 11 wherein said plurality of biological signal profile comprise gene expression level data.

23. The computer system of claim 5, 7, 12 or 13, wherein said plurality of biological signal profiles comprise gene expression level data.

24. The method of claim 1, 2, 8, or 9 wherein said plurality of biological signal profiles comprise protein expression level data.

25. The computer program product of claim 3, 4, 10 or 11 wherein said plurality of biological signal profiles comprise protein expression level data.

26. The computer system of claim 5, 7, 12 or 13, wherein said plurality of biological signal profiles comprise protein expression level data.

27. The computer network of claim 14, 15, or 16, wherein each said similarity metric in said plurality of similarity metrics consists of a single scalar correlation coefficient.

28. The computer network of claim 14, 15, or 16, wherein each said similarity metric in said plurality of similarity metrics consists of a multidimensional correlation matrix.

29. The computer network of claim 14, 15, or 16, said first program module further comprising instructions for storing said plurality of similarity metrics in said database.

30. The computer network of claim 14, said first program module further comprising instructions for user directed selection of the data points of said query profile and the data points of each said different target profile between which said plurality of similarity metrics is computed.

31. The computer network of claim 15, said first program module further comprising instructions for user directed selection of the data points of said query profile and the data points of each said different target profile between which said plurality of similarity metrics is computed.

32. The computer network of claim 14, 15, or 16, wherein said instructions for receiving said command comprises instructions for selecting said query profile.

33. The computer network of claim 14, 15, or 16, wherein said plurality of biological signal profiles comprise gene expression level data.

34. The computer network of claim 14, 15, or 16, wherein said plurality of biological signal profiles comprise protein expression level data.

35. The method of claim 1 or 8, wherein each said similarity metric in said plurality of similarity metrics consists of a single scalar correlation coefficient.

36. The method of claim 1 or 8, wherein each said similarity metric in said plurality of similarity metrics consists of a multidimensional correlation matrix.

37. The method of claim 1 or 8, further comprising the step of storing said plurality of similarity metrics in said computer database.

38. The method of claim 1 or 8 further comprising a step of selecting the data points of said query profile and the corresponding data points of each said different target profile between which said plurality of similarity metrics is computed.

39. The method of claim 2 or 9 further comprising a step of selecting the data points of said query profile and the corresponding data points of each said different target profile between which said plurality of similarity metrics is computed.

40. The method of claim 1, 2, 8 or 9, wherein said step of receiving said command comprises a step of selecting said query profile and each said different target profile.

41. The computer program product of claim 3 or 10, wherein each said similarity metric in said plurality of similarity metrics consists of a single scalar correlation coefficient.

42. The computer program product of claim 3 or 10, wherein each said similarity metric in said plurality of similarity metrics consists of a multidimensional correlation matrix.

43. The computer program product of claim 3 or 10, said computer program product further comprising computer code for storing said plurality of similarity metrics in said computer database.

44. The computer program product of claim 3 or 10, further comprising computer code for user directed selection of the data points of said query profile and the data points of each said different target profile between which said plurality of similarity metrics is computed.

45. The computer program product of claim 4 or 11, further comprising computer code for user directed selection of the data points of said query profile and the data points of each said different target profile between which said plurality of similarity metrics is computed.

46. The computer program product of claim 45, wherein said computer code for receiving said command comprises computer code for selecting said query profile and each said different target profile.

47. The computer program product of claim 46, said computer code for selecting said query profile and each said different target profile comprising:
    computer code for displaying a search menu; and
    computer code for receiving search menu and alphanumeric inputs from the user.

48. The computer program product of claim 46, said computer code for selecting said query profile and each said different target profile comprising:
    computer code for receiving a graphical selection command from the user.

49. The computer system of claim 5 or 12, wherein each said similarity metric in said plurality of similarity metrics consists of a single scalar correlation coefficient.

50. The computer system of claim 5 or 12, wherein each said similarity metric in said plurality of similarity metrics consists of a multidimensional correlation matrix.

51. The computer system of claim 5 or 12, said program module further comprising instructions for storing said plurality of similarity metrics in said computer database.

52. The computer system of claim 5 or 12, wherein said program module further comprises instructions for user directed selection of the data points of said query profile and the data points of each said different target profile between which said plurality of similarity metrics are computed.

53. The computer system of claim 7 or 13, wherein said program module further comprises instructions for user directed selection of the data points of said query profile and the data points of each said different target profile between which said plurality of similarity metrics are computed.

54. The computer system of claim 5, 7, 12, or 13, wherein said instructions for receiving said command comprises instructions for selecting said query profile and each said different target profile.

55. The computer system of claim 54, said instructions for selecting said query profile and each said different target profile comprising:
    instructions for displaying a search menu; and
    instructions for receiving search menu and alphanumeric inputs from the user.

56. The computer system of claim 54, said instructions for selecting said query profile and each said different target profile comprising:
    instructions for receiving a graphical selection command from the user.

57. The method of claim 40, said step of selecting said query profile and each said different target profile comprising the steps of displaying a search menu and receiving search menu and alphanumeric inputs from the user.

58. The method of claim 40, said step of selecting said query profile and each said different target profile comprising the step of receiving a graphical selection command from the user.

59. The method of claim 2, wherein said step of receiving said command from said user to initiate said comparison algorithm is executed at a time subsequent to said step of computing said plurality of similarity metrics.

60. The computer program product of claim 4 wherein said computer code for receiving said command from said user to initiate said comparison algorithm is to be executed at a time subsequent to execution of said computer code for computing said plurality of similarity metrics.

61. The computer program product of claim 3 or 10 wherein said computer code for receiving said command from said user to initiate said comparison algorithm is to be executed at a time subsequent to execution of said computer code for computing said plurality of similarity metrics.

62. The computer system of claim 7 wherein said instructions for receiving said command from said user to initiate said comparison algorithm are to be executed at a time subsequent to execution of said instructions for computing said plurality of similarity metrics.

63. The method of claim 17, wherein each said similarity metric in said plurality of similarity metrics consists of a single scalar correlation coefficient.

64. The method of claim 17, wherein each said similarity metric in said plurality of similarity metrics consists of a multidimensional correlation matrix.

65. The method of claim 17, further comprising storing each said similarity metric in said plurality of similarity metrics in said computer database.

66. The method of claim 17, further comprising a step of selecting the data points of said query profile and the data points of each said different target profile between which said plurality of similarity metrics is computed.

67. The method of claim 17, wherein said step of receiving said command comprises a step of selecting said query profile.

68. The method of claim 17, wherein said plurality of biological signal profiles comprise gene expression level data.

69. The method claim 17, wherein said plurality of biological signal profiles comprise protein expression level data.

70. The method of claim 1 wherein at least one biological signal profile used in an instance of said computing step comprises data points measured in response to a perturbation to a cell or an organism.

71. The method of claim 2 wherein at least one biological signal profile used in an instance of said computing step comprises data points measured in response to a perturbation to a cell or an organism.

72. The computer program product of claim 3 wherein at least one biological signal profile used by said computer code for computing said plurality of similarity metrics comprises data points measured in response to a perturbation to a cell or an organism.

73. The computer program product of claim 4 wherein at least one biological signal profile used by said computer code for computing said plurality of similarity metrics comprises data points measured in response to a perturbation to a cell or an organism.

74. The computer system of claim 5 wherein at least one biological signal profile used by said instructions for computing said plurality of similarity metrics comprises data points measured in response to a perturbation to a cell or an organism.

75. The computer system of claim 6 wherein at least one biological signal profile used by said instructions for computing said plurality of similarity metrics comprises data points measured in response to a perturbation to a cell or an organism.

76. The computer system of claim 7 wherein at least one biological signal profile used by said instructions for computing said plurality of similarity metrics comprises data points measured in response to a perturbation to a cell or an organism.

77. The method of claim 8 wherein at least one biological signal profile used in an instance of said computing step comprises data points measured in response to a perturbation to a cell or an organism.

78. The method of claim 9 wherein at least one biological signal profile used in an instance of said computing step comprises data points measured in response to a perturbation to a cell or an organism.

79. The computer program product of claim 10 wherein at least one biological signal profile used by said computer code for computing said plurality of similarity metrics comprises data points measured in response to a perturbation to a cell or an organism.

80. The computer program product of claim 11 wherein at least one biological signal profile used by said computer code for computing said plurality of similarity metrics comprises data points measured in response to a perturbation to a cell or an organism.

81. The computer system of claim 12 wherein at least one biological signal profile used by said instructions for computing said plurality of similarity metrics comprises data points measured in response to a perturbation to a cell or an organism.

82. The computer system of claim 13 wherein at least one biological signal profile used by said instructions for computing said plurality of similarity metrics comprises data points measured in response to a perturbation to a cell or an organism.

83. The computer network of claims 14, 15 or 16, wherein at least one biological signal profile used by said instructions for computing said plurality of similarity metrics comprises data points measured in response to a perturbation to a cell or an organism.

* * * * *